(12) United States Patent
Chosdol et al.

(10) Patent No.: US 9,556,437 B2
(45) Date of Patent: Jan. 31, 2017

(54) FAT1 GENE IN CANCER AND INFLAMMATION

(71) Applicants: DEPARTMENT OF BIOTECHNOLOGY (DBT), New Delhi (IN); ALL INDIA INSTITUTE OF MEDICAL SCIENCES (AIIMS), New Delhi (IN); NATIONAL BRAIN RESEARCH CENTRE (NBRC), Haryana (IN)

(72) Inventors: Kunzang Chosdol, New Delhi (IN); Bhawana Dikshit, New Delhi (IN); Subrata Sinha, Haryana (IN)

(73) Assignees: DEPARTMENT OF BIOTECHNOLOGY (DBT), New Delhi (IN); ALL INDIA INSTITUTE OF MEDIAL SCIENCES (AIIMS), New Delhi (IN); NATIONAL BRAIN RESEARCH CENTRE (NBRC), Haryana (IN)

( * ) Notice: Subject to any disclaimer, the term of this patent is extended or adjusted under 35 U.S.C. 154(b) by 0 days.

(21) Appl. No.: 14/323,687

(22) Filed: Jul. 3, 2014

(65) Prior Publication Data

US 2014/0323547 A1 Oct. 30, 2014

Related U.S. Application Data

(63) Continuation-in-part of application No. PCT/IB2013/050086, filed on Jan. 4, 2013.

(30) Foreign Application Priority Data

Jan. 5, 2012 (IN) ................. 45/DEL/2012

(51) Int. Cl.
| | |
|---|---|
| *A61K 48/00* | (2006.01) |
| *C07H 21/02* | (2006.01) |
| *C07H 21/04* | (2006.01) |
| *C12N 15/113* | (2010.01) |
| *C12Q 1/68* | (2006.01) |

(52) U.S. Cl.
CPC ....... *C12N 15/1136* (2013.01); *C12N 15/1135* (2013.01); *C12N 15/1138* (2013.01); *C12Q 1/6886* (2013.01); *C12N 2310/14* (2013.01)

(58) Field of Classification Search
CPC ...... A61K 48/00; C12N 15/111; C12N 15/113
See application file for complete search history.

(56) References Cited

U.S. PATENT DOCUMENTS

| | | |
|---|---|---|
| 8,313,772 B2 | 11/2012 | Rozema et al. |
| 8,389,708 B2 | 3/2013 | Min |
| 8,541,568 B2 | 9/2013 | Yan et al. |
| 8,742,091 B2 | 6/2014 | Terada et al. |
| 2004/0219579 A1 | 11/2004 | Aziz et al. |
| 2006/0275287 A1 | 12/2006 | ST Croix et al. |

OTHER PUBLICATIONS

International Search Report of International Application No. PCT/IB2013/050086 dated May 1, 2012.
Valleta D et al., "904 Increased Expression of FAT1 in Hepatocellular Carcinoma Promotes Tumorigenicity", Journal of Hepatology, Munksgaard International Publishers, Copenhagen, DK, vol. 52, 2010, pp. S351.
Yukiko Nishikawa, "Human FAT1 Cadherin Controls Cell Migration and Invasion of Oral Squamous Cell Carcinoma Through the Localization of [beta] -Catenin", Oncology Reports, 2011.
Alireza Ardjmand et al., "Altered Expression of FAT1 Cadherin, a Novel Tumor Marker for Acute Lymphoblastic Leukemia", Clinical Biochemistry, vol. 44 (13), 2011, pp. S71.
Dikshit et al., FAT1 Acts as an Upstream Regulator of Oncogenic and Inflammatory Pathways, via PDCD4, in Glioma cells, Oncogene, 2012.
Dikshit et al., "Overexpression of FAT1 in Human GBM (glioblastoma multiforme) and High-grade Glioma Cell Lines", Cancer Research, vol. 71 (18), 2011.
Adler et al., "Mutations in the Cadherin Superfamily Member Gene Dachsous Cause a Tissue Polarity Phenotype by Altering Frizzled Signaling", Development, vol. 125 (5), 1997, pp. 959-968.
Mantovani et al., "Cancer-related Inflammation", Nature, vol. 454 (7203), 2008, pp. 436-443.
Allavena et al., "The Inflammatory Micro-Environment in Tumor Progression: The Role of Tumor-Associated Macrophages", Critical Reviews in Oncology Hematology, 2008, pp. 1-9.
McClatchey et al., "Membrane Organization and Tumorigenesis—the NF2 tumor supressor, Merlin", Genes & Development, vol. 19 (19), 2005, pp. 2265-2277.
Angst et al., "The Cadherin Superfamily: Diversity in Form and Function", Jounal of Cell Science, 2001, pp. 629-641.

(Continued)

*Primary Examiner* — Amy Bowman
(74) *Attorney, Agent, or Firm* — Roberts Mlotkowski Safran Cole & Calderon P.C.

(57) ABSTRACT

The present invention demonstrates for the first time that FAT1 plays an important role in modulating PDCD4 expression, which in turn regulates AP-1 dependent transcription, controls processes crucial for migration and invasion in cancer cells, controls induction of a pro-inflammatory micro environment in cancer cells. The study illustrates a link between inflammation and cancer in cells or in a subject. This work highlights the importance of FAT1 in the induction of the cellular pathways of migration and invasion, proteolysis of the ECM and the expression of pro-inflammatory molecules leading to a favorable micro environment for tumor and cancer progression. The present invention also provides the use of FAT1 in regulating neoplastic phenotypes and genotypes including invasiveness and inflammatory micro environment of the cancer cells by acting as a novel apical regulator of a signaling pathway by affecting the AP1 transcriptional activity, affecting the property of both cell migration and invasion and at the same time affecting the expression of inflammatory modulators. The present invention also identifies a novel regulatory pathway for inflammatory mediators and inflammatory cellular responses via PDCD4 and AP1. The invention describes a pathway for the upregulation of inflammatory processes as such, and hence a means of regulating inflammatory pathologies in general.

15 Claims, 19 Drawing Sheets

(56) References Cited

OTHER PUBLICATIONS

Navis et al., "Protein Tyrosine Phosphatases in Glioma Biology", Acta Neuropathol, vol. 119 (2), 2009, pp. 157-159.
Baena-Lopez et al., "The Orientation of Cell Divisions Determines the Shape of Drosophila Organs", Current Biology, vol. 15 (18), 2005, pp. 1640-1644.
Baia et al., "Yes-Associated Protein 1 is Activated and Functions as an Oncogene in Meningiomas", Molecular Cancer Research, vol. 15 (18), 2012, pp. 904-913.
Bao et al., "Mammalian Hippo Pathway: From Development to Cancer and Beyond", The Journal of Biochemistry, vol. 149 (4), 2011, pp. 361-379.
Baumgartner et al., "The WW Domain Protein Kibra Acts Upstream of Hippo in *Drosophila*", Developmental Cell, vol. 18, 2010, pp. 309-316.
Bear et al., "Antagonism Between Ena/VASP Proteins and Actin Filament Capping Regulates Fibroblast Motility", Cell, vol. 109 (4), 2002, pp. 509-521.
Belozerov et al., "Inhibitors of Hypoxia-Inducible Factor-1 Signaling", Curr Opin Investig Drugs, 2006, pp. 1067-1076, (Abstract Only).
Bendavid et al., "Phenotypic Variability of a 4q34-->qter Inherited Deletion: MRKH Syndrome in the Daughter, Cardiac Defect and Fallopian Tube Cancer in the Month", Eur J Med Genet, vol. 50 (1), 2007, pp. 66-72, (Abstract Only).
Bennett et al., "Fat Cadherin Modulates Organ Size in *Drosophilia* via the Salvador/Warts/Hippo Signaling Pathway", Current Biology, vol. 16 (21), 2006, pp. 2101-2110.
Bhattacharya et al., "Regulation of the Urokinase-type Plasminogen Activator Receptor Gene in Different Grades of Human Glioma Cell Lines", Clinical Cancer Research, vol. 7 (2), 2001, pp. 267-276.
Allevena et al., "Pathways connecting inflammation and cancer", Current Opinion in Genetics & Development, vol. 18 (1) pp. 3-10, 2008.
Bitomsky et al., "Transformation Suppressor Protein Pdcd4 Interferes with JNK-mediated Phosphorylation of c-Jun and Recruitment of the Coactivator p300 by c-Jun", Oncogene, vol. 23 (45), 2004, pp. 7484-7493.
Boudreau et al., "Gliomas: Advances in molecular Analysis and Characterization", Surg Neurol, vol. 64 (4), 2005, pp. 286-294, (Abstract Only).
Braun et al., "Differntially Spliced Isoforms of FAT1 are Asymmetrically Distributed Within Migrating Cells", Journal of Biological Chemistry, vol. 282 (31), 2007, pp. 22823-22833.
Brittle et al., "Planar Polarity Specification through Asymmetric Subcellular Localization of Fat and Dachsous", Current Biology, vol. 22 (10), 2012, pp. 907-914.
Bryant et al., "Mutations at the Fat Locus Interfere with Cell Proliferation Control and epithelial Morphogenesis in *Drosophila*", Dev Biology, vol. 129 (2), 1998, pp. 541-554, (Abstract Only).
Carro et al., "The Transcriptional network for mesenchymal Transformation of Brain Tumors", Nature, vol. 463 (7279), 2010, pp. 1-23.
Chang et al., "Assessment of Chromosomal losses and Gains in Hepatocellular Carcinoma", Cancer Lett, vol. 182 (2), 2002, pp. 193-202, (Abstract Only).
Chen et al, "The Hippo Pathway Controls polar Cell Fate Through Notch Signaling During *Drosophila* Oogenesis", Developmental Biology, vol. 357 (2), 2011, pp. 370-379.
Cho et al., "Delineation of a Fat Tumor Suppressor Pathway", Nat Genet, vol. 38 (10), 2006, pp. 1142-1150, (Abstract Only).
Cho et al., "Identification of tumor Suppressor Loci on the Long Arm of Chromosome 4 in primary Small Cell Lung Cancers", Yonsei Medical Journal, vol. 43 (2), 2002, pp. 145-151.
Backsch et al., "A Regiion on Human Chromosome 4 (q35.I->qter) Induces Senescence in Cell Hybrids and Is Involved in Cervical Carcinogenesis", Genes, Chromosomes & Cancer, vol. 43 (3) pp. 260-272, 20005.

Chosdol et al., "Frequent Loss of Heterozygosity and Altered Expression of the Candidate Tumor Suppressor gene FAT in Human Astrocytic Tumors", BMC Cancer, vol. 9 (5), 2009.
Clark et al., "Dachsous Encodes a member of the Cadherin Superfamily That Controls Imaginal Disc Morphogenesis in *Drosophila*", Genes & Development, vol. 9 (12), 1995, pp. 1530-1542.
Colotta et al., "Cancer-Related Inflammation, the Seventh Hallmark of Cancer: Links to Genetic Instability", Carcinogenesis, vol. 30 (7), 2009, pp. 1073-1081.
Conti et al., "Role of Inflammation and Oxidative Stress Mediators in Gliomas", Cancers, vol. 2 (2), 2010, pp. 693-712.
Coussens et al., "Inflmmatory mast Cells Up-regulate Angiogenesis during Squamous Epithelial Cacinogenesis", Genes Development, vol. 13 (11), 1999, pp. 1382-1397.
Cox et al., "Cloning and Expression Throughout Mouse Development of mfat1, a homologue of the *Drosophila* Tumour Suppressor Gene fat", Developmental Dynamics, vol. 217 (3), 2000, pp. 233-240.
De Bock et al., "The Fat1 Cadherin is Overexpressed and an Independent Prognostic Factor for Survival in paired Diagnosis—Relapse Samples of Precursor B-cell Acute Lymphoblastic Leukemia", Leukemia, vol. 26 (5), 2011, pp. 918-926.
De Visser et al., "Towards Understanding the Role of Cancer-Associated Inflammation in Chemoresistance", Curr Pharm Des, vol. 15 (16), 2009, pp. 1843-1853, (Abstract Only).
Von Deimling et al., "Deletions on the Long Arm of Chromosome 17 in Pilocytic Astrocytoma", Acta Neruopathol, vol. 86 (1), 1993, pp. 81-85.
Demaria et al., "Cancer and Inflammation: Promise for Biological Therapy", J Immunother, vol. 33 (4), 2010, pp. 335-351.
Deorukhkar et al., "Targeting Inflammatory pathways for Tumor Radiosensitization" Biochem Pharmacol, vol. 80 (12), 2010, pp. 1904-1914.
Dong et al., "Elucidation of a Universal Size-Control Mechanism in *Drosophila* and Mammals", Cell, vol. 130 (6), 2007, pp. 1120-1133.
Down et al., "Cloning and Expression of the Large Zebrafish Protocadherin Gene, Fat", Gene Expr Patterns, vol. 5 (4), 2005, pp. 483-490, (Abstract Only).
Egeblad et al., "New Functions for the Matrix Metalloproteinases in Cancer Progression", Nat Rev Cancer (2002), pp. 161-174, (Abstract Only).
Fanto et al., "The Tumor-Suppressor and Cell Adhesion Molecule Fat Controls Planar Polarity Via Physical Interactions With Atrophin, a Transcriptional Co-Repressor", Development, vol. 130 (4), 2003, pp. 763-774.
Figarella et al., "Histological and Molecular Classification of Gliomas", Rev Neurol (Paris), vol. 164 (6-7), 2008, pp. 505-515, (Abstract Only).
Fischer et al., "Angiogenesis in Gliomas: Biology and Molecular Pathophysiology", Brain Pathology, vol. 15 (4), 2005, pp. 297-310, (Abstract Only).
Joki et al., "Expression of Cyclooxygenase 2 (COX-2) in Human Glioma and in Vitro Inhibition by a Specific COX-2 Inhibitor, NS-398", Cancer Res, vol. 60, 2000, pp. 4926-4931.
Zhao et al., "Glioma-Derived Mutations in IDH1 Dominantly Inhibit IDH1 Catalytic Activity and Induce HIF-1α", Science, vol. 324 (5924), 2009, pp. 261-265.
Zhao et al., "Hippo Signaling at a Glance", J Cell Sci, vol. 123 (Pt 23), 2010, pp. 4001-4006.
Watanabe et al., "Overexpression of the EGF Receptor and p53 Mutations are Mutually Exclusive in the Evolution of Primary and Secondary Glioblastomas", Brain Pathol, vol. 6 (3), 1996, pp. 217-224.
Waters et al., "Structure of the Tandem MA-3 Region of Pdcd4 Protein and Characterization of Its Interactoins with eIF4A and eIF4G: Molecular Mechanisms of a Tumor Suppressor", The Journal of Biological Chemistry, vol. 286 (19), 2011, pp. 17270-17280.
Watson et al., "*Drosophila* in Cancer Research: the First Fifty Tumor Suppressor Genes", J Cell Sci Suppl, vol. 18, 1994, pp. 19-33.

(56) References Cited

OTHER PUBLICATIONS

Willecke et al., "The Fat Cadherin Acts Through the Hippo Tumor-Suppressor Pathway to Regulate Tissue Size", Curr Biol, vol. 16 (21), 2006, pp. 2090-2100.
Witzenbichler et al., "Cell Biology and Metabolism: Chemotactic Properties of Angiopoietin-1 and -2, Ligands for the Endothelial-Specific Receptor Tyrosine Kinase Tie2", The Journal of Biological Chemistry, vol. 273 (29), 1998, pp. 18514-18521.
Wong et al., "Increased Expression of the Epidermal Growth Factor Receptor Gene in Malignant Gliomas is Invariably Associated With Gene Amplification", Proc Natl Acad Sc USA, vol. 84 (19), 1987, pp. 6899-6903.
Wu et al., "The TEAD/TEF Family Protein Scalloped Mediates Transcriptional Output of the Hippo Growth-Regulatory Pathway", Dev Cell, vol. 14 (3), 2008, pp. 388-398.
Xiao et al., "KIBRA Regulates Hippo Signaling Activity via Interactions with Large Tumor Supressor Kinases", The Journal of Biological Chemistry, vol. 286 (10), 2011, pp. 7788-7796.
Xu et al., "[Hippo Signaling Pathway in Mammals: A New Therapeutic Target for Tumors]", Yi Chuan, vol. 34 (3), 2012, pp. 269-280 (Abstract Only).
Yang et al., "Regulation of Frizzled by Fat-Like Cadherins During Planar Polarity Signaling in the *Drosophila* Compound Eye", Cell, vol. 108 (5), 2002, pp. 675-688.
Yang et al., "Pdcd4 Suppresses Tumor Phenotype in JB6 Cells by Inhibiting AP-1 Transactivation", Oncogene, vol. 22 (24), 2003, pp. 3712-3720 (Abstract Only).
Mao et al., "Planar Polarization of the Atypical Myosin Dachs Orients Cell Divisions in *Drosophila*", Genes & Development, vol. 25 (2), 2011, pp. 131-136.
Yasuda et al., "Downregulation of Programmed Cell Death 4 by Inflammatory Conditions Contributes to the Generation of the Tumor Promoting Microenvironment", Mol Carcinog, vol. 49 (9), 2010, pp. 837-848.
Yokoyama et al., "YAP1 is Involved in Mesothelioma Development and Negatively Regulated by Merlin Through Phosphorylation", Carcinogenesis, vol. 29 (11), 2008, pp. 2139-2146.
Yu et al., "Kibra Functions as a Tumor Suppressor Protein that Regulates Hippo Signaling in Conjunction with Merlin and Expanded", Dev Cell, vol. 18 (2), 2010, pp. 288-299.
Yuan et al., "Yes-Associated Protein (YAP) Functions as a Tumor Suppressor in Breast", Cell Death Differ, vol. 15 (11), 2008, pp. 1752-1759.
Zender et al., "Identification and Validation of Oncogenes in Liver Cancer Using an Integrative Oncogenomic Approach", Cell, vol. 125 (7), 2006, pp. 1253-1267.
Zeng et al., "The Emerging Role of the Hippo Pathway in Cell Contact Inhibition, Organ Size Control, and Cancer Development in Mammals", Cancer Cell, vol. 13 (3), 2008, pp. 188-192.
Zhang et al., "The TEAD/TEF Family of Transcription Factor Scalloped Mediates Hippo Signaling in Organ Size Control", Dev Cell, vol. 14 (3), 2008, pp. 377-387.
Zhang et al., "Clinicopathological Significance of Loss of Heterozygosity and Microsatellite Instability in Hepatocellular Carcinoma in China", World Journal of Gastroenterology, vol. 11 (20), 2005, pp. 3034-3039.
Zhang et al., "Control of Tissue Growth and Cell Transformation by the Salvador/Warts/Hippo Pathway", PLOS One, vol. 7 (2), 2012, e31994.
Zhang et al., "Detection of Differentially Expressed Genes in Human Colon Carcinoma Cells Treated with a Selective COX-2 Inhibitor", Oncogene, vol. 20 (33), 2001, pp. 4450-4456.
Zhao et al., "Inactivation of YAP Oncoprotein by the Hippo Pathway is Involved in Cell Contact Inhibition and Tissue Growth Control", Genes & Development, vol. 21 (21), 2007, pp. 2747-2761.
Zhao et al., "TEAD Mediates YAP-Dependent Gene Induction and Growth Control", Genes & Development, vol. 22 (14), 2008, pp. 1962-1971.
Goodrich et al., "Principles of Planar Polarity in Animal Development", Development, vol. 138, 2011, pp. 1877-1892.
Ardjmand et al., "Fat1 Cadherin Provides a Novel Minimal Residual Disease Marker in Acute Lymphoblastic Leukemia", Hematology, vol. 0 (0), 2013, pp. 1-8.
Valletta et al., "Increased Expression of FAT1 in Hepatocellular Carcinoma Promotes Tumorigenicity", Journal of Hepatology, vol. 52, 2010, pp. S319-S457.
Penas-Prado et al., "Glioblastoma", Handbook of Clinical Neurology, vol. 105 (3), 2012.
Baehring, "Glioblastoma Multiforme—New Approaches to Therapy", The Cancer Journal, vol. 18 (1), 2012.
Fuller et al., "Molecular Classification of Human Diffuse Gliomas by Multidimensional Scaling Analysis of Gene Expression Profiles Parallels Morphology-Based Classification, Correlates with Survival, and Reveals Clinically-Relevant Novel Glioma Subsets", Brain Pathol, vol. 12, 2002, pp. 108-116.
Louis et al., "The 2007 WHO Classification of Tumours of the Central Nervous System", Acta Neuropathol, vol. 114, 2007, pp. 97-109.
Goldbrunner et al., "ECM-Mediated Glioma Cell Invasion", Microscopy Research and Technique, vol. 43, 1998, pp. 250-257.
Gao et al., "Frequent Loss of PDCD4 Expression in Human Glioma: Possible Role in the Tumorigenesis of Glioma", Oncology Reports, vol. 17, 2007, pp. 123-128.
Ozanne et al., "Transcripitional Regulation of Cell Invasion: AP—1 Regulation of a Multigenic Invasion Programme", European Journal of Cancer, vol. 36, 2000, pp. 1640-1648.
Parsons et al., "An Integrated Genomic Analysis of Human Glioblastoma Multiforme", Science, vol. 321, 2008, pp. 1807-1812.
Sadeqzadeh et al., "Dual Processing of FAT1 Cadherin Protein by Human Melanoma Cells Generates Distinct Protein Products", The Journal of Biological Chemistry, vol. 286 (32), 2011, pp. 28181-28191.
Mantovani, "Cancer and Inflammation: A Complex Relationship", Cancer Letters, vol. 267, 2008, pp. 180-181.
Adamson et al., "Glioblastoma Multiforme: A Review of Where We Have Been and Where We Are Going", Expert Opin. Investig. Drugs, vol. 18 (8), 2009, pp. 1061-1083.
Dunne et al., "Molecular Cloning and Tissue Expression of FAT, the Human Homologue of the *Drosophila* Fat Gene That is Located on Chromosome 4q34-q35 and Encodes a Putative Adhesion Molecule", Genomics, vol. 30 (2), 1995, pp. 207-223.
Glantschnig et al., "Mapping of MST1 Kinase Sites of Phosphorylation Activation and Autophosphorylation", J Biol Chem, vol. 277 (45), 2002, pp. 42987-42996.
Goulev et al., "SCALLOPED Interacts with YORKIE, the Nuclear Effector of the Hippo Tumor-supressor Pathway in *Drosophila*", Curr Biol, vol. 18 (6), 2008, pp. 435-441.
Libermann TA et al., "Amplification, Ehanced Expression and Possible Rearrangement of EGF Receptor Gene in Primary Human Brain Tumours of Glial Orgin", Nature, vol. 313 (5998), 1985, pp. 144-147.
Overholtzer M. et al., "Transforming Properties of YAP, a Candidate Oncogene on the Chromosome 11q22 Amplicon", Proc Natl Acad Sci USA, vol. 103 (33), 2006, pp. 12405-12410.
Rottner K. et al., "VASP Dynamics During Lamellipodia Protrusion", Nat Cell Biol, vol. 1 (5), 1999, pp. 321-322.
Saucedo LJ et al., "Filling Out the Hippo Pathway", Nat Rev Mol Cell Biol, vol. 8 (8), 2007, pp. 613-621.
Shaw et al., "The Hippo Pathway Regulates Intestinal Stem Cell Proliferation During *Drosophila* Adult Midgut Regeneration", Development, vol. 137 (24), 2010, pp. 4147-4158.
Ponassi et al., "Expression of the Rat Homologue of the Drosophila Fat Tumour Suppressor Gene", Mech Dev, vol. 80 (2), 1999, pp. 207-212.
Tafani et al., "Pro-lnflmmatory Gene Expression in Solid Glioblastoma Microenvironment and in Hypoxic Stem Cells from Human Glioblastoma", J Neuroinflammation, vol. 8 (32), 2011.
Von Deimling et al., "Astrocytic Gliomas: Characterization on a Molecular Genetic Basis", Recent Results Cancer Res, vol. 135, 1994, pp. 33-42.
Eberstal et al., "Inhibition of Cyclooxygenase-2 Enhances Immunotherapy Against Experimental Brain Tumors", Cancer Immunol Immunother, 2012.

(56) References Cited

OTHER PUBLICATIONS

Von Deimling et al., "Subsets of Glioblastoma Multiforme Defined by Molecular Genetic Analysis", Brain Pathol, vol. 3 (1), 1993, pp. 19-26.
Yang et al., "Tumorigenesis Suppressor Pdcd4 Down-Regulates Mitogen-Activated Protein Kinase Kinase Kinase Kinase 1 Expression to Suppress Colon Carcinoma Cell Invasion", Mol Cell Biol, vol. 26 (4), 2006, pp. 1297-1306.
Dvorak HF, "Tumors: Wounds That Do Not Heal. Similarities Between Tumor Stroma Generation and Wound Healing", N Engl J Med, vol. 315 (26), 1986, 1650-1659.
Salah et al., "WW Domain-Containing Proteins: Retrospectives and the Future", Front Biosci, vol. 17, 2012, pp. 331-348 (reference to follow).
Caskey et al., "Toward a Molecular Classification of the Gliomas: Histopathology, Molecular Genetics, and Gene Expression Profiling", Histol Histopathol, vol. 15 (3), 2000, pp. 971-981(reference to follow).
Stokoe et al., "The PTEN/PI3 Kinase Pathway in Human Glioma", Series Name, Humana Press, 2009, (Springer): New York (reference to follow).
Yin, "Pathway Alterations in Brain Tumors", Series Name, Humana Press, 2009, (Springer): New York (reference to follow).
Fleenor et al., "Involvement of AP-1 in Interleukin-1a-Stimulated MMP-3 Expression in Human Trabecular Meshwork Cells", Invest Ophthalmol Vis Sci, vol. 44 (8), 2003, pp. 3494-3501.
Tsuiji et al., "Bucillamine Mechanism Inhibiting IL-1B-Induced VEGF Production From Fibroblast-Like Synoviocytes", International Immunopharmacology, vol. 7, 2007, pp. 1569-1576.
Funari et al., "Genetics and Malignant Progression of Human Brain Tumors", Cancer Surv, vol. 25, 1995, pp. 233-275 (Abstract Only).
Funari et al., "Molecular Biology of Malignant Degeneration of Astrocytoma", Pediatr Neurosurg, vol. 24 (1), 1996, pp. 41-49 (Abstract Only).
Funari et al., "Malignant Astrocytic Glioma: Genetics, Biology, and Paths to Treatment", Genes & Development, vol. 21 (21), 2007, pp. 2682-2710.
Garoia et al., "Cell Behaviour of Drosophila Fat Cadherin Mutations in Wing Development", Mechanisms of Development, vol. 94 (1-2), 2000, pp. 95-109.
Genevet et al., "Kibra is a Regulator of the Salvador/Warts/Hippo Signaling Network", Dev Cell, vol. 18 (2), 2010, pp. 300-308.
Germano et al., "Cytokines as a key Component of Cancer-Related Inflammation", Cytokine, vol. 43 (3), 2008, pp. 374-379 (Abstract Only).
Greenhough et al., "The Cox-2/PGE2 Pathway: Key Roles in the Hallmarks of Cancer and Adaptation to the Tumour Microenvironment", Carcinogenesis, vol. 30 (3), 2009, pp. 377-386.
Hao et al., "Mechanisms of Signal Transduction: Tumor Suppressor LATS1 is a Negative Regulator of Oncogene YAP", The Journal of Biological Chemistry, vol. 283 (9), 2008, pp. 5496-5509.
Hara et al., "Cyclooxygenase-2 and Inducible Nitric Oxide Synthase Expression in Human Astrocytic Gliomas: Correlation With Angiogenesis and prognostic Significance", Acta Neuropathol, vol. 108 (1), 2004, pp. 43-48 (Abstract Only).
Harris et al., "Reduced Risk of Human Lung Cancer by Selective Cyclooxygenase 2 (Cox-2) Blockade: Results of a Case Control Study", International Journal of Biological Sciences, vol. 3 (5), 2007, pp. 328-334.
Harris, "Cyclooxygenase-2 (Cox-2) and the Inflammogenesis of Cancer", Subcell Biochem, vol. 42, 2007, pp. 93-126 (Abstract Only).
Harris et al., "Cancer Chemoprevention by Cyclooxygenase 2 (Cox-2) Blockade: Results of Case Control Studies", Subcell Biochem, vol. 42, 2007, pp. 193-212 (Abstract Only).
Harvey et al., "The Salvador-Warts-Hippo Pathway—an Emerging Tumour0 Suppressor Network", Nat Rev Cancer, vol. 7 (3), 2007, pp. 182-191 (Abstract Only).
Harvey et al., "The Hippo Pathway", Cold Spring Harbor Perspectives in Biology, 2012, pp. 1-4.
McNeil et al., "When Pathways Collide: Collaboration and Connivance Among Signalling Proteins in Development", Molecular Cell Biology, vol. 11, 2010, pp. 404-413.
Strutt et al., "Cleavage and Secretion is Not Required for Four-Jointed Function in *Drosophila* Patterning", Research Article, vol. 131 (4), 2003, pp. 881-890.
Herseth et al., "Role of IL-1 Beta and COX2 in Silica-Induced IL-6 Release and Loss of Pneumocytes in Co-Cultures", Toxicol in Vitro, vol. 23 (7), 2009, pp. 1342-1353 (Abstract Only).
Hill et al., "Molecular Genetics of Brain Tumors", Arch Neurol, vol. 56 (4), 1999, pp. 439-441.
Ohgaki et al., "Genetic Pathways to Primary and Secondary Glioblastoma", The American Journal of Pathology, vol. 170 (5), 2007, pp. 1445-1453.
Ohgaki et al., "Genetic Pathways to Glioblastoma: A Population-Based Study", Cancer Research, vol. 64 (19), 2004, pp. 6892-6899.
Hong et al., The YAP and TAZ Transcription Coactivators: Key Downstream Effectors of the Mammalian Hippo Pathway, Semin Cell Dev Biol, 2012.
Hou et al., "The Fat1 Cadherin Integrates Vascular Smooth Muscle Cell Growth and Migration Signals", The Journal of Cell Biology, vol. 173 (3), 2006, pp. 417-429.
Hou et al., "Atrophin Proteins: Interact With the Fat1 Cadherin and Regulate Migration and Orientation in Vascular Smooth Muscle Cells", The Journal of Biological Chemistry, vol. 284 (11), 2009, pp. 6955-6965.
Huang et al., "The Hippo Signaling Pathway Coordinately Regulates Cell Proliferation and Apoptosis by Inactivating Yorkie, the *Drosophila* Homolog of YAP", Cell, vol. 122 (3), 2005, pp. 421-434.
Hull et al., "Cyclooxygenase 2 is Up-Regulated and Localized to Macrophages in the Intestine of Min Mice", British Journal of Cancer, vol. 79 (9-10), 1999, pp. 1399-1405.
Hwang et al., "Cyclin E in Normal and Neoplastic Cell Cycles", Oncogene, vol. 24 (17), 2005, pp. 2776-2786.
Oh et al., "In Vivo Analysis of Yorkie Phosphorylation Sites", Oncogene, 2009, pp. 1916-1927.
Oh et al., "Role of the Tumor Suppressor RASSF1A in Mst1-Mediated Apoptosis", Cancer Research, vol. 66 (5), 2006, pp. 2562-2569.
Nakaya et al., "Identification of Homozygous Deletions of Tumor Suppressor Gene FAT in Oral Cancer using CGH-Array", Oncogene, vol. 26 (36), 2007, pp. 5300-5308.
Irvine, "Integration of Intercellular Signaling Through the Hippo Pathway", Semin Cell Dev Biol, vol. 23 (7), 2012, pp. 812-817.
James et al., "Molecular Genetic Aspects of Glilal Tumour Evolution", Cancer Surv, vol. 9 (4), 1990, pp. 631-644 (Abstract Only).
Jaros et al., "Prognostic Implications of P53 Protein, Epidermal Growth Factor Receptor, and Ki-67 Labelling in Brain Tumors", Br. J. Cancer, vol. 66 (2), 1992, pp. 373-385.
Kanu et al., "Glioblastoma Multiforme: A Review of Therapeutic Targets", Exper Opin. Ther. Targets, vol. 13 (6), 2009, pp. 701-718 (Abstract Only).
Karamouzis et al., "The Activator Protein-1 Transcription Factor in Respiratory Epithelium Carcinogenesis", Molecular Cancer Research, vol. 5 (2), 2007, pp. 109-120.
Karlborn et al., "Loss of Heterozygosity in Malignant Gliomas Involves at Least Three Distinct Regions on Chromosome 10", Hum. Genet, vol. 92 (2), 1993, pp. 169-174 (Abstract Only).
Katoh et al., "Comparative Integromics on FAT1, FAT2, FAT3, and FAT4", Int J Mol Med, vol. 18 (3), 2006, pp. 523-528 (Abstract Only).
Lin et al., "YAP Regulates Neuronal Differentiation Through Sonic Hedgehog Signaling Pathway", Exp Cell Res, 2012 (Abstract Only).
Knight et al., "TEADI and c-Cbl are Novel Prostate Basal Cell Markers That Correlate With Poor Clinical Outcome in Prostate Cancer", Br J Cancer, vol. 99 (11), 2008, pp. 1849-1858.
Visnyei et al., "A Molecular Screening Approach to Identify and Characterize Inhibitors of Glioblastoma Stem Cells", Molecular Cancer Therepy, 2011, pp. 1818-1828.

(56) References Cited

OTHER PUBLICATIONS

Kwaepila et al., "Immunohistological Localisation of Human FAT1 (hFAT) Protein in 326 Breast Cancers. Does this Adhesion Molecule Have a Role in Pathogeneis?", Pathology, vol. 38 (2), 2006, pp. 125-131 (Abstract Only).

Lai et al., "Control of Cell Proliferation and Apoptosis by Mom as Tumor Suppressor, Mats", Cell, vol. 120 (5), 2005, pp. 675-685.

Kleihues et al., "World Health Organization Classification of Tumors", Cancer, vol. 88 (12), 2000, pp. 2887.

Lankat-Buttgereit et al., "The Tumour Sppressor Pdcd4: Recent Advances in the Elucidation of Function and Regulation", Biol Cell, vol. 101 (6), 2009, pp. 309-317 (Abstract Only).

Lankat-Buttgereit et al., "Programmed Cell Death Protein 4 (pdcd4): a Novel Target for Antineoplastic Therapy?", Biol Cell, vol. 95 (8), 2003, pp. 515-519 (Abstract Only).

Leaner et al., "AP-1 Complexes Containing cJun and JunB Cause Cellular Transformation of Rat1a Fibroblasts and Share Transcriptional Targets", Oncogene, vol. 22 (36), 2003, pp. 5619-5929.

Libermann et al., "Amplificatoin and Overexpression of the EGF Receptor Gene in Primary Human Glioblastomas", J Cell Sci Suppl, vol. 3, 1985, pp. 161-172 (Abstract Only).

Lei et al., "TAZ Promotes Cell Proliferation and Epithelial-Mesenchymal Transition and Is Inhibited by the Hippo Pathway", Molecular and Cellular Biology, vol. 28 (7), 2008, pp. 2426-2436.

Leaner et al., "Inhibition of AP-1 Transcriptional Activity Blocks the Migration, Invasion, and Experimental Metastasis of Murine Osteosarcoma",Am J Pathol, vol. 174 (1), 2009, pp. 265-275.

Liu et al., "Regulators of Mammalian Hippo Pathway in Cancer", Biochim Biophys Acta, vol. 1826 (2), 2012, pp. 357-364, (Abstract Only).

Liu et al., "An Update on Targeting Hippo-YAP Signaling in Liver Cancer", Expert Opin Ther Targets, vol. 16 (3), 2012, pp. 243-247, (Abstract Only).

Lu et al., "MicroRNA-21 Promotes Cell Transformation by Targeting the Programmed Cell Death 4 Gene", Oncogene, vol. 27 (31), 2008, pp. 4373-4379, (Abstract Only).

Mahoney et al., "The Fat Tumor Suppressor Gene in Drosophila Encodes a Novel Member of the Cadherin Gene Superfamily", Cell, vol. 67 (5), 1991, pp. 853-868, (Abstract Only).

Mao et al., "Dachs: an Unconventional Myosin That Functions Downstream of Fat to Regulate Growth, Affinity and Gene Expression in *Drosophila*", Research Article, Development, vol. 133 (13), 2006, pp. 2539-2551.

Moeller et al., "Protocadherin FAT1 Binds Ena/VASP Proteins and is Necessary for Actin Dynamics and Cell Polarization", Embo J, vol. 23 (19), 2004, pp. 3769-3779.

Mueller et al., "Friends or Foes—Bipolar Effects of the Tumour Stroma in Cancer", Nat Rev Cancer, vol. 4 (11), 2004, pp. 839-849.

Maxwell et al., "Coexpression of Platelet-Derived Growth Factor (PDGF) and PDGF-Receptor Genes by Primary Human Astrocytomas May Contribute to Their Development and Maintenance", J Clin Invest, vol. 86 (1), 1990, pp. 131-140.

Mazzoleni et al., "Gliomagenesis: A Game Played by Few Players or a Team Effort?", Front Biosci (Elite Ed), vol. 4, 2012, pp. 205-213.

Nakada et al., "Aberrant Signaling Pathways in Glioma", Cancers, vol. 3 (3), 2011, pp. 3242-3278.

Nieves-Alicea et al., "Programmed Cell Death 4 Inhibits Breast Cancer Cell Invasion by Increasing Tissue Inhibitor of metalloproteinases-2 Expression", Breast Cancer Res Treat, vol. 114 (2), 2009, pp. 203-209.

Nishikawa et al., "Human FAT1 Cadherin Controls Cell Migration and Invasion of Oral Squamous Cell Carcinoma Through the Localization of β-Catenin", Oncol Rep, vol. 26 (3), 2011, pp. 587-592.

Vitkovic et al., "Inflammatory" Cytokines: Neuromodulators in Normal Brain?, J Neurochem, vol. 74 (2), 2000, pp. 457-471.

Ohgaki et al., "Genetic Alterations and Signaling Pathways in the Evolution of Gliomas", Cancer Sci, vol. 100 (12), 2009, pp. 2235-2241.

Oka et al., "Mst2 and Lats Kinases Regulate Apoptotic Function of Yes Kinase-Associated Protein (YAP)", J Biol Chem, vol. 283 (41), 2008, pp. 27534-27546.

Opdenakker et al., "The Countercurrent Principle in Invasion and Metastasis of Cancer Cells. Recent Insights on the Roles of Chemokines", Int J Dev Biol, vol. 48 (5-6), 2004, pp. 519-527.

Philip et al., "Inflammation as a Tumor Promoter in Cancer Induction", Semin Cancer Biol, vol. 14 (6), 2004, pp. 433-439, (Abstract Only).

Porta et al., "Cellular and Molecular Pathways Linking Inflammation and Cancer", Immunobiology, vol. 214 (9-10), 2009, pp. 761-777, (Abstract Only).

Reardon et al., "Recent Advances in the Treatment of Malignant Astrocytoma", J Clin Oncol, vol. 24 (8), 2006, pp. 1253-1265.

Reddy et al., "The Fat and Warts Signaling Pathways: New Insights Into Their Regulation, Mechanism and Conservation", Development, vol. 135 (17), 2008, pp. 2827-2838.

Udan et al., "Hippo Promotes Proliferation Arrest and Apoptosis in the Salvador/Warts Pathway", Nature Cell Biology, vol. 5 (10), 2003, pp. 1-6, 914-920.

Santhanam et al., "Pdcd4 Repression of Lysyl Oxidase Inhibits Hypoxia-Induced Breast Cancer Cell Invasion", Ocogene, vol. 29 (27), 2010, pp. 3921-3932.

Sareddy et al., "The Nonsteroidal Anti-Inflammatory Drug Celecoxib Suppresses the Growth and Induces Apoptosis of Human Glioblastoma Cells Via the NF-kB Pathway", J Neurooncol, vol. 106 (1), 2012, pp. 99-109, (Abstract Only).

Schmid et al., "Inflammation-Induced Loss of Pdcd4 is Mediated by Phosphorylation-Dependent Degradation", Carcinogenesis, vol. 32 (10), 2011, pp. 1427-1433.

Schwechheimer et al., "EGFR Gene Amplification—Rearrangement in Human Glioblastomas", Int J Cancer, vol. 62 (2), 1955, pp. 145-148, (Abstract Only).

See et al., "Anaplastic Astrocytoma: Diagnosis, Prognosis, and Management", Semin Oncol, vol. 31 (5), 2004, pp. 618-634, (Abstract Only).

Seidel et al., "Frequent Hypermethylation of MST1 and MST2 in Soft Tissue Sarcoma", Mol Carcinog, vol. 46 (10), 2007, pp. 865-871, (Abstract Only).

Settakorn et al., "FAT, E-Cadherin, β Catenin, HER 2/neu, Ki67 Immunoexpression, and Histological Grade in Intrahepatic Cholangiocarinoma", J Clin Pathol, vol. 58 (12), 2005, pp. 1249-1254.

Sharma et al., "Pleomorphic Xanthoastrocytoma—a Clinico-Pathological Review", Neurol Neurochir Pol, vol. 45 (4), 2011, pp. 379-386, (Abstract Only).

Sharma et al., "COX-2 Regulates the Proliferation of Glioma Stem Like Cells", Neurochem Int, vol. 59 (5), 2011, pp. 567-571, (Abstract Only).

Sheehan et al., "The Relationship Between Cyclooxygenase-2 Expression and Colorectal Cancer", Jama, vol. 282 (13), 1999, pp. 1254-1257, (Abstract Only).

Shen et al., "The AP-1 Transcription Factor Regulates Breast Cancer Cell Growth Via Cyclins and E2F Factors", Oncogene, vol. 27 (3), 2008, pp. 366-377, (Abstract Only).

Shono et al., "Cyclooxygenase-2 Expression in Human Gliomas: Prognostic Significance and Molecular Correlatoins", Cancer Res, vol. 61 (11), 2001, pp. 4375-4381.

Silva et al., "The Tumor-Suppressor Gene fat Controls Tissue Growth upstream of Expanded in the Hippo Signaling Pathway", Curr Biol, vol. 16 (21), 2006, pp. 2081-2089.

Sonoshita et al., "Cyclooxygenase-2 Expression in Fibroblasts and Endothelial Cells of Intestinal Polyps", Cancer Res, vol. 62 (23), 2002, pp. 6846-6849.

Staley et al., "Hippo Signaling in *Drosophila*: Recent Advances and Insights", Dev Dyn, vol. 241 (1), 2012, pp. 3-15.

Vitkovic et al., "Cytokine signals propagate through the brain", Mol Psychiatry, vol. 5 (6) pp. 604-615. 2000.

Strutt et al., "Asymmetric Localisation of Planar Polarity Proteins: Mechanisms and Consequences", Semin Cell Dev Biol, vol. 20 (8), 2009, pp. 957-963, (Abstract Only).

Takahashi et al., "Down-Regulation of LATS1 and LATS2 mRNA Expression by PRomoter Hypermethylation and Its Association

(56) References Cited

OTHER PUBLICATIONS with Biologically Aggressive Phenotype in Human Breast Cancers", Clin Cancer Res, vol. 11 (4), 2005, pp. 1380-1385.

Tanoue et al., "New Insights Into Fat Cadherins", Journal of Cell Science, vol. 118 (Pt 11), 2005, pp. 2347-2353.

Tanoue et al., "Mammalian Fat1 Cadherin Regulates Actin Dynamics and Cell-Cell Contact", J Cell Biol, vol. 165 (4), 2004, pp. 517-528.

Tapon et al., "Salvador Promotes Both Cell Cycle Exit and Apoptosis in *Drosophila* and is Mutated in Human Cancer Cell Lines", Cell, vol. 110 (4), 2002, pp. 467-478.

Tewari et al., "Involvment of TNFα-Induced TLR4-NF-kB and TLR4-HIF-1α Feed-Forward Loops in the Regulation of Inflammatory Responses in Glioma", J Mol Med (Berl), vol. 90 (1), 2012, pp. 67-80, (Abstract Only).

Thaker et al., "Identification of Survival Genes in Human Glioblastoma Cells by Small Interfering RNA Screening", Mol Pharmacol, vol. 76 (6), 2009, pp. 1246-1255.

Thaker et al., "Molecularly Targeted Therapies for Malignant Glioma: Rationale for Combinatorial Strategies", Expert Rev Neurother, vol. 9 (12), 2009, pp. 1815-1836.

Thomas et al., "The Roles of the Cadherins Fat and Dachsous in Planar Polarity Specification in *Drosophila*", Dev Dyn, vol. 241 (1), 2012, pp. 27-39.

Van Meir et al., "Exciting New Advances in Neuro-Oncology", The Avenue to a Cure for Malignant Glioma, CA Cancer J Clin, vol. 60 (3), 2010, pp. 166-193.

Varelas et al., "The Hippo Pathway Regulates Wnt/B-Catenin Signaling", Development, vol. 18 (4), 2010, pp. 579-591.

Villano et al., "Four-Jointed is Required for Intermediate Growth in the Proximal-Distal Axis in *Drosophila*", Development, vol. 121 (9), 1995, pp. 2767-2777.

Ozanne et al., "Transcriptional Regulation of Cell Invasion: AP-1 Regulation of a Multigenic Invasion Programme", European Journal of Cancer, vol. 36 (200) pp. 1640-1648.

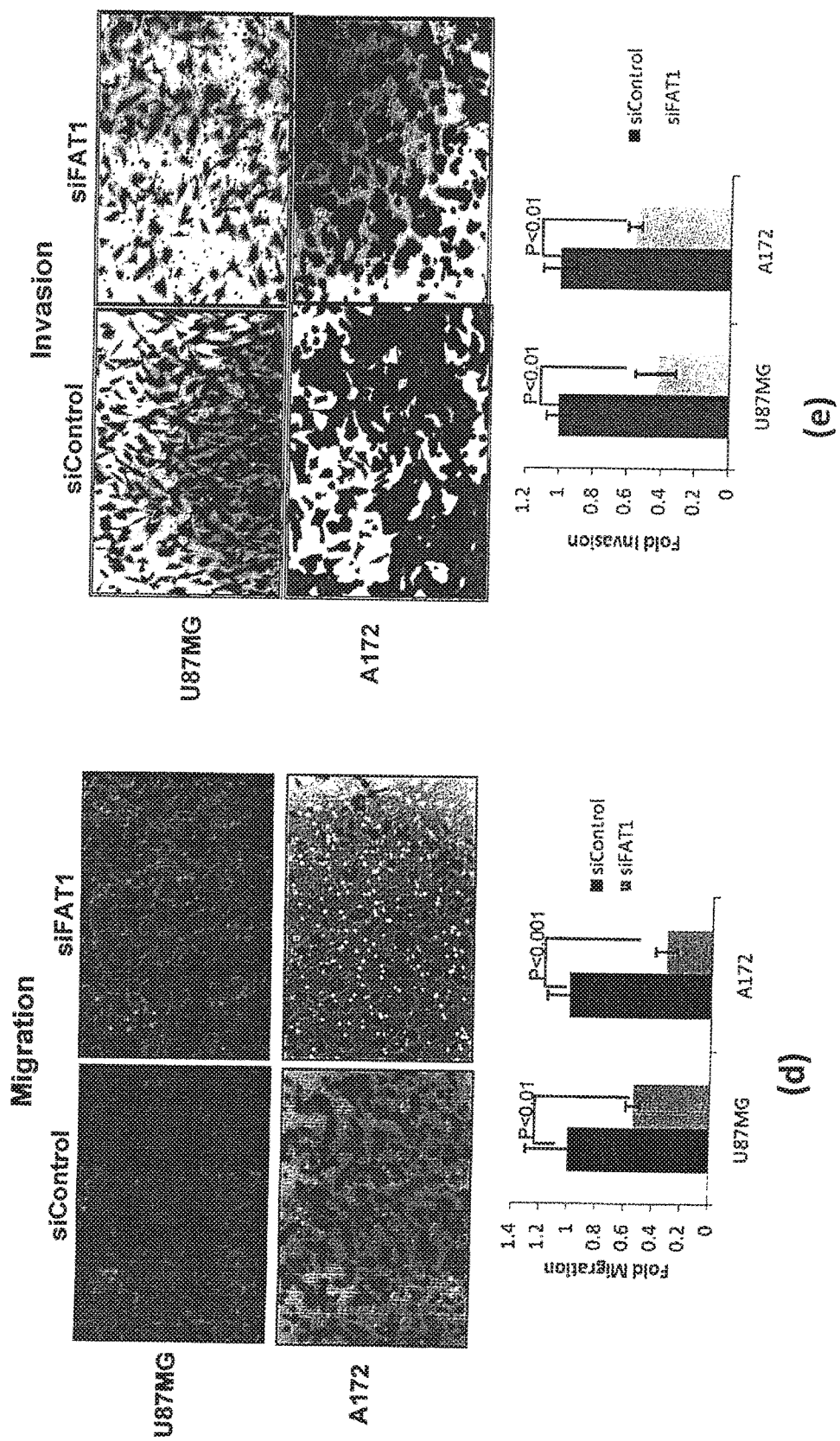

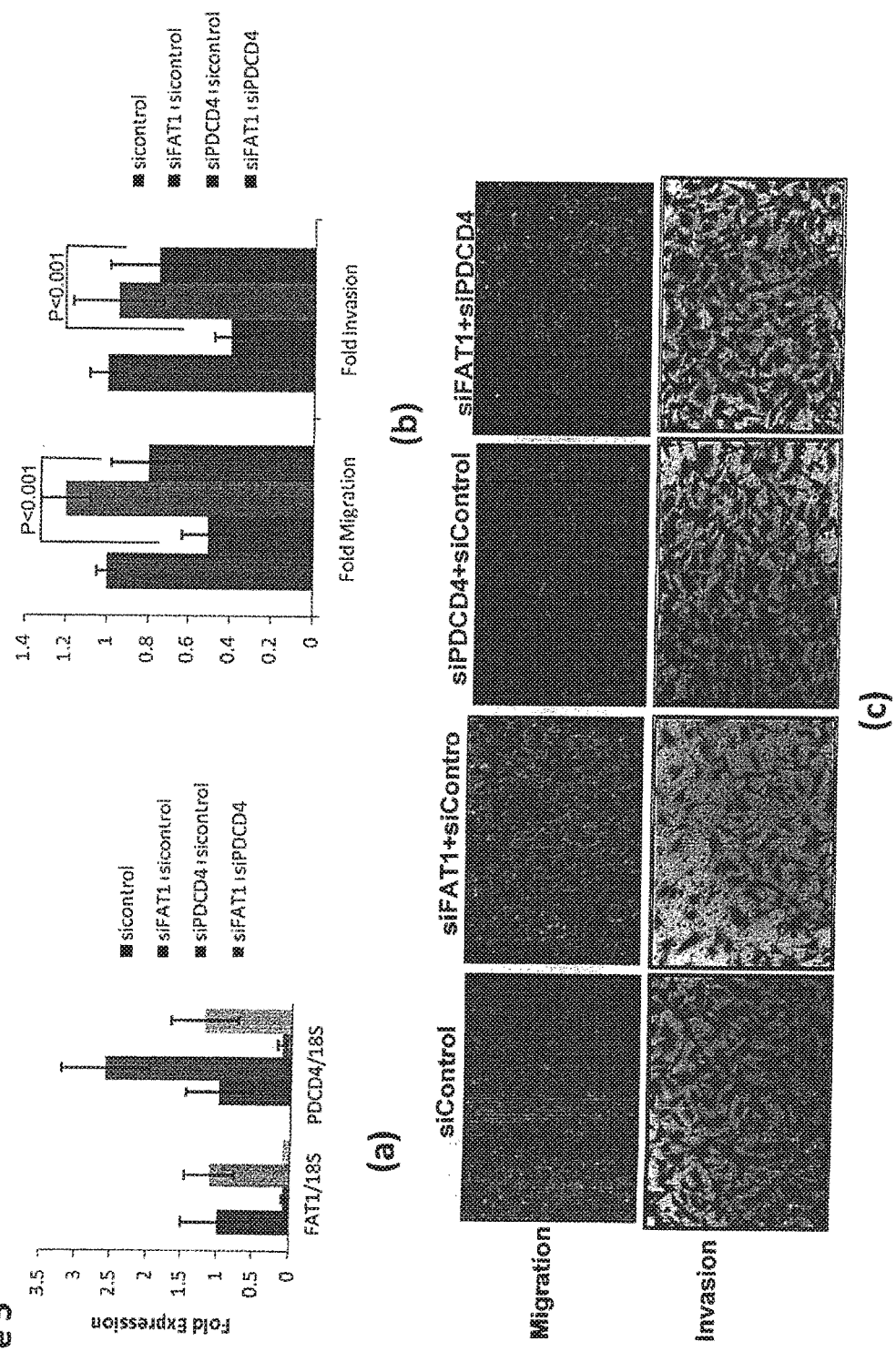

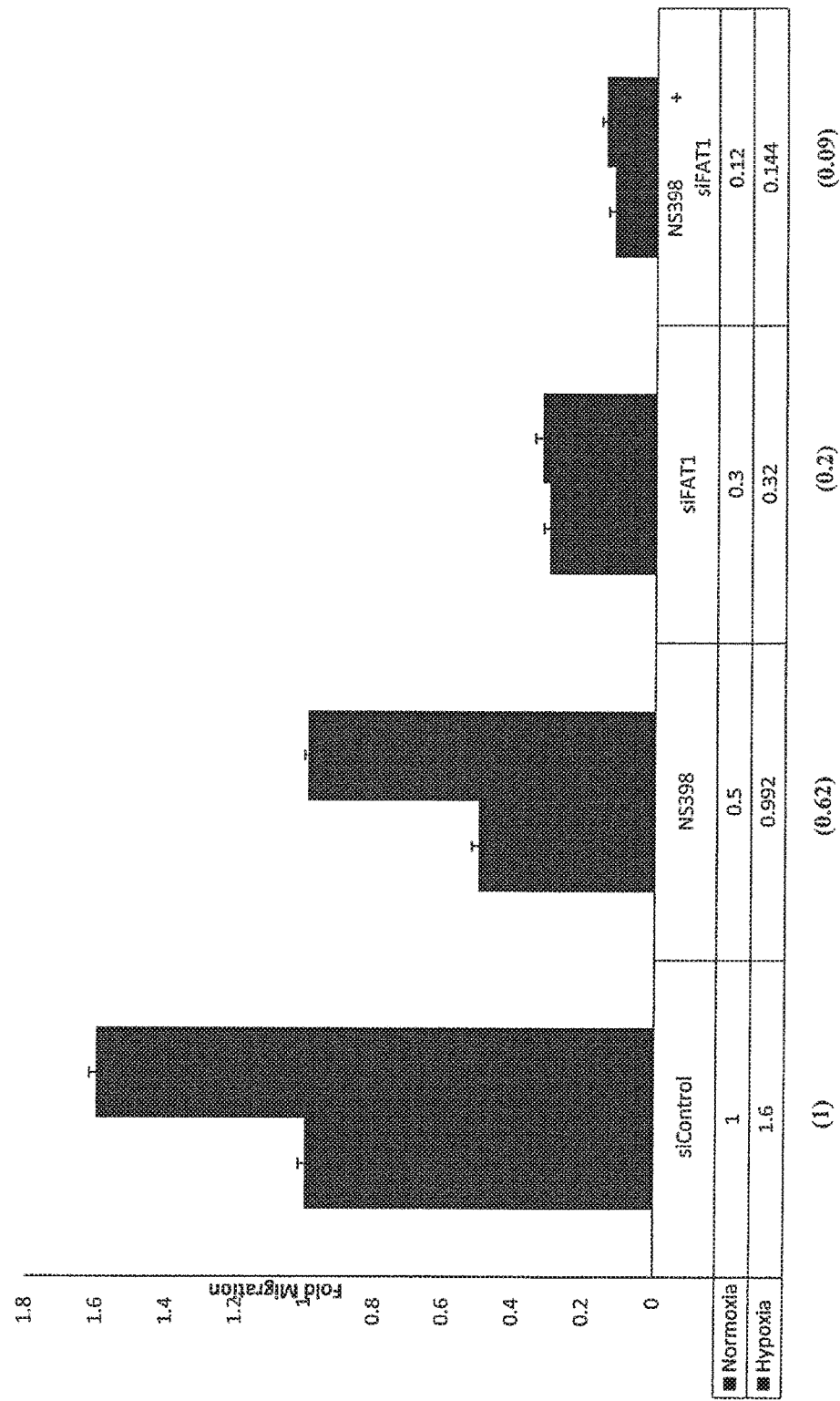

FAT1 GENE IN CANCER AND INFLAMMATION

RELATED APPLICATIONS

This application is a Continuation-In-Part under 35 USC §120 of International Application PCT/IB2013/050086, filed in WIPO on Jan. 4, 2013. This application claims priority under 35 USC §119 of Indian application 45/DEL/2012, filed on Jan. 5, 2012. All of the above applications are hereby incorporated by reference.

SEQUENCE LISTING

The instant application contains a Sequence Listing that has been submitted in ASCII format via EFS-Web and is hereby incorporated by reference in its entirety. Said ASCII copy, created on Jun. 27, 2014 is named 20140703_seqlist_40039020001.txt and is 34.3 KB in size.

FIELD OF THE INVENTION

The present invention relates generally to the field of molecular biology. More specifically, the invention relates to the field of cancer biology and inflammation.

BACKGROUND OF THE INVENTION

Cancer and inflammatory diseases are multifactorial diseases and different mode of therapies are being exploited and attempted. Glioblastomas (GBM) are the most frequent and most malignant form of brain tumors. Tumor angiogenesis, invasiveness and rapid growth go in concert in GBM. The tumor microenvironment exhibits expression of pro-inflammatory molecules that promote migration and invasion of tumor cells. There is increasing evidence of the role of the pro-inflammatory molecules in making glioma and other tumors more aggressive and resistant to chemo- and/or radio-therapy.

Common pathways may promote tumor invasiveness and expression of pro-inflammatory molecules in GBM. Of these COX-2 and cytokines like IL1β, IL6 are the known mediators of both the processes. However the therapeutic translation of this knowledge has been limited. FAT1, a member of the cadherin gene family, is the human homologue of the *Drosophila* fat. Fat in *D. melanogaster* is a known tumor suppressor gene acting via the Salvador-Warts-Hippo (SWH) signaling pathway, and is essential for controlling cell proliferation during development and regulating planer cell, and any defect in the expression of fat would lead to tumor development. In *Drosophila*, fat is an upstream regulator of the SWH pathway. The signaling molecules of SWH pathway are conserved in human but the role of FAT1 as an apical regulator has not yet been established. Disruption of fat causes imaginal disc tumors in *Drosophila*. The fat gene was first discovered in *Drosophila* followed by the identification of its orthologue in man, rat, mouse and zebrafish etc.

The expression profile of FAT1 has been studied in human fetal and adult tissues. FAT1 in human is reported to be localized to region of chromosome 4q35. The expression of FAT1 peaks in embryonic stages and diminishes later in adult life. High levels of FAT1 transcripts were found in kidney, lungs, and eye epithelia, and were down regulated in the corresponding adult tissues, indicating the role of FAT1 in organ development. FAT1 is also known to have a role in cell polarity and migration. FAT1 is found to be involved in the glomeruli as a slit junction adhesion molecule and have been found to be interacting with atropine in regulating cell orientation and migration. FAT1 is up-regulated in cell migration, induces cellular process formation when overexpressed, and is necessary for efficient wound healing. FAT1 was found to be localized at filipodial tips, lamellipodial edges, and cell-cell boundaries, overlapping with dynamic actin structures.

Very few reports are available on the role of FAT1 in human cancer. A study from the inventors has shown low expression of and loss of heterozygosity (LOH) at the FAT1 locus in the gliomas. Studies have shown altered expression of FAT1 in different cancers but the exact role of FAT1 has not been fully elucidated, even the mechanism of action of FAT1 in mammalian epithelial cell migration is not fully understood. The signaling cascades and cellular processes through which FAT1 acts in different contexts are still being elucidated and very few functional studies are available on the role of FAT1 in human cancers, including GBM. However the main focus of FAT1 so far in the literature has been as a tumor suppressor gene.

There are studies showing LOH and/or deletion of the chromosome 4q34-35 region in many tumors including gliomas but the FAT1 gene itself has not been analyzed and implicated. LOH/alterations in the chromosomal 4q34-35 region was found in grade IV gliomas using microsatellite markers, Small Cell Lung Carcinoma, hepatocellular carcinoma and cervical carcinoma etc. In all these LOH studies, a significant association of 4q34-q35 region with increased risk of progression to higher grade or with the malignancy of the tumors was suggested. Since the FAT1 gene is located in this region it appears to have an important role to play in the development and progression of these tumors.

A positional cloning strategy, combined with association analysis has provided evidence that FAT1 confers susceptibility to bipolar disorder.

It is important to note that all the previous literature has concentrated on FAT1 as a tumor suppressor gene and there is no literature on FAT1 promoting either tumourigenesis or inflammation or the link between the two.

The signaling cascade(s) being regulated by FAT1 gene and the function of FAT1 gene in human cancers including GBM is not known. Therefore, development of the present invention has helped to uncover the precise role of FAT1 gene in inflammation and tumors, including GBM.

Till now, targeting pro-inflammatory molecules or related pathways as therapeutic strategies to prevent or treat cancers has had a limited success and there is considerable interest in focusing on such molecules. The transmembrane molecule, FAT1 is thus a novel target for therapeutic intervention in cancer and inflammation as well as the link between the two processes.

DISCLOSURE OF THE INVENTION

The present disclosure demonstrates the role of FAT1, a transmembrane protein, in linking the neoplastic phenotype and inflammatory mediators in cancer cells.

The present disclosure further demonstrates that FAT1 can upregulate some features of tumorigenesis and can function as an oncogene under certain conditions and can also influence the expression of mediators of inflammation.

The present invention demonstrates for the first time that FAT1 plays an important role in modulating PDCD4 expression, which in turn regulates AP1 dependent transcription, controls processes crucial for migration and invasion in cancer cells, controls induction of a pro-inflammatory microenvironment in cancer cells. The invention illustrates a link between inflammation and cancer in cells or in a subject. This work highlights the importance of FAT1 in the induction of the cellular pathways of migration and invasion, proteolysis of the ECM and the expression of pro-inflammatory molecules leading to a favorable microenvironment for tumor and cancer progression.

The present invention also provides the use of FAT1 in regulating neoplastic phenotypes and genotypes including invasiveness and inflammatory microenvironment of the cancer cells by acting as a novel apical regulator of a signaling pathway by affecting the AP1 transcriptional activity, affecting the property of both cell migration and invasion and at the same time affecting the expression of inflammatory modulators.

The present invention by establishing a novel cell signaling pathway that regulate PDCD4 and AP1 mediated transcription—thereby regulating the general inflammatory mediators, IL1β, COX-2, IL6 and prostaglandins—also provides a way of beneficially intervening in pathologies that are intrinsically inflammatory and may not have any link with cancer.

This novel work has not only elucidated the role of FAT1 in regulating some the key invasive properties of a cancer cell and the expression of inflammatory molecules in the cell by being a novel mediator of cell signaling, but this also points to the utilization of the FAT1 modulation as a therapeutic targets in both cancer and inflammatory diseases. In addition, the present elucidation of the link between cancer and inflammation provides insights on how the inflammatory processes are controlled. Hence they provide a basis for the control of intrinsic inflammatory pathology as well.

BRIEF DESCRIPTION OF THE DRAWINGS

The accompanying drawings illustrate embodiments of the invention and, together with the description, serve to explain the invention. These drawings are offered by way of illustration and not by way of limitation.

(A) FAT1 expression was checked in six glioma cell lines by q-PCR, out of which grade IV glioma cell lines U87MG, A172, U373MG and T98G were found to have high FAT1 expression while grade III glioma cell lines GOS3 and SW1088 had low FAT1 expression. 18s was used as internal control. (B) Knockdown of FAT1 in U87MG and A172 cell lines (72 hrs post transfection) was confirmed by q-PCR using FAT1 specific primers. ≥90% down-regulation of FAT1 mRNA in siFAT1 cells was observed as compared to siControl treated cells. 18S was used as internal control; all experiments were done in triplicates and repeated thrice. (C) Distinct phenotypic changes (72 hrs post transfection) were observed in U87MGsiFAT1 and A172siFAT1 cells as compared to siControl cells. siFAT1 treated cells were spindle shaped or rounded, scattered and had reduced cell-cell interaction. (D,E) FAT1 knockdown inhibited cell migration and invasion in U87MGsiFAT1 as well as A172siFAT1 cells as compared to siControl cells. A modified Boyden chamber assay/matrigel assay was performed for 24 hrs (72 hrs post-transfection) to assess cell migration and invasion. Cells migrated across membrane or invaded through matrigel were fixed, stained and were counted in five different fields and means were calculated. The number of cells that migrated or invaded in siFAT1 cells were normalized against number of cells that migrated in siControl cells. Each value is expressed as mean±standard deviation. Each experiment was done in triplicate and repeated twice. Significant differences were observed in siFAT1 treated cells as compared to siControl cells as determined by Student's t test. Mock: lipofactamin treated cells; siControl: Invitrogen universal medium GC control siRNA treated cells and siFAT1: FAT1 specific siRNA (Invitrogen) treated cells.

Figure 2:
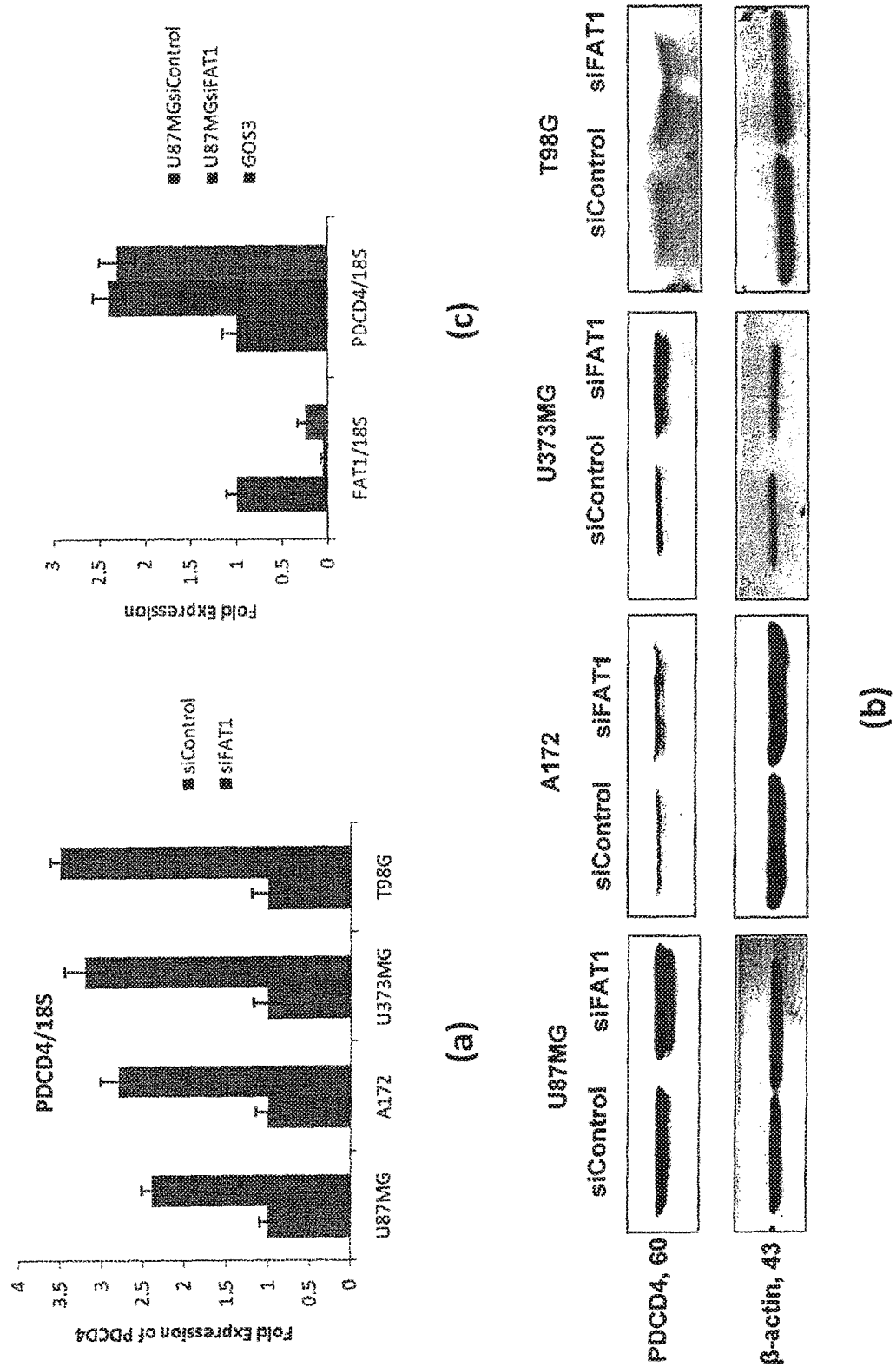

FIGS. 2A to 2C: Knockdown of FAT1 upregulated PDCD4 expression; (A) PDCD4 mRNA expression as assessed by q-PCR (72 hrs post siRNA transfection) was found to be increased by more than two fold in all the GBM cell lines (U87MG, A172, U373 and T98) analysed after FAT1 knockdown as compared to their respective siControl cells. 18s was used as internal control (B) Similarly PDCD4 protein level was also found to be increased in the above GBM cell lines after FAT1 knockdown as compared to respective siControl cells as assessed by Western blot analysis. β-actin was used as loading control. (C) GOS3 (WHO grade III glioma) cell line with low endogenous FAT1 was found to have high PDCD4 mRNA expression which was comparable to U87MGsiFAT1 treated cells.

FIGS. 3A to 3D: Inhibition of AP-1 transcriptional activity after FAT1 knockdown (A) FAT1 knockdown in U87MG cells up-regulated PDCD4 expression which in turn inhibits phosphorylation of c-jun. Western blot was performed on cell lysates from U87MGsiFAT1 and siControl cells with phospho-c-jun (Ser63) and c-jun antibodies. There was significant reduction in the p-c-jun level. β-actin antibody as loading control. (B) The mRNA level of c-jun was found to be reduced by two folds after FAT1 knockdown. A reduction in the total c-jun protein observed after FAT1 knockdown could be due to decreased positive autoregulation of c-jun expression by AP-1 as well as the ubiquitination and rapid degradation of the unphosphorylated c-jun. (C,D) AP-1 luciferase assay was done to assess AP-1 transcriptional activity. U87MG cells were independently transfected with siFAT1 or siPDCD4 and siControl. After 24 hrs, cells were transfected with 1 μg of AP-1 reporter plasmid, along with 50 ng of pRL-TK (Renilla luciferase) control plasmid. The luciferase activity was measured after 48 hrs. The luciferase activity with control siRNA is designated as 100% and the difference calculated, significant difference in siFAT1 and siPDCD4 treated cells ($p<0.01$ and $p<0.05$ respectively) was observed compared with siControl cells, as determined by Student's t test. The experiment was repeated thrice and results are expressed as mean±standard deviation.

FIGS. 4A to 4E: Decrease in COX-2 expression and cytokines synthesis after FAT1 knockdown; (A) Expression of COX-2 and cytokines were found to be decreased after FAT1 knockdown. q-PCR was done to measure the mRNA expression of COX-2, IL6 and IL1 β and almost 10 fold reduction was observed in U87MGsiFAT1 cells as compared to siControl cells. 18s was used as internal control. (B) FAT1 knockdown was found to inhibit COX-2 protein expression. Western blot for indicated cells showed decreased COX-2 expression after FAT1 knockdown. β-actin was used as loading control. (C) PGE2 assay was done to quantify the production of PGE2 after FAT1 knockdown. Synthesis of enzymatic product of COX-2, PGE2 was decreased significantly by >2 fold in U87MGsiFAT1 cells as compared to siControl cells. Experiment was done in triplicate and repeated twice. Each value is expressed as mean±standard deviation. Significant difference ($p<0.01$) was observed as determined by Student's t test. (D) COX-2 luciferase assay was done in U87MGsiControl and U87siFAT1 cells after treatment with either 0.1% DMSO or 10 μM SR11302. There was significant ($p<0.05$) reduction in COX-2 luciferase activity after FAT1 knockdown as well as FAT1 knockdown with SR11302. (E) q-PCR was done to evaluate the mRNA expression of COX-2, IL6 and IL113 after treatment with 10 μM SR11302. There was >2 fold reduction in the mRNA expression of COX-2, IL6 and IL1β after treatment with SR11302 as compared to DMSO control.

FIGS. 5A to 5F: Simultaneous knockdown of FAT1 and PDCD4 reverses the effects of FAT1 knockdown; (A) FAT1 and PDCD4 mRNA expression was analyzed by q-PCR in U87MG cells treated with siFAT1 and siPDCD4 alone as well as both the siRNAs treated simultaneously. Treatment with siFAT1+siControl was found to upregulate PDCD4 expression while treatment with siFAT1+siPDCD4 down-regulated the PDCD4 expression to the level of siControl alone treated cells. (B,C) Simultaneous knockdown of FAT1 and PDCD4 in U87MG cells restored their migratory and invasive properties comparable to that of siControl treated cells. There was significant increase in cell migration and invasion in U87MG cells treated with siFAT1+siPDCD4 as compared to cells treated with siFAT1+siControl. Cells were counted in five different fields. Each value is mean±standard deviation. Experiment was put up in triplicate and repeated twice. (D) AP-1 luciferase activity significantly increased after PDCD4 knockdown in U87MGsiFAT1 cells. The luciferase activity with siControl is designated as 100%. There was significant increase in AP-1 luciferase activity in U87MG cells treated with siFAT1+siPDCD4 as compared to siFAT1+siControl. And the luciferase activity in cells treated with siFAT1+siPDCD4 is comparable to siControl treated cells. The experiment was repeated thrice following each of three independent transfections and representative data are shown. Results are expressed as mean±standard deviation. (E) The mRNA expression of AP-1 target genes increased in U87MG cells treated with siFAT1+siPDCD4 as compared to siFAT1+siControl. 18s was used as internal control and experiments were done in triplicate. (F) PDCD4 knockdown in U87MGsiFAT1 cells revert back the protein expression of p-c-jun, VEGF-C and COX-2 comparable to siControl alone treated cells. Lysates from indicated cells were probed with respective antibodies. β-actin was used as control antibody.

Figure 6:
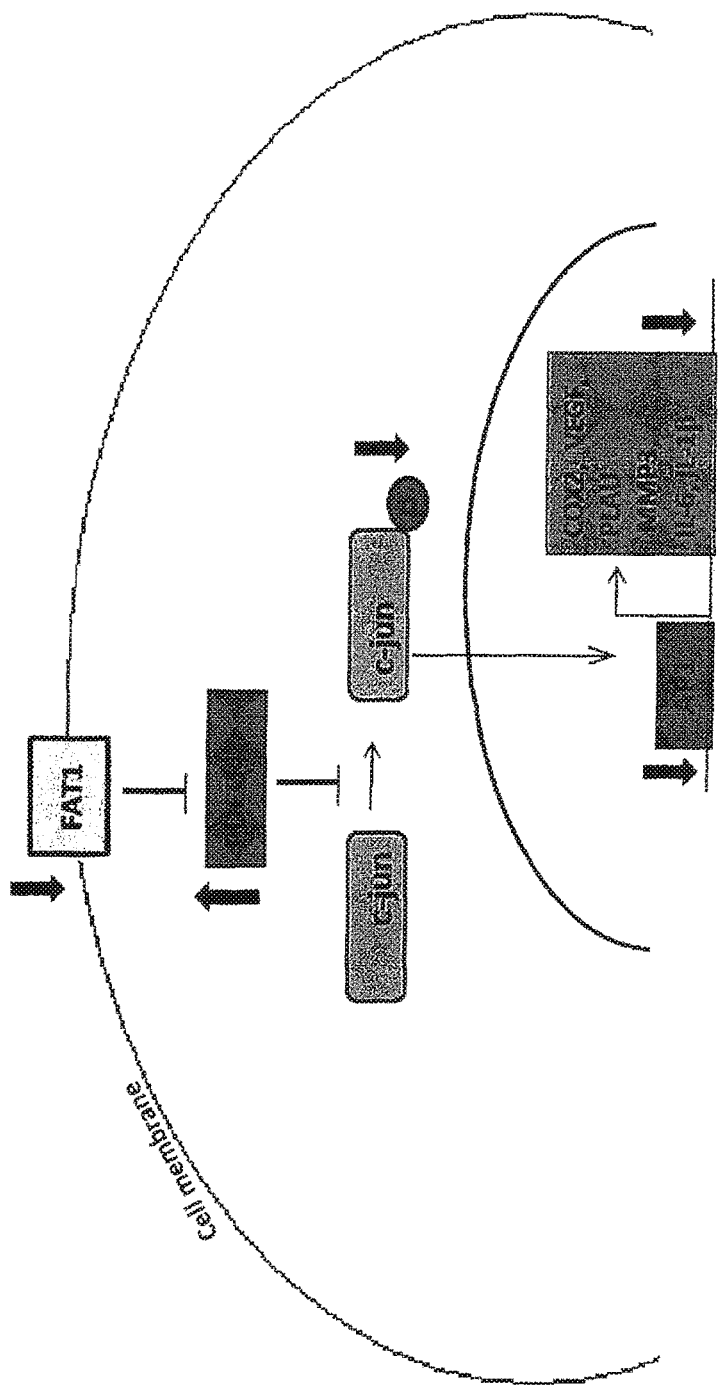

FIG. 6: Signaling pathway downstream of FAT1 regulating AP-1-dependent transcription; Knockdown of FAT1 expression releases its inhibitory effect on PDCD4 and increase the expression of PDCD4. Increased PDCD4 expression in turn inhibits the phosphorylation of c-jun, thus decreasing phospho-c-jun levels. Since phospho-c-jun is required for AP-1 dependent transcription, there was inhibition of AP-1 transcriptional activity and down-regulation of target genes like COX-2, MMP3, VEGF-C, PLAU, IL-6 and IL-1β.

Figure 7:
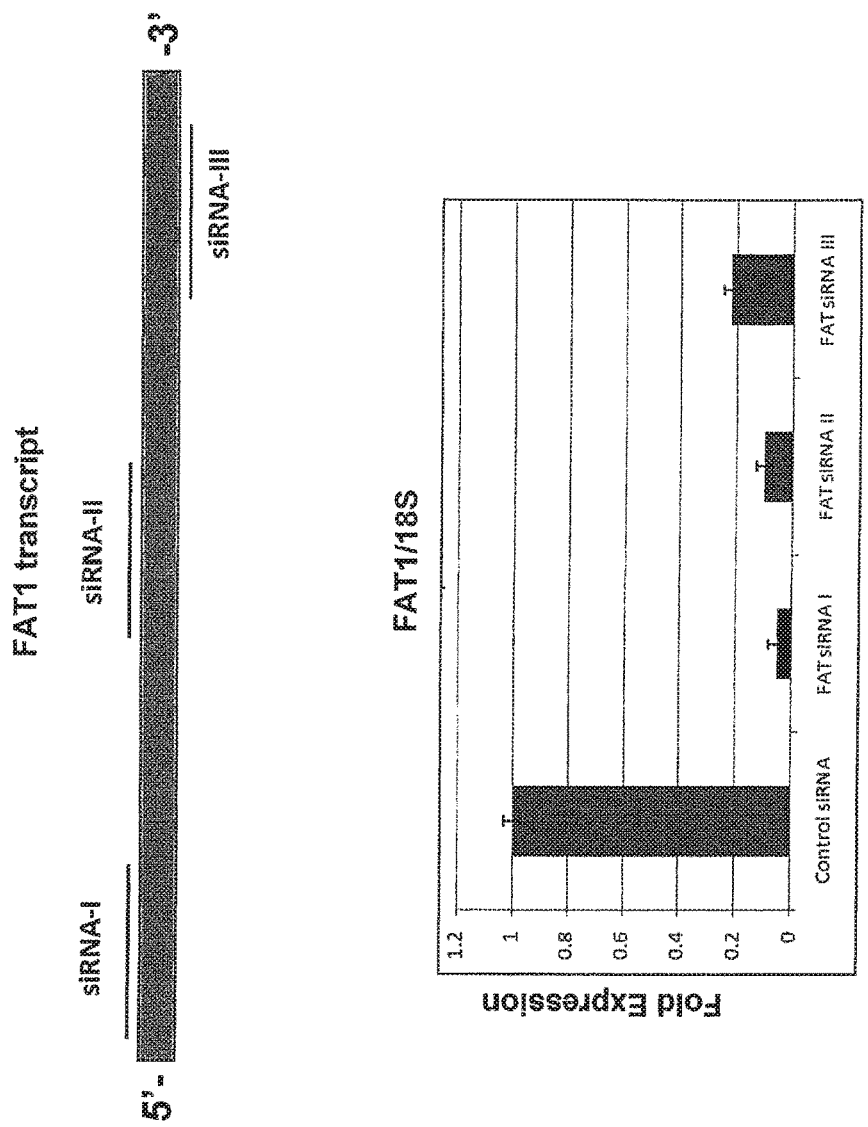
Figure 8:
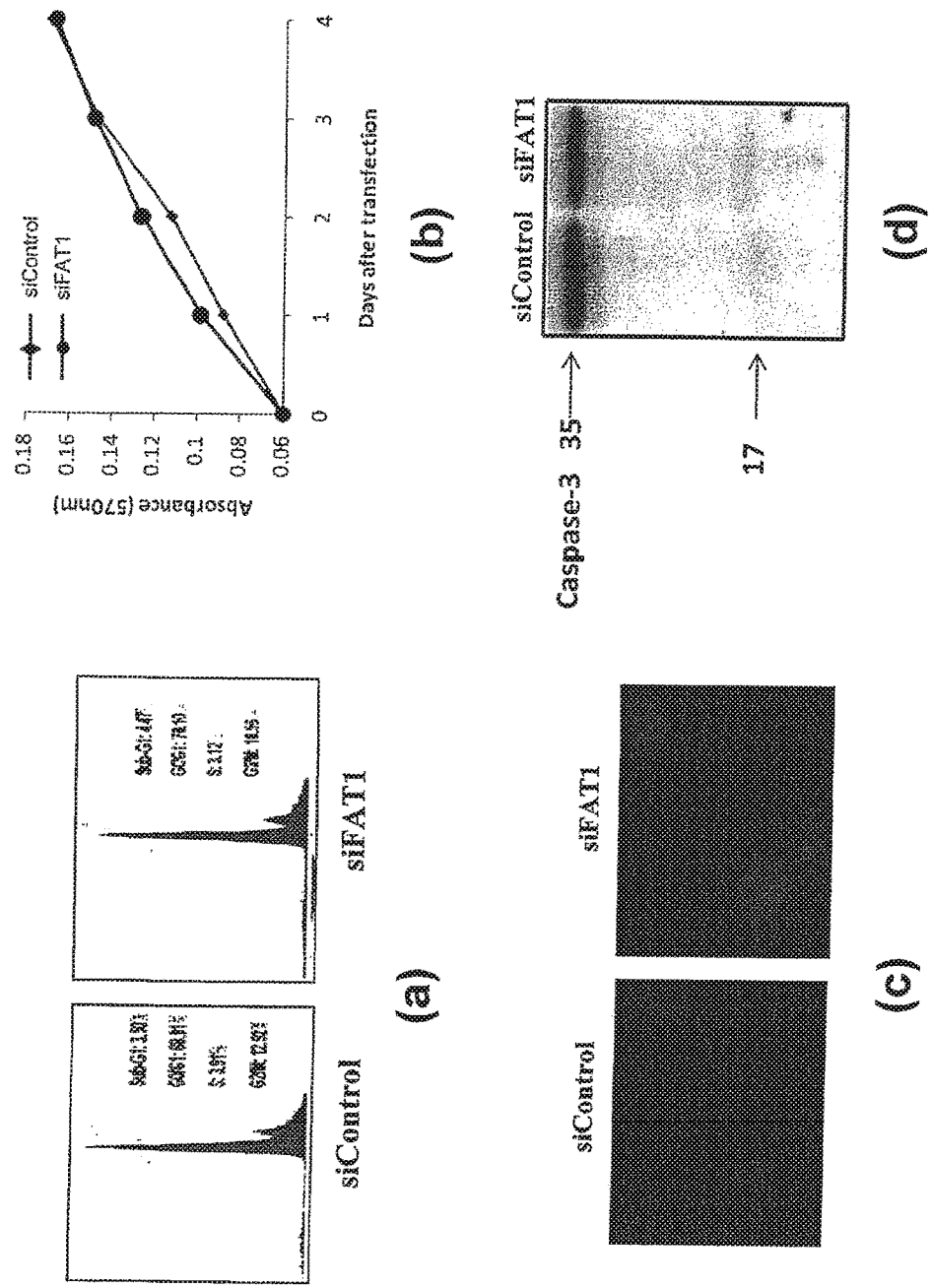

FIG. 7: FAT1 siRNA-I has maximum knockdown efficiency; Three FAT1 siRNA [HSS103567 (FAT1 siRNA-I), HSS103568 (FAT1 siRNA-II) and HSS176716 (FAT1 siRNA-III)] corresponding to different regions of FAT1 transcript were screened for knockdown efficiency. FAT1 siRNA-I was found to have maximum knockdown efficiency as assessed by q-PCR for FAT1 in U87MG cell line. 18S was used as internal control.

FIGS. 8A to 8D: (A) Knockdown of FAT1 leading to high PDCD4 expression does not alter cell cycle progression in U87MG cells; For cell cycle analysis, on day 0, 2×10$^5$ cells were plated in 25 cm$^2$ flask. On day 1, siRNA transfection was carried out. 1 ml of OPTIMEM, 50 picomoles of siRNA (siControl and siFAT1) and 3 μl of LIPOFECTAMINE 2000 was used per well. Cells were then analyzed by flow-cytometery after 72 hrs of transfection to assess the cell cycle distribution of individual cells. Cells were fixed in 70% ethanol overnight at −20'C followed by propidium iodide (PI) staining. Florescence was measured on FACS (florescence activated cell sorter, BD Biosciences, Bedford, Mass.). No difference in the cell population was observed at different cell cycle stages in both siFAT1 and siControl treated cells. (B) FAT1 knockdown does not alter cell proliferation as assessed by MTT assay; On Day 0, four thousand cells were plated per well in 96 well plate in triplicate. On day 1, transfection was carried out. 50 μl of OPTIMEM, 2 picomoles of siRNA (control and FAT1 siRNA) and 0.5 μl of LIPOFECTAMINE 2000 was used per well. After 4 hrs incubation at 37° C., 50 μl 2× media was added per well. After every time point (24, 48, 72 and 96 hrs of transfection), media was removed from wells and 100 μl of MTT (0.2 mg/ml) was added per well and incubated for 2-4 hrs. The formazan crystals formed were dissolved by addition of 100 μl of DMSO and absorbance was measured at 570 nm. No significant difference was observed in U87MGsiFAT1 cells as compared to siControl cells. (C,D) FAT1 knockdown does not result in apoptosis; Apoptosis induction after FAT1 knockdown was assessed by Western blot analysis of caspase3 and by DAPI staining. No differences were observed between U87MGsiFAT1 and siControl cells.

Figure 9:
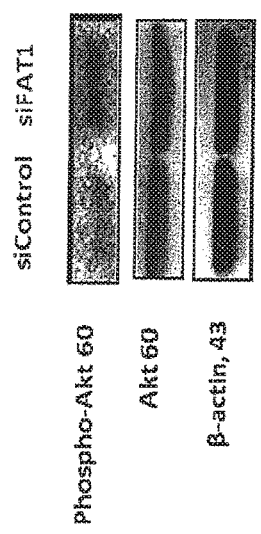

FIG. 9: FAT1 knockdown results in increased p-akt level in U87MG cell line; Akt is known to negatively regulate PDCD4 expression; therefore, the effect of FAT1 knockdown on the phosphorylation status of Akt in U87MG cells was checked by Western blot analysis using β-actin as a loading control. An increase in phospho-Akt level was observed after FAT1 knockdown indicating that the up-regulation of PDCD4 after FAT1 knockdown is likely to be independent of Akt pathway in glioma cells.

Figure 10:
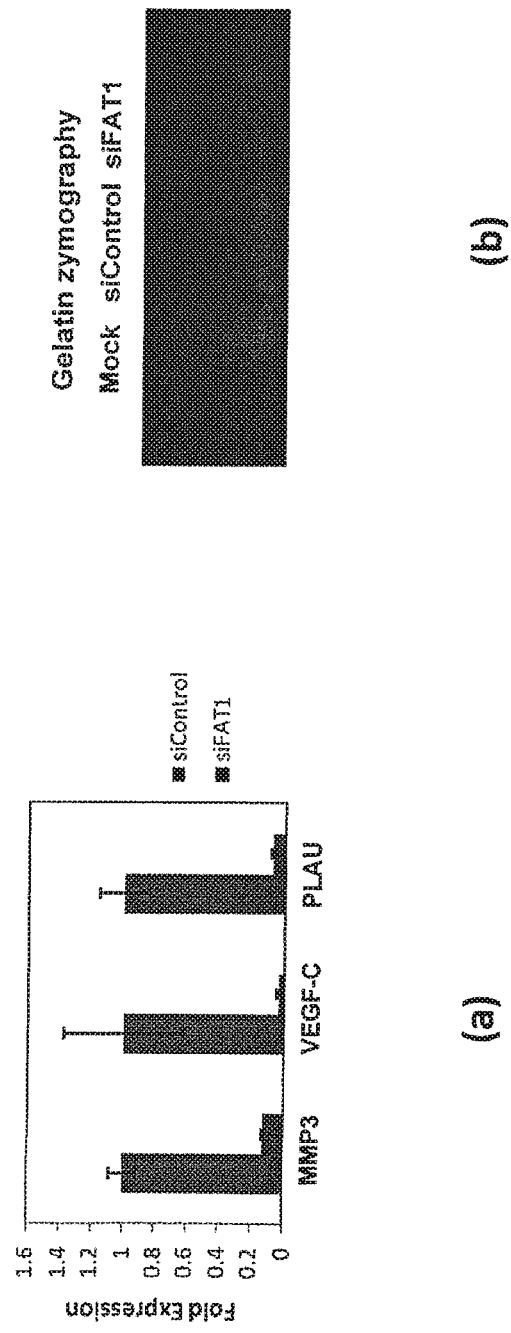

FIGS. 10A and 10B: FAT1 knockdown inhibits ECM protease activity; (A) q-PCR analysis showed that AP-1 regulated ECM remodelling molecules like MMP3, VEGF-C and PLAU were down-regulated more than 10-fold upon FAT1 knockdown in U87MG cells. 18s was used as internal control and each experiment was put up in triplicate and repeated twice. (B) Inhibition of extra cellular protease activity after FAT1 knockdown was determined by gelatin zymography. Conditioned media from indicated cells were separated on a 0.1% gelatin acrylamide gel. The gel was then stained with Coomassie R-250 and photographed. The areas of protease activity appear white on blue background. There was reduced protease activity in siFAT1 treated cells as compared to siControl cells.

Figure 11:
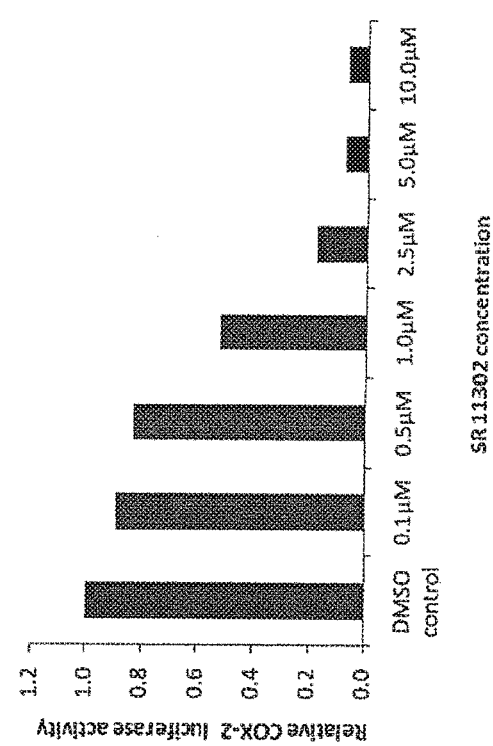

FIG. 11: Dose response curve of SR11302; U87MG cells were treated with increasing concentration of SR11302 from 0.1 μM to 10 μM. Cells were assayed for COX-2 luciferase activity after 48 hrs and 90% decrease was observed in the COX-2 luciferase activity at SR11302 concentrations of 5 and 10 μM. No toxicity to the cells was observed at 10 μM concentration and thus this concentration was used further in other experiments.

Figure 12:
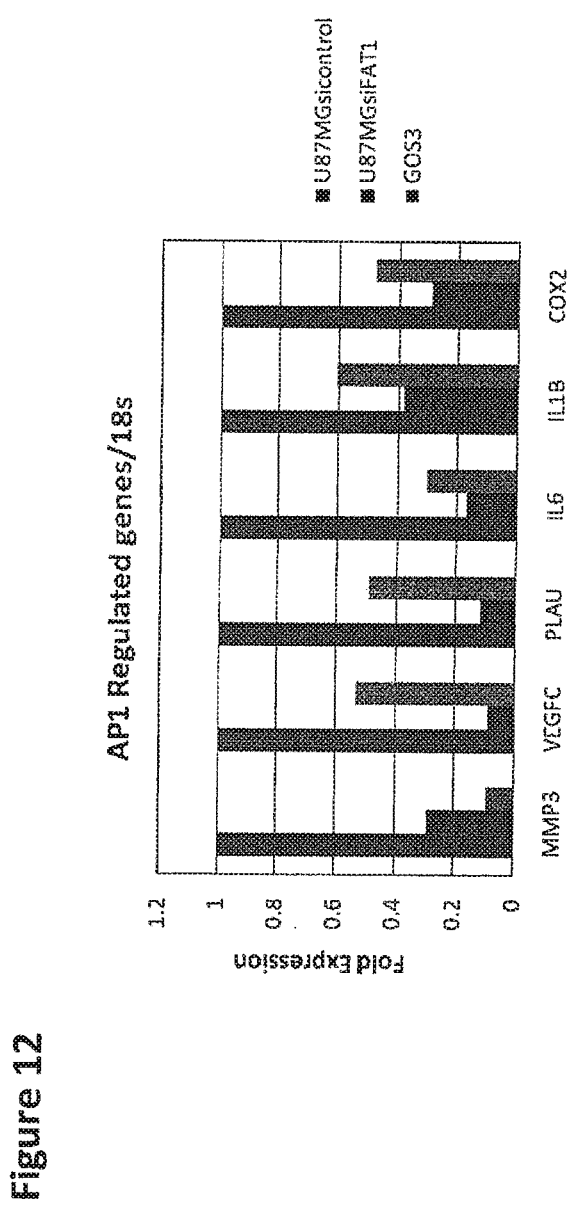

FIG. 12: GOS3 (grade III glioma) cell line with low FAT1 expression had low expression of AP-1 regulated transcripts; GOS3 cell line was found to have low FAT1 and high PDCD4 expression, thus the expression of AP-1 regulated transcripts in GOS3 cell line was checked by q-PCR. Expression of AP-1 regulated transcripts in GOS3 cell line was observed to be low as compared to U87siControl and U87MGsiFAT1 cells. 18S was used as internal control.

Figure 13:
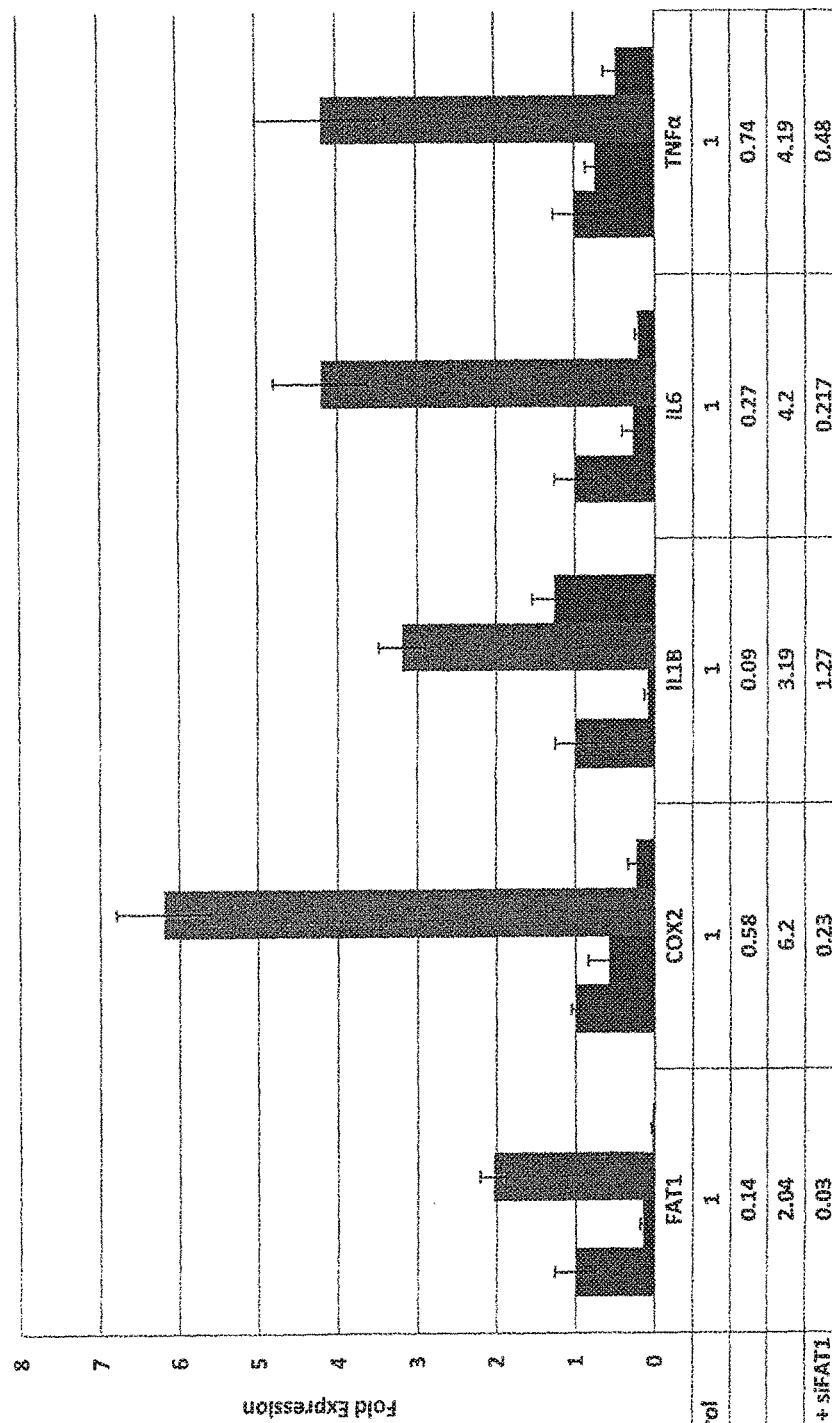
Figure 14:
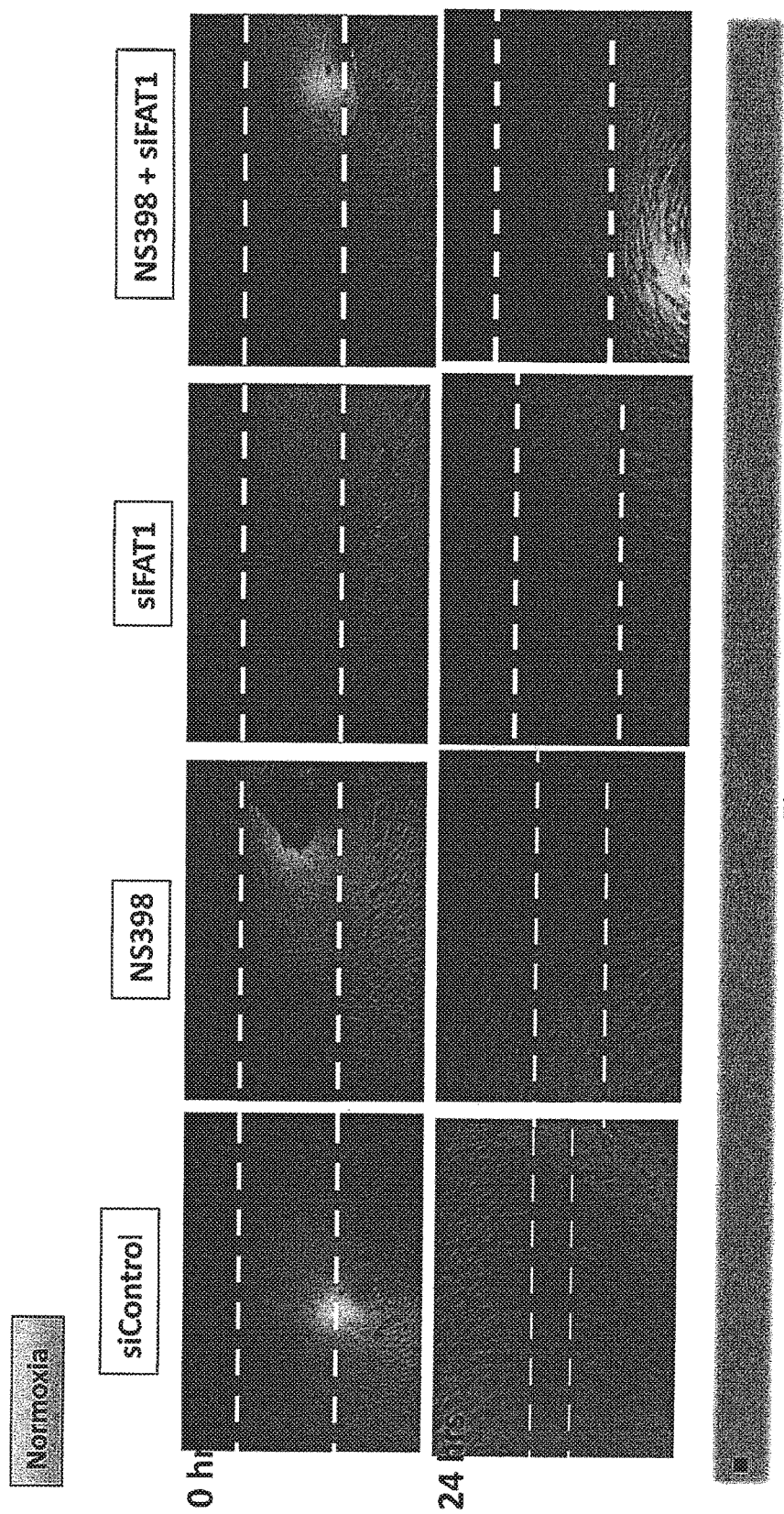
Figure 14:
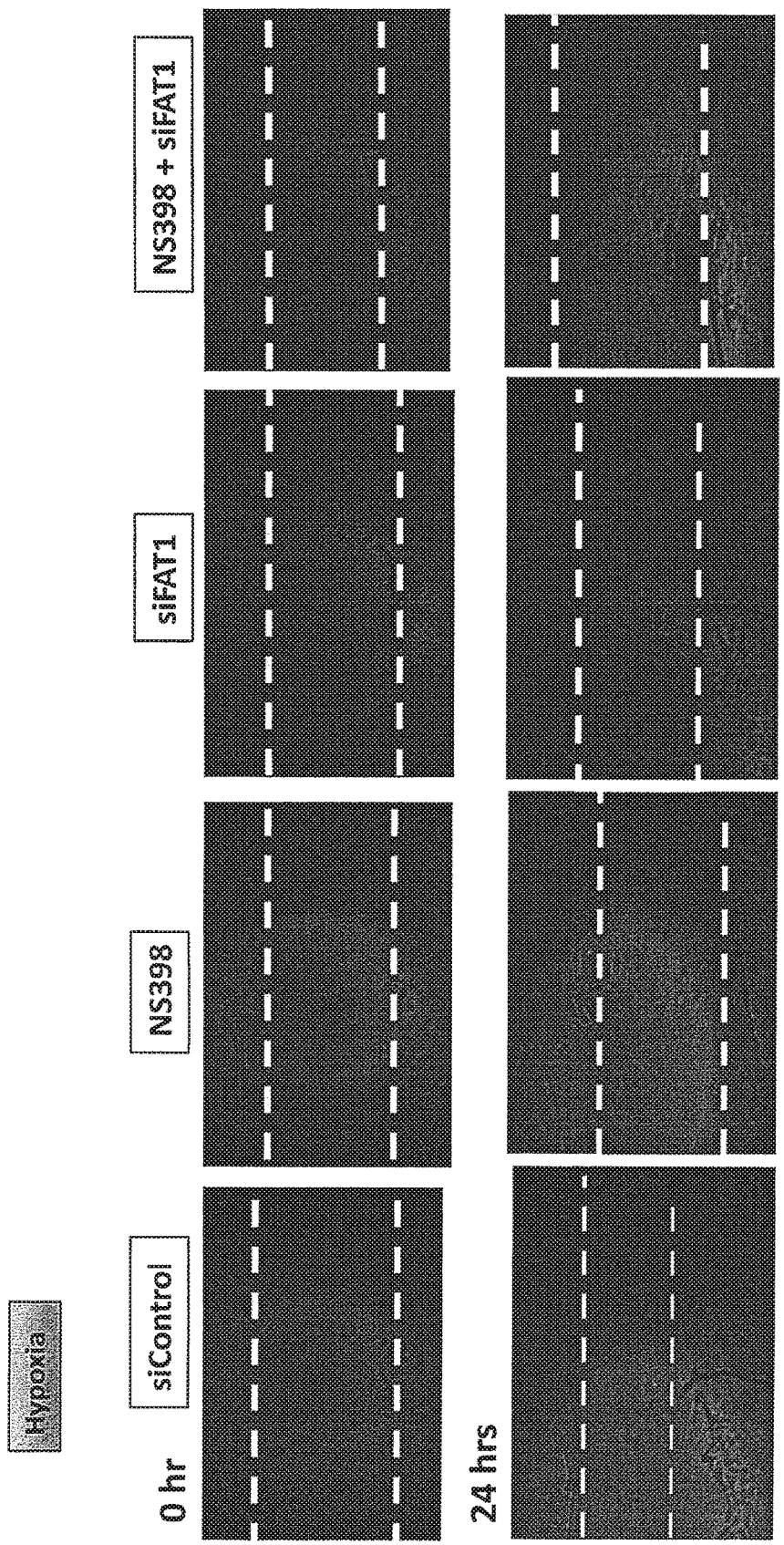
Figure 14:
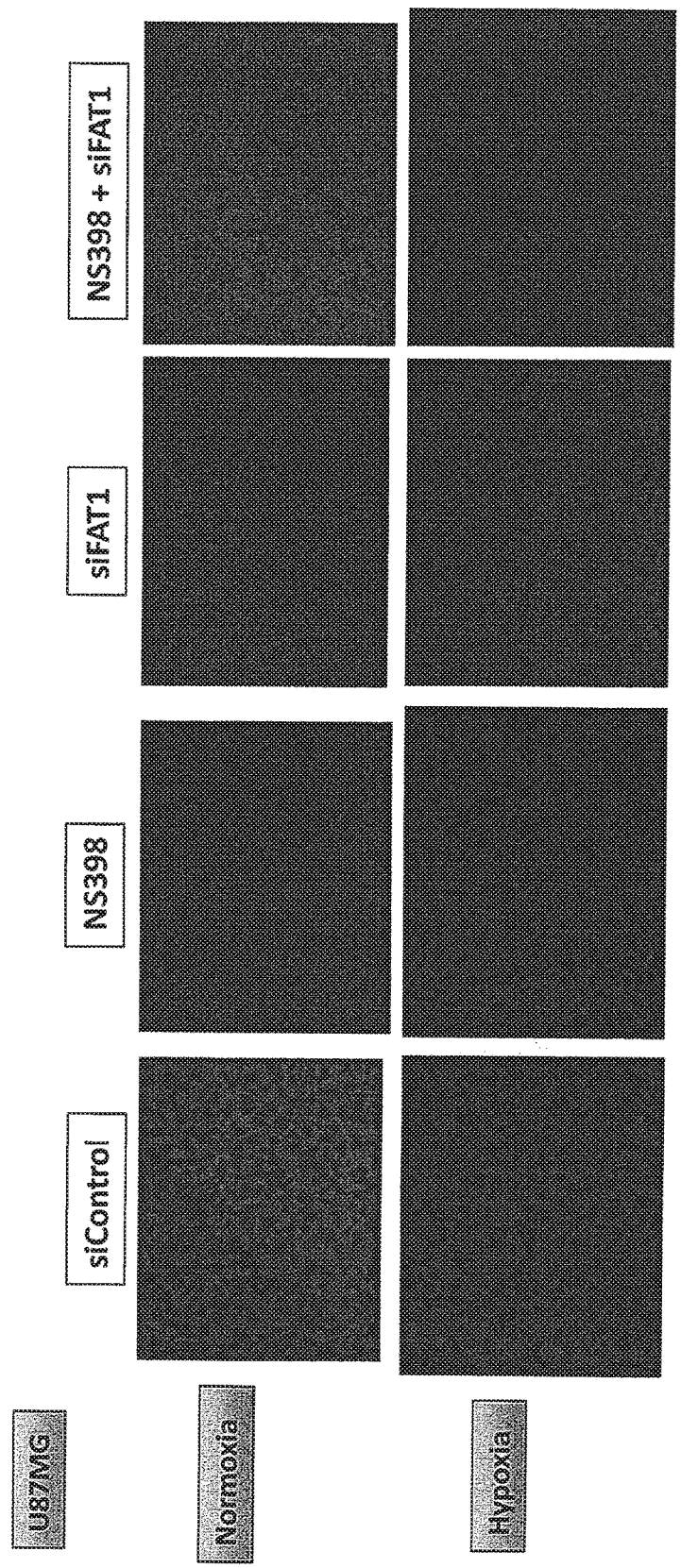

FIG. 13: FAT 1 knockdown prevents the compensatory increase of pro-inflammatory mediators Cox 2, IL1beta, IL6 and TNF alpha.

An experiment was conducted was to demonstrate the combined effect of FAT1 knock down and the prototype Cox 2 inhibitor NS 398. Cells were treated with a) si RNA control b) siRNA to FAT1c) NS398 and d) combined siRNA to FAT1 and NS298. The y axis depicts the increased fold expression with respect to control siRNA under the various conditions. When cells are treated with NS298 alone, there is a compensatory increase in Cox2, IL1beta, IL6 and TNF alpha. This may have a tendency to reduce the effects of Cox2 inhibitor on the proinflammatory environment mediated by the enzyme and other cytokines. However, this effect is abrogated when the cells are simultaneously treated with siRNA to FAT1 and NS398.

FIGS. 14A to 14D: Effect of NS-398 and FAT1 knockdown simultaneously on Cell Migration by In-vitro Scratch Assay. The in vitro Scratch Assay was performed at 72 hours after culturing cells as follows: At Day 0, 5,000 U87MG cells are plated per well of a 96 well plate. At Day 1, the cells are transfected using FAT1 siRNA and then treated with NS398 before culturing them under normoxic (A) or hypoxic (B) conditions. (C) Assay of cell migration by the Modified Boyden Chamber Assay under conditions of normoxia and hypoxia. (D) Quantitation of data from (C). Under either of normoxic or hypoxic conditions, the migration ability of cells was reduced on both FAT1 knockdown and NS398 treatment (more on FAT1 knockdown) and it was further reduced on simultaneous knockdown of FAT1 and NS398 treatment.

DISCLOSURE OF THE INVENTION

The present disclosure demonstrates the role of FAT1, a transmembrane protein, in linking the neoplastic phenotype and inflammatory mediators in cancer cells.

The present disclosure further demonstrates that FAT1 can upregulate some features of tumorigenesis and can function as an oncogene under certain conditions and can also influence the expression of mediators of inflammation.

The present invention demonstrates for the first time that FAT1 plays an important role in modulating PDCD4 expression, which in turn regulates AP1 dependent transcription, controls processes crucial for migration and invasion in cancer cells, controls induction of a pro-inflammatory microenvironment in cancer cells. The invention illustrates a link between inflammation and cancer in cells or in a subject. This work highlights the importance of FAT1 in the induction of the cellular pathways of migration and invasion, proteolysis of the ECM and the expression of pro-inflammatory molecules leading to a favorable microenvironment for tumor and cancer progression.

The present invention also provides the use of FAT1 in regulating neoplastic phenotypes and genotypes including invasiveness and inflammatory microenvironment of the cancer cells by acting as a novel apical regulator of a signaling pathway by affecting the AP1 transcriptional activity, affecting the property of both cell migration and invasion and at the same time affecting the expression of inflammatory modulators.

The present invention by establishing a novel cell signaling pathway that regulate PDCD4 and AP1 mediated transcription—thereby regulating the general inflammatory mediators, IL1β, COX-2, IL6 and prostaglandins—also provides a way of beneficially intervening in pathologies that are intrinsically inflammatory and may not have any link with cancer.

This novel work has not only elucidated the role of FAT1 in regulating some the key invasive properties of a cancer cell and the expression of inflammatory molecules in the cell by being a novel mediator of cell signaling, but this also points to the utilization of the FAT1 modulation as a therapeutic targets in both cancer and inflammatory diseases. In addition, the present elucidation of the link between cancer and inflammation provides insights on how the inflammatory processes are controlled. Hence they provide a basis for the control of intrinsic inflammatory pathology as well.

DETAILED DESCRIPTION OF THE INVENTION

The present invention is described with reference to the tables/figures etc. and specific embodiments; this description is not meant to be construed in a limiting sense. Various alternate embodiments of the invention will become apparent to persons skilled in the art, upon reference to the description of the invention. It is therefore contemplated that such alternative embodiments form part of the present invention.

Unless defined otherwise, technical and scientific terms used herein have the same meaning as commonly understood by one of ordinary skill in the art to which this invention belongs. Some of the terms are defined briefly herebelow; the definitions should not be construed in a limiting sense.

The term "cancer" is defined as a hyperproliferation of cells whose unique trait—loss of normal controls—results in unregulated growth, lack of differentiation, local tissue invasion, and metastasis. Examples include but are not limited to, melanoma, non-small cell lung, small-cell lung, lung, hepatocarcinoma, leukemia, retinoblastoma, astrocytoma, glioblastoma, gum, tongue, neuroblastoma, head, neck, breast, pancreatic, prostate, renal, bone, testicular, ovarian, mesothelioma, cervical, gastrointestinal, lymphoma, brain, colon, sarcoma or bladder.

The terms "cell," "cell line," and "cell culture" may be used interchangeably. All of these terms also include their progeny, which are any and all subsequent generations. It is understood that all progeny may not be identical due to deliberate or inadvertent mutations.

"Glioma" is a type of tumor that starts in the brain or spine. It is called a glioma because it arises from glial cells. The most common site of gliomas is the brain.

"GBM", Glioblastoma Multiforme is the most aggressive and the commonest primary brain tumor with a tendency for local invasiveness.

"Cancer/Tumor microenvironment" denotes the normal cells, molecules, and blood vessels that surround and feed a cancer/tumor cell. The tumor microenvironment plays a crucial role in cancer development and in its progression.

"Cancer/Tumor aggressiveness": Tumor grades are commonly described by four degrees of severity: Grades 1, 2, 3, and 4. The cells of Grade 1 tumors resemble normal cells, and tend to grow and multiply slowly. Grade 1 tumors are generally considered the least aggressive in behavior. Conversely, the cells of Grade 3 or Grade 4 tumors do not look like normal cells of the same type. Grade 3 and 4 tumors are most aggressive, and tend to grow rapidly and spread faster than tumors with a lower grade.

"AP1", the activator protein 1 is a transcription factor which is a heterodimeric protein composed of proteins belonging to the c-Fos, c-Jun, ATF and JDP families. It regulates gene expression in response to a variety of stimuli, including cytokines, growth factors, stress, and bacterial and viral infections. AP-1 in turn controls a number of cellular processes including differentiation, proliferation, and apoptosis.

"FAT1" is a member of cadherin superfamily and was first identified as a tumor-suppressor in *D. melanogaster*, acting via the Salvador-Warts-Hippo (SWH) signaling pathway.

"PDCD4", Programmed Cell Death 4, is a known tumor suppressor gene and it plays an essential role in many biological processes like regulating cap-dependent translation, apoptosis, modulating various signal transduction pathways etc. The expression of PDCD4 is often decreased in human glioma and many other progressive tumors like lung, breast etc., leading to increased invasiveness and metastasis. In addition, PDCD4 is also reported to suppress induction of inflammatory mediators.

PDCD4 is known to inhibit AP-1-mediated transcription which has a central role in multiple processes involved in tumorigenesis including proliferation, migration and invasion. AP-1 inhibition has been shown to have anti-invasive and anti-growth effect.

"Small interfering RNA (siRNA)", sometimes known as short interfering RNA or silencing RNA, is a class of double-stranded RNA molecules, 20-25 base pairs in length. siRNA plays many roles, but its most notable is in the RNA interference (RNAi) pathway, where it interferes with the expression of specific genes with complementary nucleotide sequence. siRNAs are a potent new drug class that can silence a disease-causing gene.

NS398—a selective COX2 inhibitor, binds in the cyclooxygenase channel (the methanesulphonamide moiety of NS398 interacts with the side chain of Arg 120 at the opening of the cyclooxygenase channel). NS-398, an anti-inflammatory agent, selectively inhibits prostaglandin G/H synthase/cyclooxygenase (COX-2) activity in vitro. NS-398 has been reported to mediate growth-inhibitory effects in colon (Tsujii et al Cell 1998), esophageal (Zimmermann et al Cancer Res 1999) and pancreatic carcinoma cell lines (Molina et al Cancer Res 1999). In addition, NS-398 was shown to inhibit proliferation and to induce apoptosis in colorectal and lung carcinoma cell lines (Elder et al Cancer Res 1997, Liu et al Cancer Res 1998).

NS398 has the structure:

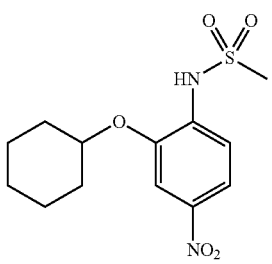 [SMILES: CS(=O)(=O)Nc1ccc([N+](=O)[O-])cc1OC1CCCCC1]

The present disclosure demonstrates that FAT1 can upregulate some features of tumorigenesis and can function as an oncogene under certain conditions and can also influence the expression of mediators of inflammation. The link between FAT1 and PDCD4 is a novel aspect of this invention.

In order to elucidate the functional role of FAT1 in cancer its expression is studied in several cancer cell lines such as glioma cell lines followed by siRNA knockdown of FAT1 in cells in GBM cell lines such as U87MG and A172 with high FAT1 expression. High FAT1 mRNA expression is observed in grade IV glioma cell lines like U87MG, A172, U373MG and T98G and decreased expression in grade III glioma cell lines (GOS3 and SW1088). Knockdown of FAT1 in U87MG and A172 leads to marked reduction in migratory and invasive properties of the cells along with high expression of PDCD4. Increased PDCD4 expression is also observed upon FAT1 knockdown in U373MG and T98 cell lines. PDCD4 inhibits migration and invasion in various cancers like breast, ovarian, colon etc. Loss of PDCD4 expression is linked with cell proliferation and unfavorable prognosis in gliomas. Decreased migration and invasion observed in U87MG and A172 cell lines after FAT1 knockdown in this invention might be attributed to increased PDCD4 expression. High PDCD4 expression after FAT1 knockdown does not induce apoptosis or alter cell cycle distribution in both U87MG and A172 cell lines. It is observed that high PDCD4 levels after FAT1 knockdown mainly regulate migration and invasion in glioma cells. Decreased PDCD4 plays an important role in tumor progression and in remodeling ECM during invasion. To further confirm the link between FAT1 and PDCD4, PDCD4 and FAT1 expression is simultaneously knocked down and reversal of migratory and invasive properties of the cells is found, which further confirms that the observed effects of FAT1 are mainly mediated by PDCD4.

PDCD4 attenuates Activator Protein-1 (AP-1) mediated transcription by inhibiting c-jun phosphorylation. A further research by the present team of inventors to check the effect of FAT1 knockdown on the AP-1 activity by luciferase assay shows diminished AP-1 transcriptional activity and decreased expression of AP-1 regulated transcripts like ECM remodeling molecules MMP3, VEGF-C, PLAU; inflammatory mediator COX-2 and cytokines IL1β and IL6. The reduced AP-1 activity observed in glioma cell lines after FAT1 knockdown is due to inhibition of c-jun transcription and c-jun phosphorylation by increased PDCD4 expression. These effects are further confirmed by dual knockdown of FAT1 and PDCD4 in both U87MG and A172 cell lines. Also, the increased PDCD4 expression after FAT1 knockdown in glioma cells is found to be independent of Akt pathway. The observation of FAT1 in regulating PDCD4 expression and its downstream effect on tumor migration and invasion is a novel finding with implications for cancer and tumor cell biology such as glioma biology.

AP-1 binding to a c-AMP response element in the COX-2 promoter regulates COX-2 expression. The present disclosure shows that inhibition of AP-1 by SR 11302 (a known inhibitor of AP1 activity) leads to significant reduction in COX-2 promoter-driven luciferase activity as well as mRNA expression of COX-2. This indicates that down regulation of FAT1 has the same effect on the COX-2 promoter as the small molecule inhibitor of AP1 activity (SR 11302), thus further illustrating the mode of action of FAT1. The down-regulation of COX-2 expression and pro-inflammatory cytokines via PDCD4 up-regulation after FAT1 knockdown has considerable significance in the regulation of inflammatory responses in cancer and tumor cells. Decreased COX-2 expression after FAT1 knockdown leads to reduced PGE2 production and decreased mRNA expression of IL6 and IL1β, thus providing a crucial link between tumor progression and inflammation. PDCD4 has a role in down-regulating COX-2 and suppression of PDCD4 increases invasive activity of COX-2 in breast cancer cells. COX-2 over-expression is also reported in high grade gliomas and many other tumors with potential for targeting it as anti-cancer modality. The present disclosure of reduced COX-2 expression and decreased synthesis of prostanoids (PGE2) and cytokines, IL1β and IL6, after FAT1 knockdown indicates the role of FAT1 in regulating oncogenic and inflammatory properties in cancer and tumor such as gliomas. COX2 is a molecule known to be involved in tumor and inflammation.

Regulation of COX2 expression by FAT1 is a novel finding linking inflammation and tumorigenesis in cancer cells. The novel pathways indicate a mechanism of regulating inflammatory pathology as such, even without any link to cancer. Thus, targeting FAT1 provides strong advantages for managing both tumorigenicity as well as the inflammatory microenvironment of cancer cells.

To further validate the in-vitro findings about the relationship between FAT1 and PDCD4, the expression of FAT1 and PDCD4 in 35 primary GBM samples is studied by q-PCR and a statistically significant inverse correlation between the two is observed. Further, a positive correlation between FAT1 and COX-2 expression and a similar trend for IL6 expression in GBM samples studied is also observed. These findings further support the in-vitro results about the inverse relationship between FAT1 and PDCD4 and their influence on the expression of AP-1 mediated transcripts like COX-2, IL6 etc.

The present disclosure demonstrates for the first time that FAT1 plays an important role in modulating PDCD4 expression, which in turn regulates AP-1 dependent transcription, controls processes crucial for migration and invasion in cancer cells, controls induction of a pro-inflammatory microenvironment in cancer cells. The study illustrates a link between inflammation and cancer in cells or in a subject. This work highlights the importance of FAT1 in the induction of the cellular pathways of migration and invasion, proteolysis of the ECM and the expression of pro-inflammatory molecules leading to a favorable microenvironment for tumor and cancer progression.

The present invention shows that FAT1 affects some of the key modulators of cancer phenotype (including invasion and metastasis) like the up-regulation of targets of the transcription factor, AP1, down-regulation of the tumour suppressor gene PDCD4, and angiogenesis (VEGF). It also affects some of the key inflammatory molecules like IL1 β, IL6 and COX2. One of the ways in which FAT1 acts is through the key transcription factor AP1.

The finding of reduced COX-2 expression and decreased synthesis of prostanoids (PGE2) and cytokines, IL1β and IL6, after FAT1 knockdown points toward the role of FAT1 in regulating oncogenic and inflammatory properties in cancer cells. Thus, targeting FAT1 has strong advantages for managing both tumorigenicity as well as the inflammatory microenvironment of gliomas.

This novel work has not only elucidated the role of FAT1 in regulating some the key invasive properties of a cancer cell and the expression of inflammatory molecules in the cell by being a novel mediator of cell signaling, but this also points to the utilization of the FAT1 modulation as a therapeutic target in both cancer and inflammatory diseases.

The present disclosure demonstrates the role of FAT1, a transmembrane protein, in linking the neoplastic phenotype and inflammatory mediators, and especially in glial cells.

Down-regulation of FAT1 and its action is a key point of therapeutic intervention. It is also used as a target, at the level of gene, RNA and proteins and derivatives thereof, for either cancer or inflammation or both. Naturally occurring as well as synthetic molecules that modulate FAT1 expression and activity also may have a role in the amelioration of either or both the processes. FAT1 (gene, RNA or protein or its derivatives) also serves as a biomarker for the two processes i.e. cancer and inflammation.

This is the first report showing a novel role of FAT1 in regulating both aggressiveness and inflammatory microenvironment of the cancer cells via a signaling pathway where FAT1 is acting as an apical regulator.

Thus, the present disclosure provides down regulation of AP1 by FAT1, in conditions where overexpression of AP1 is causing adverse effect, such as cancer and inflammation.

Further, the present disclosure provides modulation of FAT1 mRNA/protein as a method of abrogating cancer and/or inflammation, The present disclosure further provides FAT1 as a link between cancer and inflammation and also as a biomarker for the same.

The present disclosure further provides FAT1 as a biomarker for cancer and inflammation.

An embodiment of the invention provides a method for abrogating cancer and/or inflammation in a cell or cell line or tissue, said method comprising down-regulating FAT1 gene expression, wherein the cell or cell line or tissue is adversely affected by over expression of FAT1.

In another embodiment, the down-regulation of FAT1 gene results in:
 a. upregulation of PDCD4;
 b. inhibition of AP-1 transcriptional activity;
 c. decrease in expression of AP-1 target genes;
 d. decrease in expression of inflammatory modulators and cytokines; and
 e. decrease in cell migration and invasion.

In yet another embodiment, the AP-1 target genes are selected from the group comprising MMP3, VEGF-C, PLAU and COX-2.

In yet another embodiment, the inflammatory modulator is COX-2 and inflammatory cytokines are such as IL6 and IL1β.

A further embodiment of the invention is a method of regulating aggressiveness and inflammatory microenvironment of a cell or cell line or tissue, wherein the method comprises regulating the expression of FAT1 gene.

In a specific embodiment, the regulation of expression of FAT1 gene comprises down-regulation of the FAT1 gene.

In yet another embodiment, the regulation of expression of FAT1 gene affects a signaling pathway primarily involving PDCD4 and AP1.

One more embodiment of the invention is a method of regulating neoplastic phenotypes in a cell or cell line or tissue, said method comprising down-regulating expression of the FAT1 gene. In another embodiment, said down-regulation of FAT1 gene results in:
 a. upregulation of PDCD4;
 b. inhibition of AP-1 transcriptional activity;
 c. decrease in expression of AP-1 target genes;
 d. decrease in expression of inflammatory modulators and cytokines; and
 e. decrease in cell migration and invasion.

In yet another embodiment the cell or cell line or tissue is selected from glioma cell line, cells showing inflammation, cells showing higher levels of expression of AP1. Specifically, the glioma is glioblastoma multiforme. More specifically, the cell line is selected from group comprising U87MG, A172, U373MG and T98G.

The method as discussed above is preferably performed in a cell or a cell line or tissue in laboratory under controlled conditions and is performed in vitro.

The method as discussed above can be easily performed under in vivo conditions also.

Another aspect of the invention is to provide novel use of FAT1 gene.

In an embodiment, the invention provides use of FAT1 gene and its products for targeting inflammation and/or cancer and the associated phenotypes and genotypes.

In a further embodiment, the invention provides use of FAT1 gene and its products as a biomarker for detecting inflammation and/or cancer.

In yet another embodiment, the invention provides use of FAT1 gene and its products as a target for treatment of inflammation and/or cancer. The products of FAT1 comprise FAT1 RNA, protein and its derivatives. Said use comprises regulating FAT1 gene expression. More specifically, regulating of FAT1 gene expression comprises down-regulation of FAT1 gene. The down-regulation of FAT1 gene results in:
  a. upregulation of PDCD4;
  b. inhibition of AP-1 transcriptional activity;
  c. decrease in expression of AP-1 target genes;
  d. decrease in expression of inflammatory modulators and cytokines; and
  e. decrease in cell migration and invasion.

In another aspect, the invention provides a method of detecting or diagnosing cancer and/or inflammation in a subject or in a cell or cell line or tissue by studying expression of FAT1 gene expression. Over expression of FAT1 gene in a cell or cell line or tissue or a subject indicates presence of cancer and/or inflammation.

In another aspect, the invention provides a method for abrogating cancer and/or inflammation in a subject or in a cell or cell line or tissue, wherein the method comprises down-regulating FAT1 gene expression.

In a further aspect, the invention provides a method of regulating aggressiveness and inflammatory microenvironment of adversely affected cells in a subject or in a cell or cell line or tissue, wherein the method comprises regulating the expression of FAT1 gene in the subject.

In yet another aspect, the invention provides a method of regulating neoplastic phenotypes and genotypes in a subject or in a cell or cell line or tissue, wherein the method comprises down-regulating expression of the FAT1 gene in the subject.

In one more aspect, the invention provides a method of controlling AP1 transcriptional activity in a subject or in a cell or cell line or tissue, said method comprising down-regulating expression of FAT1 gene.

Another aspect of the invention provides FAT1 gene for use in a method of detecting or diagnosing cancer and/or inflammation in a subject or in a cell or cell line or tissue by studying expression of FAT1 gene expression.

Yet another aspect of the invention provides FAT1 gene for use in a method for abrogating cancer and/or inflammation in a subject or in a cell or cell line or tissue, wherein the method comprises down-regulating FAT1 gene expression.

One more aspect of the invention provides FAT1 gene for use in a method of regulating aggressiveness and inflammatory microenvironment of adversely affected cells in a subject or in a cell or cell line or tissue, wherein the method comprises regulating the expression of FAT1 gene in the subject.

A further aspect of the invention provides FAT1 gene for use in a method of controlling AP1 transcriptional activity in a cell or cell line or tissue or a subject, said method comprising down-regulating expression of FAT1 gene.

Yet another aspect of the invention provides a method for selecting a drug/active molecule for the treatment of a cancer and/or inflammation, the method comprising:
  a. obtaining a cell or cell line or tissue adversely affected by over-expression of FAT1
  b. contacting said cell or cell line or tissue with drug/active molecule;
  c. determining the expression level of FAT1 in the cells or cell line or tissue; and
  d. selecting a suitable anticancer/anti-inflammatory drug based upon the expression level of FAT1 determined in step (c)
wherein down-regulation of FAT1 is indicative of a useful drug/active molecule.

In another aspect, the invention relates to a method of reducing the invasiveness into extracellular matrix of a cell or migration of a cell, said cell being a cell of a tumor cell line or of a tumor tissue of a subject, and/or reducing secretion of inflammatory cytokines from a cell of a subject, comprising:
  i) assaying the activity of FAT1 and AP1 in said cell or tissue;
  ii) comparing the activity of FAT1 and AP1 in said cell or tissue with the activities of FAT1 and AP1 in non-tumor cells or cells of non-inflamed tissues, and identifying as invasive or inflammatory cells those cells having activity of FAT1 and of AP1 higher than the activity of FAT1 and AP1 in non-tumor cells or in non-inflamed tissues; and
  iii) contacting said cells identified as invasive or inflammatory with a compound that reduces the expression of FAT1 in said invasive or inflammatory cells.

The present invention also provides a method of treating cancer or inflammation in a subject, comprising administering to said subject presenting with either or both of cancer and inflammation a pharmaceutical composition comprising an inhibitor of FAT1 expression or FAT1 activity and a pharmaceutical composition comprising an inhibitor of COX2 activity. This aspect of the invention might also include further steps of:
  i) assaying the activity of FAT1 and AP1 in said subject;
  ii) comparing the activity of FAT1 and AP1 in said subject with the activities of FAT1 and AP1 in normal subjects, and identifying as a subject one that would benefit from treatment a subject having activity of FAT1 and of AP1 higher than the activity of FAT1 and AP1 in normal subjects; and
  iii) administering to said subject that would benefit from treatment a pharmaceutical composition comprising an inhibitor of FAT1 expression or FAT1 activity and a pharmaceutical composition comprising an inhibitor of COX2 activity.

In some embodiments of any aspect of the invention, the compound that reduces expression of FAT1 in said invasive or inflammatory cells is a siRNA. In some embodiments, the siRNA that reduces the expression of FAT1 in said invasive or inflammatory cells is a double-stranded RNA having a nucleotide sequence that is a portion of SEQ ID NO: 1. The siRNA is typically a 25-mer. A preferred siRNA comprises or consists of the nucleotide sequences of SEQ ID NO: 2 and SEQ ID NO: 3.

Down regulation of gene expression for the purpose of the invention can be performed by any method conventionally known in the art or known to a person skilled in the art, including but not limited to gene deletion; mutagenesis including insertional mutagenesis, induction of heterochromatization in a targeted manner, dominant negative mutants, silencing using siRNA, shRNA, ribozyme, antisense RNA, antibodies, small molecules that interfere with protein function, peptides, protein fragments that inhibit the function of the native protein, interference with post translational modifications. Preferably, down-regulation comprises silencing using siRNA.

Pharmaceutical compositions of a number of selective COX2 inhibitors are well-known in the art, and several are approved for marketing by the U.S. Food and Drug Administration, e.g. celecoxib. Formulation of pharmaceutical compositions of siRNAs and other oligonucleotide nucleic acids and their administration to a subject are also well-known in the art. See, e.g. U.S. Pat. Nos. 8,541,568, 8,389,708, 8,313,772, and 8,742,091, all of which are hereby incorporated by reference in their entirety and for all purposes. Any of such formulations and methods of administration may be used in the present invention.

The present disclosure with reference to the accompanying examples describes the present invention. However, those of skill in the art should, in light of the present disclosure, appreciate that many changes can be made in the specific embodiments which are disclosed and still obtain a like or similar result without departing from the spirit and scope of the invention. It is understood that the examples are provided for the purpose of illustrating the invention only, and are not intended to limit the scope of the invention in any way.

EXAMPLES

Example 1

Materials and Methods

Reagents and Antibodies: Set of three siRNAs for FAT1 knockdowns, FAT Stealth RNAi siRNA-I (HSS103567) FAT Stealth RNAi siRNA-II (HSS103568) and FAT Stealth RNAi siRNA-III (HSS176716)) and universal medium GC control siRNA (cat. No 12935-112) were purchased from Invitrogen Life technologies, USA (Grand Island, N.Y.). For simultaneous knockdowns, on-target plus siRNA against FAT1 (J-010513-07-0020) and PDCD4 (J-004438-08-0020) and on-target plus non-targeting pool (D-001810-10-20) as control siRNA from Dharmacon (Chicago, Ill., USA). AP-1 luciferase reporter plasmid (AP-1 7×) was purchased from Stratagene, COX-2 promoter luciferase construct (a kind gift from Dr. Miguel A. Iniguez, Centro de Biología Molecular Universidad Autónoma de Madrid, Spain). AP-1 inhibitor SR 11302 was purchased from Tocris Biosciences (Bristol, UK); Normal brain RNA from Ambion, Life Technologies and Clontech (Mountain view, Calif., USA). Antibodies used for western blots, like PDCD4, COX2, p-c-jun, c-jun, and β-actin were from Cell signaling technology (Beverly, Mass., USA), VEGF and Caspase-3 were from Abcam (Cambridge, UK). Primers were designed using Primer3 software and ordered from MWG Biotech (Germany).

Cell Culture and siRNA Transfection: The human glioma cell lines U87MG, U373, A172, T98G, GOS3 and SW1088 were obtained from ATCC; Rockville, Md., cultured in DMEM (Sigma-Aldrich, Switzerland) supplemented with 10% (v/v) FCS (Sigma-Aldrich), 3.7 g/l sodium bicarbonate (Sigma-Aldrich), Ciprofloxacin 10 µg/ml and 5% $CO_2$ at 37° C. For transfection, $2\times10^5$ cells were seeded per 25 $cm^2$ flask. After 24 hrs, cells were transfected with FAT1 siRNA and universal medium GC control siRNA (Invitrogen) according to the manufacturer's protocol with a final concentration of 20 nM of siRNA using LIPOFECTAMINE 2000 (Invitrogen) and Opti-Mem media (Invitrogen). After 4 hrs of siRNA transfection, the media was supplemented with DMEM containing 2×FCS. The ability of each siRNA to mediate knockdown of FAT1 mRNA was confirmed using qRT-PCR. Photomicrographs of the cells were taken using an inverted phase contrast microscope (Nikon TMS, Phase contrast microscope, Japan). For simultaneous knockdown of FAT1 and PDCD4, siRNA from Dharmacon were used. Transfection was performed as earlier with 50 nM of FAT1 siRNA along with 50 nM of PDCD4 siRNA or 50 nM of control siRNA.

TABLE 1

Sequences of the primers and the annealing temperature used for real-time PCR

| Target genes | Primer sequences | Annealing temperature (° C.) |
|---|---|---|
| 18s | Forward<br>5'-GTAACCCGTTGAACCCCATT-3'<br>Reverse<br>5'-CCATCCAATCGGTAGTAGCG-3' | 55-60 |
| FAT1 | Forward<br>5'-TTCAAAATAGGTGAAGAGACAGGTG-3'<br>Reverse<br>5'-TTGTGATGAGACCTGTTTTAGGATG-3 | 59 |
| PDCD4 | Forward<br>5'-CCTGCAGGGTATTTTCCCTAA-3'<br>Reverse<br>5'-TGGTTGGCACAGTTAATCCA-3' | 58 |
| COX-2 | Forward<br>5'-CTGCTCAACACCGGAATTTT 3'<br>Reverse<br>5'-TTGAATCAGGAAGCTGCTTTT-3' | 59 |
| c-JUN | Forward<br>5'-GTGTCCCCCGCTTGCCACAG-3'<br>Reverse<br>5'-TCGGCGTGGTGGTGATGTGC-3' | 61 |
| MMP3 | Forward<br>5'-CAGGGATTAATGGAGATGCC-3'<br>Reverse<br>5'-AGTCAGGGGGAGGTCCATAG-3' | 57 |
| VEGF-C | Forward<br>5'-TGAACACCAGCACGAGCTAC-3'<br>Reverse<br>5'-GTTGAGTCATCTCCAGCATCC-3' | 57 |
| IL1β | Forward<br>5'-GAGCACCTTCTTTCCCTTCA-3'<br>Reverse<br>5'-TCATCTTTCAACACGCAGGA-3' | 57 |
| IL6 | Forward<br>5'-ATGAGGAGACTTGCCTGGTG-3'<br>Reverse<br>5'-GCATTTGTGGTTGGGTCAG-3' | 57 |
| PLAU | Forward<br>5'-AGCGACTCCAAAGGCAGCAATGA-3'<br>Reverse<br>5'-CAGGGTCGCCTCCGGTTGTC-3' | 58 | cDNA Synthesis and Quantitative PCR: Total RNA was isolated from cells at appropriate time point (vide supra) using TRIzol reagent (Invitrogen), quantified using a Nanodrop ND-1000 spectrophotometer. DNase (Ambion) treatment was given and 1 µg of total RNA was used for cDNA synthesis, done by Fermentas RevertAid™ First Strand cDNA Synthesis Kit using random decamers. PCR reactions were carried in 10 µL reaction volumes (2.5 µL of 1:5 diluted cDNA, 0.5mL of primer mix (0.5 pmol/µL as final concentration of each primer), 1 µL, of 10× Taq Buffer A, 0.5 U Taq polymerase (Bangalore Genei, Bangalore, India), 1 μL Syto9 (Invitrogen), 0.25 μL of 10 mM dNTPs (MBI Fermentas, Thermo Fisher Scientific, Rockford, Ill. USA), and 4.6 μL of nuclease-free water (Ambion) on a RotorGene6000 Real Time PCR in triplicates. The detail of the primers used is given in Table 1. ΔCt values were defined as target gene Ct minus 18s RNA Ct and averaged for each triplicate sample. Statistical significance was determined by Student's t-test analysis (P<0.05).

Western Blotting Analyses: Cells were lysed in triple detergent buffer containing protease and phosphatase inhibitors (Sigma Aldrich), lysates were quantified by BCA kit (Pierce, Thermo Fisher Scientific, Rockford, Ill. USA) and electrophoresed in 10% SDS-PAGE and electroblotted on nitrocellulose membrane (Millipore, Billerica, Mass., USA). Membrane was blocked with 5% bovine serum albumin (BSA) in 1×TBS at 4° C. for overnight. Primary and secondary antibody was diluted in 5% BSA and 0.1% tween-20 in 1×TBS. Blot was incubated in primary antibody overnight at 4° C. followed by secondary antibody incubation for 2 hrs at room temperature. Blot was developed by BCIP-NBT (Promega, Madison, Wis., USA) and captured using Alpha Imager EP software.

Migration and Invasion Assays: The modified Boyden chamber/matrigel assay was performed according to the manufacturer's directions (BD Biosciences, Bedford, Mass.). For in vitro migration assays, chambers with control inserts that lacked the matrigel coating were used. Transfections were carried out in U87MG and A172 cells and 48 hrs later $3 \times 10^4$ U87MG cells/well and $7 \times 10^4$ A172 cells/well were resuspended in serum-free DMEM and seeded in triplicate in matrigel-coated (1 mg/ml; BD Biosciences) and uncoated control inserts (8-μm pore-size, BD Bioscience, Bedford, Mass.). The remaining protocol was done as previously described.

The Scratch Assay is performed at 72 hours after treatment. A scratch is made on the culture surface using a sterile 10 μl tip and cells were allowed to grow. Images were captured after every 3 hrs to monitor the closure of the wound in the culture surface for next 24 hrs.

AP-1 and COX-2 Promoter Luciferase Assay: U87MG cells (40000 cells/well) were plated in 6-well plates in triplicate on day zero. On day 1, cells were transfected with siFAT1 and siControl. On day 2 cells were transiently transfected with 4×AP-1-luciferase reporter plasmids as described previously. Cells were transfected with 1 μg of AP-17× luciferase reporter plasmid, along with 50 ng of pRL-TK (Renilla luciferase) control plasmid using LIPOFECTAMINE2000 as the transfection reagent. After 48 hrs, the cells were lysed by 1× passive-lysis-buffer (Promega, Madison, Wis., USA) and assayed for luciferase activity as previously described. For COX-2 luciferase assay U87MG cells were transfected with siFAT1 and siControl on day 1 and after 4 hrs incubation were treated with 10 μM SR11302. On day2 cells were transiently transfected with COX-2 reporter plasmid and again treated with 10 μM SR11302. After 48 hrs, the cells were assayed for luciferase activity.

Gelatin Zymography: U87MG cells ($2.5 \times 10^5$ cells/flask) were plated into 25 cm² flask. Transfection was performed on day 1 and after 72 hrs, the conditioned medium was collected, clarified by centrifugation, concentrated by Centricon YM-30 (10:1 concentration; Millipore, Billerica, Mass., USA), and separated in non-reducing polyacrylamide gels containing 0.1% (wt/vol) gelatin. The gel was incubated with 1× Zymogram renaturing buffer for 30 min at room temperature, 1× Zymogram developing buffer for 30 min at room temperature, and 1× Zymogram developing buffer at 37° C. for overnight. The gel was then stained for protein with 0.25% (w/v) Coomassie Blue R-250 and then destained with Coomassie R-250 destaining solution (Methanol:Acetic acid:Water (50:10:40). Proteolysis was detected as a white zone in a dark field.

PGE2 ELISA: U87MG cells ($2.5 \times 10^5$ cells/flask) were plated into 25 cm² flask. Transfection was performed on day 1 and 72 hrs later, the conditioned medium was collected and concentrated using Centricon YM-30. The concentration of PGE2 secreted into the medium was measured with an EIA kit for human PGE2 (Cayman Chemical, Michigan, USA).

Human GBM Samples: Tumor tissues were obtained at the time of surgery from 35 GBM patients from Neurosurgery Department, AIIMS with due consent from patients and ethical clearance obtained from the ethics committee of the institute. The tumor typing and grading was done by Prof Chitra Sarkar, Department of Pathology, AIIMS. Portions of the resected tumors were snap frozen in liquid nitrogen and stored at −80° C. until prior to RNA extraction. Of these 35 patients, 14 were female and 21 were male, age between 30-65 years with a mean age±s.d. of 43±12.2 years.

Statistical Analysis: All in-vitro experiments were performed in triplicate and repeated thrice. q-PCR for patient tumor samples were performed in triplicate. Differences were determined using Student's t-test, and p<0.05 was considered significant. Data are shown as the mean±s.d.

Example 2

FAT1 Knockdown Reduces Migration and Invasion of Glioma Cells

Figure 1:
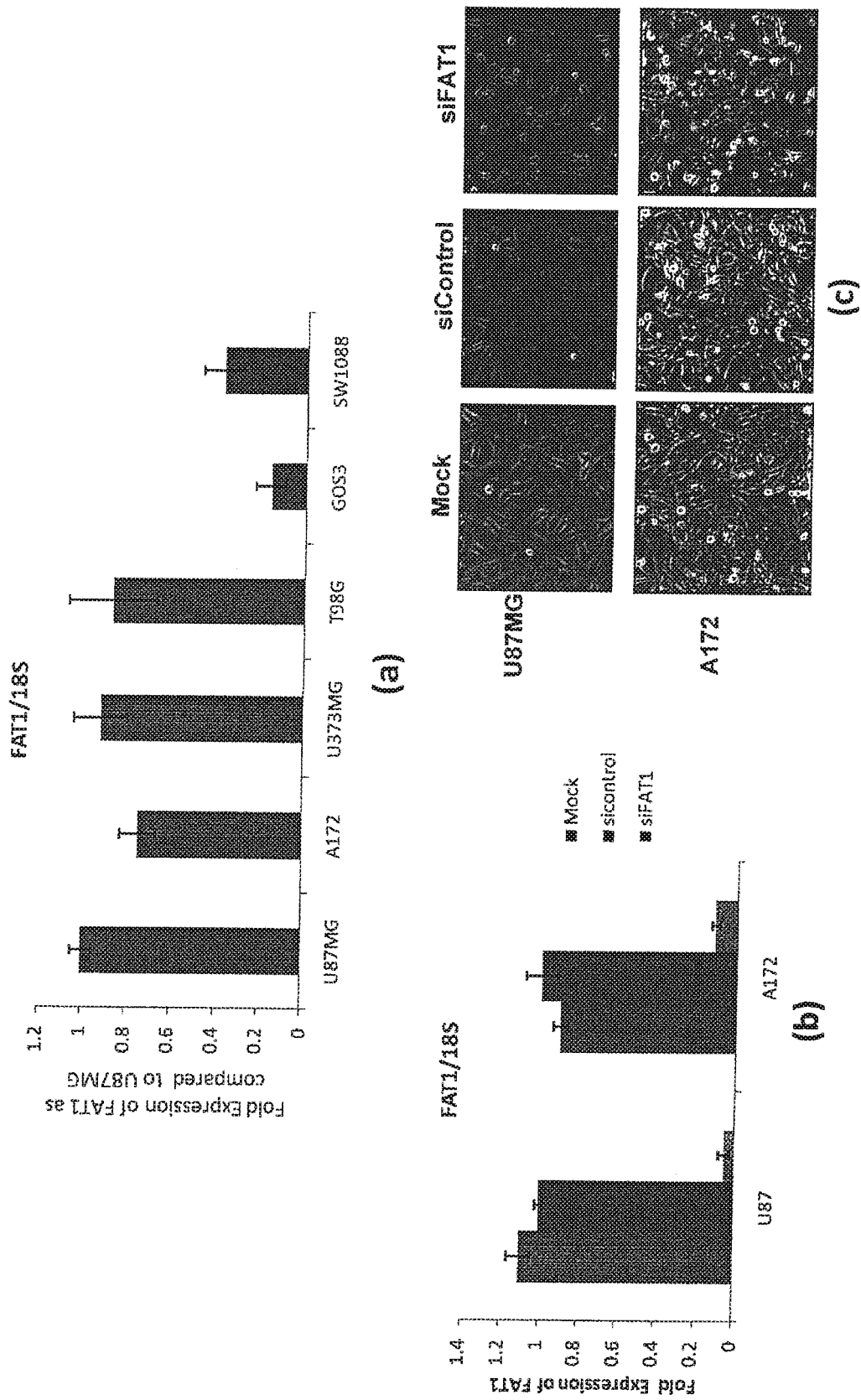
FIGS. 1A to 1E: Knockdown of FAT1 inhibited glioma cell migration and invasion.

FAT1 mRNA expression was checked in a panel of glioma cell lines and high FAT1 expression was observed in grade-IV glioma (GBM) cell lines (U87MG, A172, U373MG and T98G) as compared to grade-III glioma cell lines (GOS3 and SW1088) (FIG. 1a). The cell lines U87MG and A172 were studied further to analyze the effect of FAT1 knockdown. Knockdown efficiency of FAT1 in cells was checked by using a set of three FAT1 specific siRNA (details in materials and methods section) from Invitrogen and FAT1 siRNA I (HSS176716) was found to have maximum knockdown efficiency (FIG. S1, FIG. 7). FAT1 siRNA I was used for further experiments. 90% knockdown of FAT1 mRNA expression was observed in FAT1 siRNA treated (U87MGsiFAT1 and A172siFAT1) cells as compared to control siRNA (Invitrogen) treated (siControl) cells, 72 hrs post transfection (FIG. 1b). There were significant morphological alterations (cells were more spindly) in siFAT1 treated cells (FIG. 1c).

Significant reduction in migration [(>2 fold in U87MGsiFAT1 (P<0.01) and >3 fold in A172siFAT1 cells (P<0.001)] (FIG. 1d) as well as invasion [(>2 fold in U87MGsiFAT1 and >1.5 fold in A172siFAT1, P<0.01)] (FIG. 1e) was observed upon FAT1 knockdown. There was no variation in the distribution of cell population in different phases of cell cycle, as assessed by FACS analysis (FIG. 8a), as well as in cell viability as assessed by MTT (FIG. 8b), after FAT1 knockdown. Further, there was no DNA fragmentation (DAPI staining) and no cleaved caspase-3 (Western blot) after 72 hrs of transfection (FIG. 8c,d), indicating that FAT1 knockdown did not affect cell viability and apoptosis.

Example 3

FAT1 Knockdown Enhances PDCD4 Expression

In initial screening by microarray for altered gene expression after FAT1 knockdown in U87MG cell line, PDCD4 was identified as one of the up-regulated genes. This was further confirmed by q-PCR and Western blot analysis in 4 GBM cell lines, U87MG, A172, U373MG and T98G. There was 2.4, 2.8, 3.2 and 3.5 fold increase in PDCD4 mRNA expression (FIG. 2a) as well as increased PDCD4 protein level (FIG. 2b) in siFAT1 treated U87MG, A172, U373MG, and T98G cells respectively as compared to their respective siControl treated cells. The grade III glioma cell line, GOS3, with low endogenous FAT1 expression (FIG. 1a) had high PDCD4 mRNA expression (FIG. 2c), corroborating the inverse relationship between FAT1 and PDCD4.

The prior art teaches that phospho-Akt and PDCD4 negatively regulate each others' expression. However, to the contrary, in the present invention, increased phospho-Akt levels (FIG. 9) were observed along with increased PDCD4 expression (FIG. 2A, 2B) after FAT1 knockdown in U87MG cells, suggesting that increased PDCD4 expression after FAT1 knockdown was independent of p-Akt pathway.

Example 4

FAT1 Knockdown Diminishes AP-1 Mediated Transcription

Figure 3:
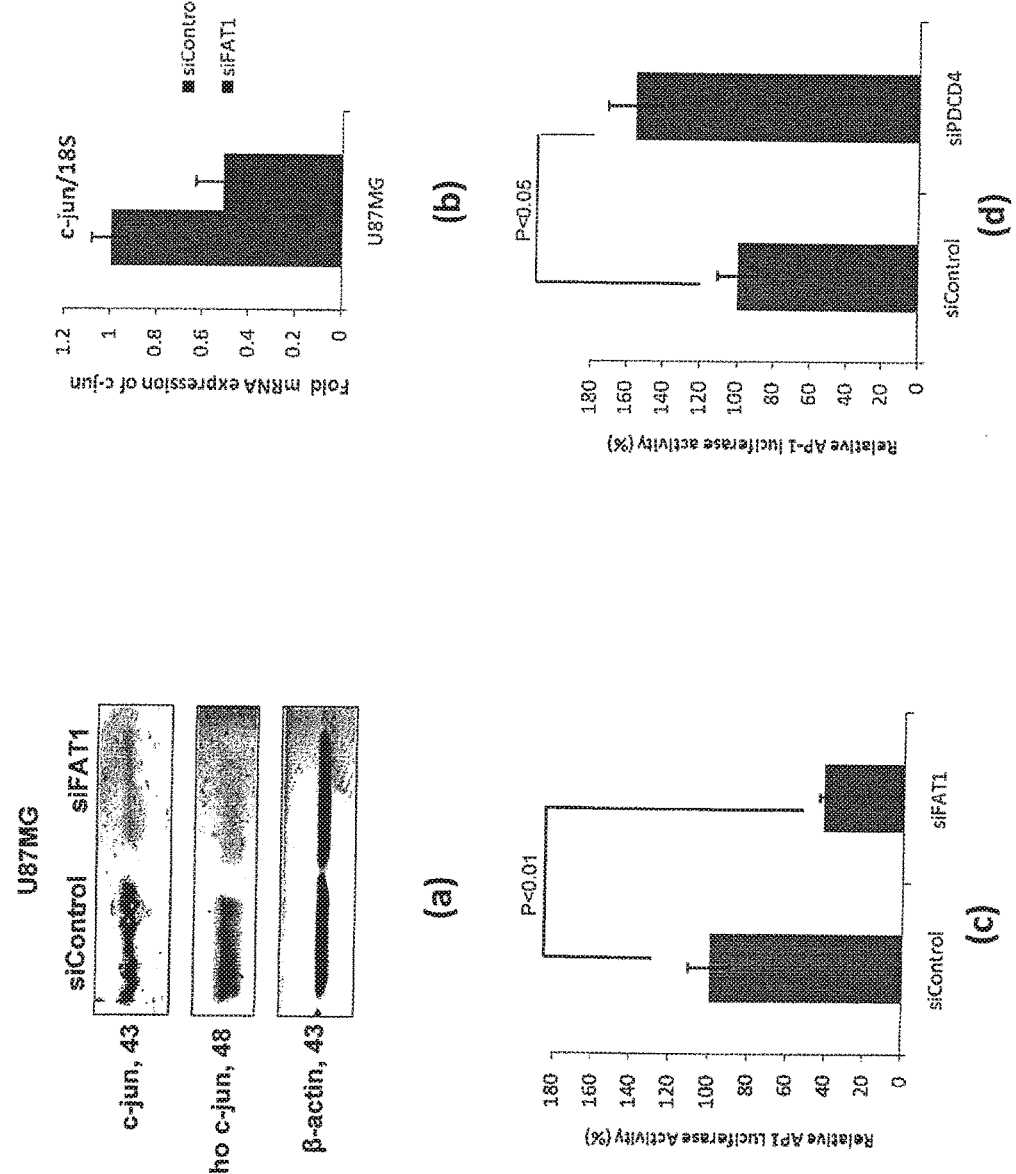

PDCD4 is reported to inhibit AP-1 dependent transcription via suppression of c-jun phosphorylation. Since c-jun phosphorylation is required for AP-1 activity, the effect of FAT1 knockdown on c-jun phosphorylation status was investigated by Western blotting and found to be significantly decreased along with reduction in the total c-jun protein level in U87MGsiFAT1 cells as compared to siControl cells (FIG. 3a). The c-jun mRNA level, as checked by q-PCR, was also found to be decreased by two folds in U87MGsiFAT1 cells as compared to U87MGsiControl cells (FIG. 3b). The reduction in the total c-jun protein level in U87MGsiFAT1 cells is due to reduction in the c-Jun mRNA level as well as ubiquitination and fast degradation of unphosphorylated c-jun.

Further, AP-1 luciferase assay was performed to examine whether the up-regulation of PDCD4 and diminished c-jun phosphorylation in siFAT1 cells has any effect on AP-1 activity. A 2-fold reduction ($p<0.01$) in AP-1 luciferase activity in U87MGsiFAT1 cells as compared to U87siControl cells (FIG. 3c) was observed. Moreover the mRNA expression of AP-1 target genes like MMP3, VEGF-C and PLAU (Urokinase) were found to be decreased by more than 10-fold (FIG. 10a) as well as decreased ECM protease activity (FIG. 10b), due to decreased MMP3, in U87MGsiFAT1 cells.

To further corroborate that PDCD4 regulates the AP-1 dependent transcription, PDCD4 was knocked down by using siPDCD4 in U87MG cells and observed 1.5 fold increase ($p<0.05$) in AP-1 luciferase activity (FIG. 3d) as well as increased expression of AP-1 target genes like COX-2, IL6 and IL143 (FIG. 3e) to add. Thus, confirming that increased PDCD4 expression after FAT1 knockdown attenuates AP-1 transcriptional activity via reduction in the level of phosphorylated c-jun.

Example 5

Knockdown of FAT1 Decreases the Expression of COX-2 and Other Cytokines

Figure 4:
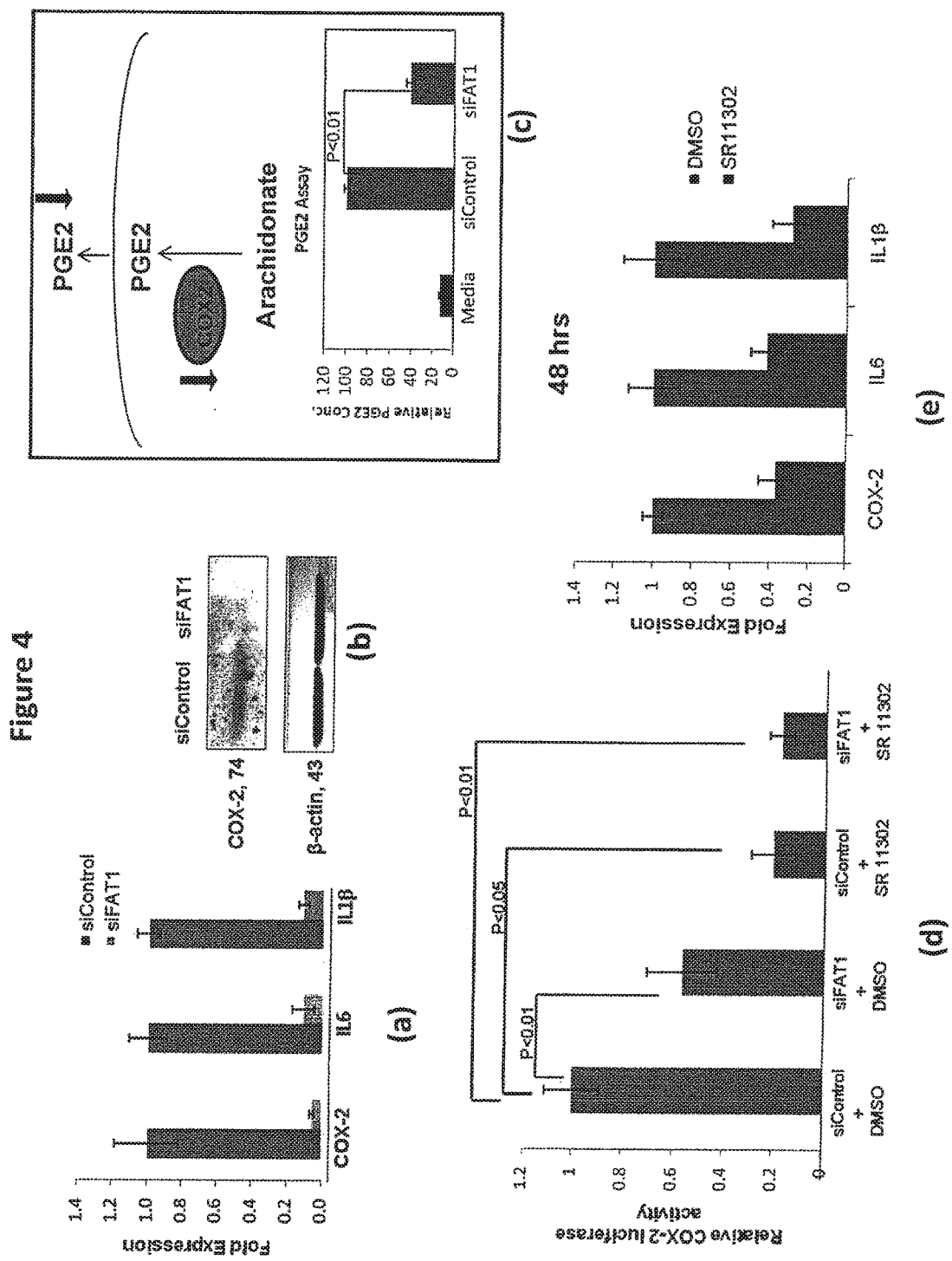

COX-2 is known to be negatively regulated by PDCD4 and aberrant induction of COX-2 with upregulation of prostaglandin synthesis is reported to play a pivotal role in carcinogenesis. COX-2 expression at mRNA and protein level was analyzed by q-PCR and Western blot. Significant reduction of COX-2 expression at both mRNA (FIG. 4a) and at protein level (FIG. 4b) in U87MGsiFAT1 cells was observed as compared to siControl cells. The enzymatic product of COX-2, prostaglandin E2 (PGE2) plays a key role in influencing tumor progression. The concentration of PGE2 secreted into the medium was found to be reduced by >2 fold in U87MGsiFAT1 cells as compared to siControl cells ($p<0.01$) (FIG. 4c). Thus this result depicts inhibition of COX-2 function leading to diminished PGE2 synthesis after FAT1 knockdown.

COX-2 has also been reported to regulate endogenous cytokine production and its inhibition markedly reduces the release of pro-inflammatory cytokines like IL-1β and IL-6. A significant reduction in mRNA expression of COX-2 was also observed along with IL-1β and IL-6 after FAT1 knockdown in U87MG cells (FIG. 4a), thus identifying a novel function of FAT1 in regulating the expression of pro-inflammatory molecules.

AP-1 mediated regulation of COX-2 transcription has been reported. To investigate whether the regulation of COX-2 expression by FAT1 in U87MG cells is mediated via AP-1, AP-1 activity was inhibited by treating cells to the specific small molecule inhibitor of AP-1, SR 11302. On treating U87MG cells to increasing concentration of SR11302 (0.1 μM to 10 μM), a dose dependent decrease in COX-2 luciferase activity was observed, with a maximum inhibition of about 90% at the dose of 5 μM and 10 μM concentrations (FIG. 11). An 1.8 fold decrease ($p<0.01$), 5 fold decrease ($p<0.05$) and 5.5 fold decrease ($p<0.01$) was observed in COX-2 luciferase activity after siFAT1, 48 hrs SR11302 and simultaneous siFAT1+SR11302 treatment respectively as compared to siControl+DMSO treated U87MG cells (FIG. 4d). To further confirm that AP-1 activity was indeed inhibited by SR11302, the mRNA level of COX-2, IL1β and IL6 was checked by q-PCR and found to be markedly reduced on treatment with 10 μM of SR11302 (FIG. 4e). These results thus provide further supportive evidence that AP-1 is a key link in the regulation of expression of COX-2 and other cytokines.

Example 6

Figure 5:
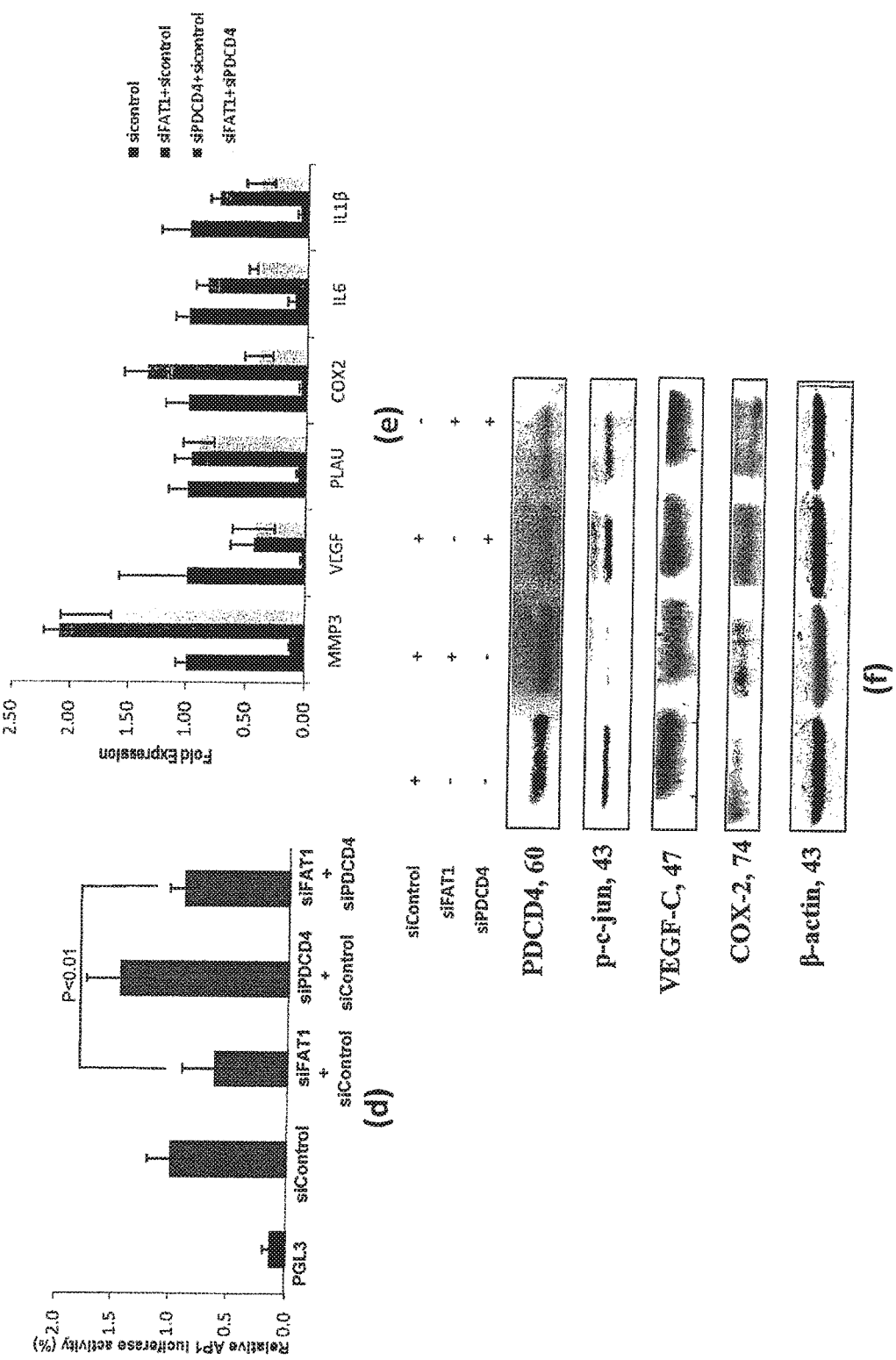

Inhibition of PDCD4 Reverses the Effects of FAT1 Knockdown in FAT1 Attenuated Cells To confirm that the demonstrated effects of FAT1 knockdown were indeed due to the up-regulation of PDCD4, FAT1 and PDCD4 siRNA were co-transfected in U87MG cells and could satisfactorily knockdown levels of both the genes simultaneously. Simultaneous knockdown of both the genes (FIG. 5a) restored migration and invasion of cells to that of the level of siControl (FIG. 5b,5c). Moreover, AP-1 luciferase activity as well as the expression of AP-1 target genes was significantly regained with simultaneous PDCD4 inhibition in U87MGsiFAT1 cells (FIG. 5d,5e). At protein level, simultaneous knockdown of PDCD4 and FAT1 in U87MG cell line resulted in decreased PDCD4 expression to the level in siControl cells, but the expression of p-c-jun, VEGF-C and COX-2 was regained (FIG. 5f). Interestingly, U87MG cells knocked down for PDCD4 alone showed increased migration and invasion (FIG. 5b,5c) and high AP-1 luciferase activity (FIG. 5d) as compared to siControl cells. Low expression of AP-1 regulated transcripts in GOS3 cell line (FIG. 12) which has low FAT1 and high PDCD4 expression (FIG. 2c) was also observed. These results confirm the role of PDCD4 in mediating the observed effects of FAT1.

Example 7

FAT1 and PDCD4 Expression is Inversely Correlated in Primary GBM Samples

PDCD4 expression is reported to be lost in human glioma and may contribute to the development of tumor. To study the relationship between FAT1 and PDCD4 expression in tumors, the mRNA expression of both FAT1 and PDCD4 was checked in 35 GBM samples by q-PCR (Table 2).

TABLE 2

Expression analysis of FAT1, PDCD4, COX-2 and IL6 in human GBM samples by q-PCR. GBM samples were divided into four groups (group A, B, C and D) based on quartiles showing decreasing FAT1 expression. The PDCD4 expression (mean ± SD) in the group A and group D were calculated (0.586 ± 0.998 and 60.856 ± 50.209 respectively) and the difference in the two groups were found to be statistically significant (p = 0.0145). Similarly, on comparing the expression of COX-2 in group A and group D, there was a significant positive correlation between FAT1 and the COX-2 expression, with the mean ± SD of Group A and D being 4.99 ± 4.074 and 0.248 ± 0.174 respectively (p = 0.048). For IL6, there was a similar positive trend between Group A and D however it was not statistically significant (p = 0.146).

| Group | Samples | FAT1/18s | PDCD4/18s | COX-2/18S | IL6/18S |
| --- | --- | --- | --- | --- | --- |
| Group A | GBM10 | 70.560 | 3.160 | 1.765 | 80.171 |
| | GBM35 | 34.844 | 0.774 | 6.821 | 18.189 |
| | GBM11 | 19.990 | 0.438 | 8.168 | 5.152 |
| | GBM8 | 19.490 | 0.430 | 1.905 | 0.020 |
| | GBM24 | 13.990 | 0.004 | 2.346 | 3.238 |
| | GBM30 | 13.707 | 0.056 | 0.006 | 0.067 |
| | GBM25 | 8.138 | 0.002 | 0.387 | 1.597 |
| | GBM6 | 5.980 | 0.303 | 14.929 | 12.862 |
| | GBM5 | 5.290 | 0.112 | 0.337 | 1.834 |
| Group B | GBM12 | 4.700 | 0.555 | 0.742 | 25.020 |
| | GBM7 | 4.660 | 10.754 | 1.778 | 4.302 |
| | GBM31 | 4.000 | 0.176 | 0.056 | 0.034 |
| | GBM33 | 3.949 | 0.290 | 0.143 | 0.155 |
| | GBM2 | 2.479 | 0.100 | 0.100 | 0.372 |
| | GBM32 | 1.548 | 0.195 | 0.158 | 0.509 |
| | GBM29 | 1.500 | 134.809 | 0.001 | 3.340 |
| | GBM28 | 1.300 | 1.372 | 0.001 | 0.963 |
| | GBM27 | 1.200 | 0.333 | 1.892 | 2.514 |
| Group C | GBM1 | 0.034 | 0.000 | 0.014 | 1.279 |
| | GBM23 | 0.007 | 0.003 | 0.002 | 0.003 |
| | GBM21 | 0.006 | 0.001 | 0.001 | 74.028 |
| | GBM34 | 0.006 | 0.002 | 0.010 | 73.262 |
| | GBM4 | 0.003 | 0.000 | 0.007 | 3.494 |
| | GBM13 | 0.003 | 0.000 | 0.702 | 4.332 |
| | GBM3 | 0.002 | 0.000 | 0.611 | 3.399 |
| | GBM22 | 0.002 | 0.002 | 0.010 | 0.081 |
| Group D | GBM9 | 0.001 | 0.000 | 1.347 | 0.232 |
| | GBM14 | 0.001 | 0.000 | 0.030 | 8.545 |
| | GBM15 | 0.001 | 0.000 | 0.004 | 0.838 |
| | GBM16 | 0.001 | 43.633 | 0.120 | 0.041 |
| | GBM17 | 0.001 | 40.818 | 0.058 | 0.007 |
| | GBM18 | 0.001 | 106.912 | 0.743 | 0.226 |
| | GBM19 | 0.001 | 82.124 | 0.009 | 0.004 |
| | GBM20 | 0.001 | 69.487 | 0.140 | 0.009 |
| | GBM26 | 0.001 | 143.998 | 0.288 | 0.017 |

The 35 GBM samples were arranged according to decreasing FAT1 expression and divided into quartiles. The PDCD4 expression (mean value±standard deviation) in the first quartile (group A) with highest FAT1 expression (0.586±0.998) was significantly less than in the fourth quartile (group D) with the lowest FAT1 expression (54.108±51.18), with p=0.0145. The inverse relationship observed between the expression of FAT1 and PDCD4 in tumor samples supports the in-vitro results.

Further, the mRNA expression of COX-2 and IL6 in these GBM samples was also analyzed and positive correlation with FAT1 expression observed. The COX-2 expression in group A (4.99±4.074) was significantly high as compared to group D (0.248±0.174) with p=0.048. The IL6 expression in group A (mean±SD) and group D (Mean±SD) were found to follow the similar trend, however it was not statistically significant (p=0.146).

Example 8

Simultaneous Knockdown of FAT1 Expression and Inhibition of COX2 Result in Greater Inhibition of Cell Migration than Either Treatment Alone The Scratch Assay was performed on U87MG cells as described above. Migration of the cells was shown to be inhibited by about 50% by siRNA against FAT1 or by about 70% by the COX2 inhibitor NS398. Migration of the cells was inhibited even further (about 90%) by the administration of both inhibitors together. The effect of NS398 is more pronounced when the cells are cultured under hypoxic conditions.

What is claimed is:

1. A method of reducing the invasiveness into extracellular matrix of a tumor cell or of reducing migration of a tumor cell, said tumor cell overexpressing FAT1, comprising contacting said cell with or administering to said subject a pharmaceutical composition comprising a siRNA inhibitor of FAT1 expression or FAT1 activity, said siRNA inhibitor comprising the nucleotide sequence of SEQ ID NO: 2 and SEQ ID NO: 3.

2. The method of claim 1, further comprising:
   i) assaying the activity of FAT1 and AP1 in said subject;
   ii) comparing the activity of FAT1 and AP1 in said subject with the activities of FAT1 and AP1 in normal subjects, and identifying as a subject one that would benefit from treatment a subject having activity of FAT1 and of AP1 higher than the activity of FAT1 and AP1 in normal subjects; and
   iii) contacting a cell or tissue of said subject expressing FAT1 and AP1 at a high level with a candidate drug/active molecule;
   iv) optionally contacting said cell or tissue expressing FAT1 and AP1 at a high level with an inhibitor of COX2 activity prior to or at the same time as step iii) is performed;
   v) comparing the level of expression of FAT1 in the cells or tissue contacted with the candidate drug/active molecule with the level of expression of FAT1 in said cells or tissue not contacted with the candidate drug/active molecule;
   vi) selecting as a suitable anticancer/anti-inflammatory drug a candidate drug/active molecule for which cells contacted with the candidate drug/active molecule exhibit lower expression of FAT1 than cells not contacted with the candidate drug/active molecule; and
   vii) administering to said subject that would benefit from treatment a pharmaceutical composition comprising said suitable anticancer/anti-inflammatory drug.

3. The method of claim 1, wherein the siRNA is a double-stranded RNA having a nucleotide sequence that is a portion of SEQ ID NO: 1.

4. The method of claim 2, in which the cancer is a glioma.

5. The method of claim 2, wherein the activity of FAT1 is assayed by RT-PCR.

6. The method of clam 2, wherein the activity of AP1 is assayed by RT-PCR.

7. The method of claim 2, wherein the siRNA is a double-stranded RNA having a nucleotide sequence that is a portion of SEQ ID NO: 1.

8. The method of claim 4, in which the glioma is glioblastoma multiforme.

9. The method of claim 1, that further comprises administering a composition comprising a COX2 inhibitor.

10. The method of claim 2, wherein the step vii) further comprises administering a COX2 inhibitor.

11. The method of claim 1, in which the cancer is a glioma.

12. The method of claim 11, in which the glioma is glioblastoma multiforme.

13. The method of claim 11, that further comprises administering a composition comprising a COX2 inhibitor.

14. A method of reducing the invasiveness into extracellular matrix of glioma cell or of reducing migration of a glioma cell, said glioma cell over-expressing FAT1, comprising contacting said cell with or administering to said subject a pharmaceutical composition comprising a siRNA inhibitor of FAT1 expression or FAT1 activity, wherein the siRNA is a double-stranded RNA having a nucleotide sequence that is a portion of SEQ ID NO: 1.

15. The method of claim 14, that further comprises administering a composition comprising a COX2 inhibitor.

* * * * *

SEQUENCE LISTING

```
<160> NUMBER OF SEQ ID NOS: 30

<210> SEQ ID NO 1
<211> LENGTH: 13767
<212> TYPE: DNA
<213> ORGANISM: Homo sapiens
<220> FEATURE:
<221> NAME/KEY: FAT1GENE
<222> LOCATION: (1)..(13767)
```

<400> SEQUENCE: 1

```
atggggagac atttggcttt gctcctgctt ctgctccttc tcttccaaca ttttggagac    60
agtgatggca gccaacgact tgaacagact cctctgcagt ttacacacct cgagtacaac   120
gtcaccgtgc aggagaactc tgcagctaag acttatgtgg ggcatcctgt caagatgggt   180
gtttacatta cacatccagc gtgggaagta aggtacaaaa ttgtttccgg agacagtgaa   240
aacctgttca agctgaaga gtacattctc ggagactttt gctttctaag aataaggacc   300
aaaggaggaa atacagctat tcttaataga gaagtgaagg atcactacac attgatagtg   360
aaagcacttg aaaaaaatac taatgtggag gcgcgaacaa aggtcagggt gcaggtgctg   420
gatacaaatg acttgagacc gttattctca cccacctcat acagcgtttc tttacctgaa   480
aacacagcta taaggaccag tatcgcaaga gtcagcgcca cggatgcaga cataggaacc   540
aacgggaat tttactacag ttttaaagat cgaacagata tgtttgctat tcacccaacc   600
agtggtgtga tagtgttaac tggtagactt gattacctag agaccaagct ctatgagatg   660
gaaatcctcg ctgcggaccg tggcatgaag ttgtatggga gcagtggcat cagcagcatg   720
gccaagctaa cggtgcacat cgaacaggcc aatgaatgtg ctccggtgat aacagcagtg   780
acattgtcac catcagaact ggacagggac ccagcatatg caattgtgac agtggatgac   840
tgcgatcagg gtgccaatgg tgacatagca tctttaagca tcgtggcagg tgaccttctc   900
cagcagttta gaacagtgag gtcctttcca gggagtaagg agtataaagt caaagccatc   960
ggtggcattg attgggacag tcatcctttc ggctacaatc tcacactaca ggctaaagat  1020
aaaggaactc cgccccagtt ctcttctgtt aaagtcattc acgtgacttc tccacagttc  1080
aaagccgggc cagtcaagtt tgaaaaggat gtttacagag cagaaataag tgaatttgct  1140
cctcccaaca cacctgtggt catggtaaag gccattcctg cttattccca tttgaggtat  1200
gttttaaaa gtacacctgg aaaagctaaa ttcagtttaa attacaacac tggtctcatt  1260
tctattttag aaccagttaa aagacagcag gcagcccatt ttgaacttga agtaacaaca  1320
agtgacagaa aagcgtccac caaggtcttg gtgaaagtct taggtgcaaa tagcaatccc  1380
cctgaattta cccagacagc gtacaaagct gcttttgatg agaacgtgcc cattggtact  1440
actgtcatga gcctgagtgc cgtagaccct gatgagggtg agaacgggta cgtgacatac  1500
agtatcgcaa atttaaatca tgtgccgttt gcgattgacc atttcactgg tgccgtgagt  1560
acgtcagaaa acctggacta cgaactgatg cctcgggttt atactctgag gattcgtgca  1620
tcagactggg gcttgccgta ccgccgggaa gtcgaagtcc ttgctacaat tactctcaat  1680
aacttgaatg acaacacacc tttgtttgag aaaataaatt gtgaagggac aattcccaga  1740
gatctaggcg tgggagagca ataaccact gtttctgcta ttgatgcaga tgaacttcag  1800
ttggtacagt atcagattga agctggaaat gaactggatt tctttagttt aaaccccaac  1860
tcggggtat tgtcattaaa gcgatcgcta atggatggct taggtgcaaa ggtgtctttc  1920
cacagtctga gaatcacagc tacagatgga gaaaattttg ccacaccatt atatatcaac  1980
ataacagtgg ctgccagtca caagctggta aacttgcagt gtgaagagac tggtgttgcc  2040
aaaatgctgg cagagaagct cctgcaggca aataaattac acaaccaggg agaggtggag  2100
gatattttct tcgattctca ctctgtcaat gctcacatac cgcagtttag aagcactctt  2160
ccgactggta ttcaggtaaa ggaaaaccag cctgtggggtt ccagtgtaat tttcatgaac  2220
tccactgacc ttgacactgg cttcaatgga aaactggtct atgctgtttc tggaggaaat  2280
gaggatagtt gcttcatgat tgatatggaa acaggaatgc tgaaaatttt atctcctctt  2340
```

```
gaccgtgaaa caacagacaa atacaccctg aatattaccg tctatgacct tgggataccc    2400
cagaaggctg cgtggcgtct tctacatgtc gtggttgtcg atgccaatga taatccaccc    2460 gagttttac aggagagcta ttttgtggaa gtgagtgaag acaaggaggt acatagtgaa     2520
atcatccagg ttgaagccac agataaagac ctggggccca acggacacgt gacgtactca    2580
attgttacag acacagacac attttcaatt gacagcgtga cgggtgttgt taacatcgca    2640
cgccctctgg atcgagagct gcagcatgag cactccttaa agattgaggc cagggaccaa    2700
gccagagaag agcctcagct gttctccact gtcgttgtga agtatcact agaagatgtt     2760 aatgacaacc cacctacatt tattccacct aattatcgtg tgaaagtccg agaggatctt    2820
ccagaaggaa ccgtcatcat gtggttagaa gcccacgatc ctgatttagg tcagtctggt    2880
caggtgagat acagccttct ggaccacgga gaaggaaact tcgatgtgga taaactcagt    2940
ggagcagtta ggatcgtcca gcagttggac tttgagaaga agcaagtgta atctcact     3000 gtgagggcca aagacaaggg aaagccagtt tctctgtctt ctacttgcta tgttgaagtt    3060
gaggtggttg atgtgaatga gaacctgcac ccacccgtgt tttccagctt tgtggaaaag    3120
gggacagtga agaagatgc acctgttggt tcattggtaa tgacggtgtc ggctcatgat     3180
gaggacgcca agagatgg ggagatccga tactccatta gagatggctc tggcgttggt      3240
gttttcaaaa taggtgaaga acaggtgtc atagagacgt cagatcgact ggaccgtgaa     3300
tcgacctccc attattggct aacagtcttt gcaaccgatc agggtgtcgt gcctctttca    3360
tcgttcatag agatctacat agaggttgag gatgtcaatg acaatgcacc acagacatca    3420
gagcctgttt attcccaga aatcatggaa aattctccta aagatgtatc tgtggtccag     3480
atcgaggcat ttgatccaga ttcgagctct aatgacaagc tcatgtacaa aattacaagt    3540
ggaaatccac aaggattctt ttcaatacat cctaaaacag gtctcatcac aactacgtca    3600
aggaagctag accgagaaca gcaagatgaa cacatattag aggttactgt gacagacaat    3660
ggtagtcccc ccaaatcaac cattgcaaga gtcattgtga aaatccttga tgaaaatgac    3720
aacaaacctc agtttctgca aaagttctac aaaatcagac tccctgagcg ggaaaagcca    3780
gaccgagaaa gaaatgccag acgggagccg ctctatcacg tcatagccac cgacaaggat    3840
gagggcccca atgcagaaat ctcctacagc atcgaagacg ggaatgagca tggcaaattt    3900
ttcatcgaac cgaaaactgg agtggtttcg tccaagaggt tttcagcagc tggagaatat    3960
gatattcttt caattaaggc agttgacaat ggtcgccctc aaaagtcatc aaccaccaga    4020
ctccatattg aatggatctc caagcccaaa ccgtccctgg agcccatttc atttgaagaa    4080 tcattttta cctttactgt gatggaaagt gaccccgttg ctcacatgat tggagtaata    4140
tctgtggagc ctcctggcat accccttggg tttgacatca ctggtggcaa ctacgacagt    4200
cacttcgatg tggacaaggg aactggaacc atcattgttg ccaaacctct tgatgcagaa    4260
cagaagtcaa actacaacct cacagtcgag gctacagatg gaaccaccac tatcctcact    4320
caggtattca tcaaagtaat agacacaaat gaccatcgtc ctcagttttc tacatcaaag    4380
tatgaagttg ttattcctga agatacagcg ccagaaacag aaattttgca aatcagtgct    4440
gtggatcagg atgagaaaaa caaactaatc tacactctgc agagcagtag agatccactg    4500
agtctcaaga aatttcgtct tgatcctgca accggctctc tctatacttc tgagaaactg    4560
gatcatgaag ctgttcacca gcacaccctc acggtcatgg tacgagatca agatgtgcct    4620
gtaaaacgca actttgcaag gattgtggtc aatgtcagcg acacgaatga ccacgccccg    4680
```

```
tggttcaccg cttcctccta caaagggcgg gtttatgaat cggcagccgt tggctcagtt    4740
gtgttgcagg tgacggctct ggacaaggac aaagggaaaa atgctgaagt gctgtactcg    4800
atcgagtcag gaaatattgg aaattctttt atgattgatc ctgtcttggg ctctattaaa    4860
actgccaaag aattagatcg aagtaaccaa gcggagtatg atttaatggt aaaagctaca    4920
gataagggca gtccaccaat gagtgaaata acttctgtgc gtatctttgt cacaattgct    4980
gacaacgcct ctccgaagtt tacatcaaaa gaatattctg ttgaacttag tgaaactgtc    5040
agcattggga gtttcgttgg atggttaca  gcccatagtc aatcatcagt ggtgtatgaa    5100
ataaaagatg aaatacagg  tgatgctttt gatattaatc cacattctgg aactatcatc    5160
actcagaaag ccctggactt tgaaactttg cccatttaca cattgataat acaaggaact    5220
aacatggctg gtttgtccac taatacaacg gttctagttc acttgcagga tgagaatgac    5280
aacgcgccag tttttatgca ggcagaatat acaggactca ttagtgaatc agcctcaatt    5340
aacagcgtgg tcctaacaga caggaatgtc ccactggtga ttcgagcagc tgatgctgat    5400
aaagactcaa atgctttgct tgtatatcac attgttgaac catctgtaca cacatatttt    5460
gctattgatt ctagcactgg tgctattcat acagtactaa gtctggacta tgaagaaaca    5520
agtatttttc actttaccgt ccaagtgcat gacatgggaa ccccacgttt atttgctgag    5580
tatgcagcga atgtaacagt acatgtaatt gacattaatg actgcccccc tgtgtttgcc    5640
aagccattat atgaagcatc tcttttgtta ccaacataca aggagtaaa  agtcatcaca    5700 gtaaatgcta cagatgctga ttcaagtgca ttctcacagt tgatttactc catcaccgaa    5760
ggcaacatcg gggagaagtt ttctatggac tacaagactg tgctctcac  tgtccaaaac    5820 acaactcagt taagaagccg ctacgagcta accgttagag cttccgatgg cagatttgcc    5880
ggccttacct ctgtcaaaat taatgtgaaa gaaagcaaag aaagtcacct aaagtttacc    5940
caggatgtct actctgcggt agtgaaagag aattccaccg aggccgaaac attagctgtc    6000
attactgcta ttgggaatcc aatcaatgag cctttgtttt atcacatcct caacccagat    6060
cgcagattta aaataagccg cacttcagga gttctgtcaa ccactggcac gcccttcgat    6120
cgtgagcagc aggaggcgtt tgatgtggtt gtagaagtga cagaggaaca taagccttct    6180
gcagtggccc acgttgtcgt gaaggtcatt gtagaagacc aaaatgataa tgcgccggtg    6240
tttgtcaacc ttccctacta cgccgttgtt aaagtggaca ctgaggtggg ccatgtcatt    6300
cgctatgtca ctgctgtaga cagagacagt ggcagaaacg gggaagtgca ttactacctc    6360
aaggaacatc atgaacactt tcaaattgga cccttgggtg aaatttcact gaaaaagcaa    6420
tttgagcttg acaccttaaa taaagaatat cttgttacag tggttgcaaa agatggaggg    6480
aacccggcct tttcagcgga agttatcgtt ccgatcactg tcatgaataa agccatgcct    6540
gtgtttgaaa aacctttcta cagtgcagag attgcagaga gcatccaggt gcacagccct    6600
gtggtccacg tgcaggctaa cagcccggaa ggcctgaaag tgttctacag catcacagac    6660
ggagaccctt tcagccagtt cactattaac ttcaatactg gagttatcaa tgtcatagct    6720
cctctggact ttgaggccca cccggcatat aagctgagca tacgcgcaac tgactccttg    6780
acgggcgctc atgctgaagt attttgtggac atcatagtag acgacatcaa tgataaccct    6840
cctgtgtttg ctcagcagtc ttatgcggtg accctgtctg aggcatctgt aattggaacg    6900
tctgttgttc aagttagagc caccgattct gattcagaac caaatagagg aatctcatac    6960
cagatgtttg ggaatcacag caagagtcat gatcattttc atgtagacag cagcactggc    7020
ctcatctcac tactcagaac cctggattac gagcagtccc ggcagcacac gattttgtg    7080
```

```
agggcagttg atggtggtat gcccacgctg agcagtgatg tgattgtcac ggtggacgtt    7140
accgacctca atgataatcc accactcttt gaacaacaga tttatgaagc cagaattagc    7200
gagcacgccc ctcatgggca tttcgtgacc tgtgtaaaag cctatgatgc agacagttca    7260
gacatagaca agttgcagta ttccattctg tctggcaatg atcataaaca ttttgtcatt    7320
gacagtgcaa cagggattat caccctctca aacctgcacc ggcacgccct gaagccattt    7380
tacagtctta acctgtcagt gtctgatgga gttttagaa gttccaccca ggttcatgta    7440
actgtaattg gaggcaattt gcacagtcct gctttccttc agaacgaata tgaagtggaa    7500
ctagctgaaa acgctcccct acatacctg gtgatggagg tgaaaactac ggatggggat    7560
tctggtattt atggtcacgt tacttaccat attgtaaatg actttgccaa agacagattt    7620
tacataaatg agagaggaca gatatttact ttggaaaaac ttgatcgaga accccggcg    7680 gagaaagtga tctcagtccg tttaatggct aaggatgctg aggaaaagt tgctttctgc    7740 accgtgaatg tcatccttac agatgacaat gacaatgcac cacaatttcg agcaaccaaa    7800
tacgaagtga atatcgggtc cagtgctgct aaagggactt cagtcgttaa agttcttgca    7860
agtgatgccg atgagggctc caatgccgac atcacctatg ccattgaagc agactctgaa    7920
agtgtaaaag agaatttgga aattaacaaa ctgtccggcg taatcactac aaaggagagc    7980
ctcattggct tggaaaatga atcttcact ttctttgtta gagctgtgga taatgggtct    8040
ccatcaaaag aatctgttgt tcttgtctat gttaaaatcc ttccaccgga aatgcagctt    8100
ccaaaatttt cagaaccttt ctatacctt acagtgtcag aggacgtgcc tattggaaca    8160
gagatagatc tcatccgagc agaacatagt gggactgttc tttacagcct ggtcaaaggg    8220
aatactccag aaagcaatag ggatgagtcc tttgtgattg acagacagag cgggagactg    8280
aagttggaga agagtcttga tcatgagaca actaagtggt atcagttttc catactggcc    8340
aggtgcactc aagatgacca tgagatggtg gcttctgtag atgttagtat ccaagtgaaa    8400
gatgcaaatg acaacagccc ggtctttgaa tctagtccat atgaggcatt cattgttgaa    8460
aacctgccag ggggaagtag agtaattcag atcagggcat ctgatgctga ctcaggaacc    8520
aacggccaag ttatgtatag cctggatcag tcacaaagtg tggaagtcat tgaatccttt    8580
gccattaaca tggaaacagg ctggattaca actttaaagg aacttgacca tgaaaagaga    8640
gacaattacc agattaaagt ggttgcatca gatcatggtg aaaagatcca gctatcctcc    8700
acagccattg tggatgttac cgtcaccgat gtcaacgata gtccaccacg attcacggcc    8760
gagatctata aagggactgt gagtgaggat gaccccaag gtggggtgat gccatctta    8820 agtaccacgg atgctgattc tgaagagatc aacagacaag ttacatattt cataacagga    8880 gggggatcctt taggacagtt tgccgttgaa actatacaga tgaatggaa ggtatatgtg    8940 aagaaacctc tagacaggga aaaagggac aattaccttc ttactatcac ggcaactgat    9000
ggcaccttct catcaaaagc gatagttgaa gtgaaagttc tggatgcaaa tgacaacagt    9060
ccagtttgtg aaaagacttt atattcagac actattcctg aagacgtcct tcctggaaaa    9120
ttgatcatgc agatctctgc tacagacgca gacatccgct ctaacgctga aattacttac    9180
acgttattgg gttcaggtgc agaaaaattc aaactaaatc cagacacagg tgaactgaaa    9240
acgtcaaccc cccttgatcg tgaggagcaa gctgttttatc atcttctcgt cagggccaca    9300
gatgagggag gaagattctg ccaagccagt attgtgctca cgctagaaga tgtgaacgat    9360
aacgcccccg aattctctgc cgatccttat gccatcaccg tgtttgaaaa cacagagccg    9420
```

```
ggaacgctgc tgacaagagt gcaggccaca gatgccgacg caggattaaa tcggaagatt    9480
ttatactcac tgattgactc tgctgatggg cagttctcca ttaacgaatt atctggaatt    9540
attcagttag aaaaaccttt ggacagagaa ctccaggcag tatacaccct ctctttgaaa    9600
gctgtggatc aaggcttgcc aaggaggctg actgccactg gcactgtgat tgtatcagtt    9660
cttgacataa atgacaaccc ccctgtgttt gagtaccgtg aatatggtgc caccgtgtct    9720
gaggacattt tgttggaac tgaagttctt caagtgtatg cagcaagtcg ggatattgaa     9780
gcaaatgcag aaatcaccta ctcaataata agtggaaatg aacatgggaa attcagcata    9840
gattctaaaa caggggccgt atttatcatt gagaatctgg attatgagag ctctcatgag    9900
tattacctaa cagtagaggc cactgatgga ggcacgcctt cactgagcga cgttgccact    9960
gtgaacgtta atgtaacaga tatcaacgat aatacccctg tgttcagcca agacacctac   10020
acgacagtca tcagtgaaga tgccgttctt gagcagtctg tcatcacggt tatggccgat   10080
gatgccgatg gaccttccaa cagccacatc cactactcaa ttatagatgg caaccaagga   10140
agctcgttca caattgaccc cgtcagggga gaagtcaaag tgaccaaact tctcgaccga   10200
gaaacgattt caggttacac gctcacggtt caagcttctg ataatggcag tccacccaga   10260
gtcaacacga cgaccgtgaa catcgatgtg tccgatgtca atgacaacgc gcccgtcttc   10320
tccaggggaa actacagtgt cattatccag gaaataagc cagtgggctt cagcgtgctg    10380
cagctggtag taacagatga ggattcttcc cataacggtc cacccttctt ctttactatt   10440
gtaactggaa atgatgagaa ggcttttgaa gttaacccgc aaggagtcct cctgacatca   10500
tctgccatca gaggaagga gaaagatcat tacttactgc aggtgaaggt ggcagataat    10560
ggaaagcctc agttgtcatc tttgacatac attgacatta gggtaattga ggagagcatc   10620
tatccgcctg cgattttgcc cctggagatt ttcatcacct cttctggaga agaatactca   10680
ggtggcgtca ttgggaagat ccatgccaca gaccaggacg tgtatgatac tctaacctac   10740
agtctcgacc ctcagatgga caacctgttc tctgtttcca gcacagggg caagctgata    10800
gcacacaaaa agctagacat agggcaatac cttctcaatg tcagcgtaac agatgggaag   10860
ttcacgacgg tggccgacat cacagtgcat atcagacaag tcacacagga gatgttgaac   10920
cacaccatcg cgatccgctt tgccaacctc actccggaag aattcgttgg tgactactgg   10980
cgcaacttcc agcgagcttt acggaacatc ctgggtgtga ggaggaacga catacagatt   11040
gttagtttgc agtcctctga acctcacccca catctggacg tcttactttt tgtagagaaa   11100
ccaggtagtg ctcagatctc aacaaaacaa cttctgcaca agattaactc ttccgtgact   11160
gacattgagg aaatcattgg agttaggata ctgaatgtat tccagaaact ctgcgcggga   11220
ctggactgcc cctggaagtt ctgcgatgaa aaggtgtctg tggatgaaag tgtgatgtca   11280
acacacagca cagccagact gagttttgtg actccccgcc accacagggc agcggtgtgt   11340
ctctgcaaag agggaaggtg cccacctgtc caccatggct gtgaagatga tccgtgccct   11400
gagggatccg aatgtgtgtc tgatccctgg gaggagaaac acacctgtgt ctgtcccagc   11460
ggcaggtttg gtcagtgccc agggagttca tctatgacac tgactggaaa cagctacgtg   11520
aaataccgtc tgacggaaaa tgaaaacaaa ttagagatga aactgaccat gaggctcaga   11580
acatattcca cgcatgcggt tgtcatgtat gctcgaggaa ctgactatag catcttggag   11640
attcatcatg gaaggctgca gtacaagttt gactgtggaa gtggccctgg aattgtctct   11700
gttcagagca ttcaggtcaa tgatgggcag tggcacgcag tggccctgga agtgaatgga   11760
aactatgctc gcttggttct agaccaagtt catactgcat cgggcacagc cccagggact   11820
```

```
ctgaaaaccc tgaacctgga taactatgtg ttttttggtg gccacatccg tcagcaggga    11880
acaaggcatg gaagaagtcc tcaagttggt aatggtttca ggggttgtat ggactccatt    11940
tatttgaatg ggcaggagct cccttaaac agcaaaccca gaagctatgc acacatcgaa     12000
gagtcggtgg atgtatctcc aggctgcttc ctgacggcca cggaagactg cgccagcaac    12060
ccttgccaga atggaggcgt ttgcaatccg tcacctgctg gaggttatta ctgcaaatgc    12120
agtgccttgt acatagggac ccactgtgag ataagcgtca atccgtgttc ctccaagcca    12180
tgcctctatg ggggcacgtg tgttgtcgac aacggaggct ttgtttgcca gtgtagagga    12240
ttatatactg gtcagaggtg tcagcttagt ccatactgca aagatgaacc tgtaagaat     12300
ggcggaacat gctttgacag tttggatggc gccgtttgtc agtgtgattc gggttttagg    12360
ggagaaaggt gtcagagtga tatcgacgag tgctctggaa acccttgcct gcacggggcc    12420
ctctgtgaga acacgcacgg ctcctatcac tgcaactgca gccacgagta caggggacgt    12480
cactgcgagg atgctgcgcc caaccagtat gtgtccacgc cgtggaacat gggttggcg     12540
gaaggaattg gaatcgttgt gtttgttgca gggatatttt tactggtggt ggtgtttgtt    12600
ctctgccgta agatgattag tcggaaaaag aagcatcagg ctgaacctaa agacaagcac    12660
ctgggacccg ctacggcttt cttgcaaaga ccgtatttg attccaagct aaataagaac    12720
atttactcag acataccacc ccaggtgcct gtccggccta tttcctacac cccgagtatt    12780
ccaagtgact caagaaacaa tctggaccga aattccttcg aaggatctgc tatcccagag    12840
catcccgaat tcagcacttt taaccccgag tctgtgcacg gcaccgaaaa agcagtggcg    12900
gtctgcagcg tggcgccaaa cctgcctccc ccaccccctt caaactcccc ttctgacagc    12960
gactccatcc agaagcctag ctgggacttt gactatgaca caaaagtggt ggatcttgat    13020
ccctgtcttt ccaagaagcc tctagaggaa aagccttccc agccatacag tgcccgggaa    13080
agcctgtctg aagtgcagtc tctgagctcc ttccagtccg aatcgtgcga tgacaatggg    13140
tatcactggg atacatcaga ttggatgcca agcgttcctc tgccggacat acaagagttc    13200
cccaactatg aggtgattga tgagcagaca cccctgtact cagcagatcc aaacgccatc    13260
gatacggact attaccctgg aggctacgac atcgaaagtg attttcctcc acccccagaa    13320
gacttccccg cagctgatga gctaccaccg ttaccgcccg aattcagcaa tcagtttgaa    13380
tccatccacc ctcctagaga catgcctgcc gcgggtagct tgggttcttc atcaagaaac    13440
cggcagaggt tcaacttgaa tcagtatttg cccaattttt atccccctcga tatgtctgaa    13500
cctcaaacaa aaggcactgg tgagaatagt acttgtagag aacccatgc cccttacccg    13560
ccagggtatc aaagacactt cgaggcgccc gctgtcgaga gcatgcccat gtctgtgtac    13620
gcctccaccg cctcctgctc tgacgtgtca gcctgctgcg aagtggagtc cgaggtcatg    13680
atgagtgact atgagagcgg ggacgacggc cacttcgaag aggtgacgat cccgcccctg    13740
gattcccagc agcacacgga agtctga                                       13767
```

<210> SEQ ID NO 2
<211> LENGTH: 25
<212> TYPE: DNA
<213> ORGANISM: Homo sapiens
<220> FEATURE:
<221> NAME/KEY: FAT1 siRNA Sense
<222> LOCATION: (1)..(25)

<400> SEQUENCE: 2
cccaacacac cuguggucau gguaa                                         25

<210> SEQ ID NO 3
<211> LENGTH: 25
<212> TYPE: DNA
<213> ORGANISM: Homo sapiens
<220> FEATURE:
<221> NAME/KEY: FAT1 siRNA Antisense
<222> LOCATION: (1)..(25)

<400> SEQUENCE: 3
uuaccaugac cacaggugug uuggg                                            25

<210> SEQ ID NO 4
<211> LENGTH: 1377
<212> TYPE: DNA
<213> ORGANISM: Homo sapiens
<220> FEATURE:
<221> NAME/KEY: PDCD4 Gene
<222> LOCATION: (1)..(1377)

<400> SEQUENCE: 4

| atgaccaaat | atcctgataa | cttaagtgac | tctctctttt | ccggtgatga | agaaaatgct |   60 |
| gggactgagg | aaataaagaa | tgaaataaat | ggaaattgga | tttcagcatc | ctccattaac |  120 |
| gaagctagaa | ttaatgccaa | ggcaaaaagg | cgactaagga | aaaactcatc | ccgggactct |  180 |
| ggcagaggcg | attcggtcag | cgacagtggg | agtgacgccc | ttagaagtgg | attaactgtg |  240 |
| ccaaccagtc | caaagggaag | gttgctggat | aggcgatcca | gatctgggaa | aggaagggga |  300 |
| ctaccaaaga | aaggtggtgc | aggaggcaaa | ggtgtctggg | gtacacctgg | acaggtgtat |  360 |
| gatgtggagg | aggtggatgt | gaaagatcct | aactatgatg | atgaccagga | gaactgtgtt |  420 |
| tatgaaactg | tagttttgcc | tttggatgaa | agggcatttg | agaagacttt | aacaccaatc |  480 |
| atacaggaat | attttgagca | tggagatact | aatgaagttg | cggaaatgtt | aagagattta |  540 |
| aatcttggtg | aaatgaaaag | tggagtacca | gtgttggcag | tatccttagc | attggagggg |  600 |
| aaggctagtc | atagagagat | gacatctaag | cttctttctg | acctttgtgg | gacagtaatg |  660 |
| agcacaactg | atgtggaaaa | atcatttgat | aaattgttga | agatctacc | tgaattagca |  720 |
| ctggatactc | tagagcacc | acagttggtg | ggccagttta | ttgctagagc | tgttggagat |  780 |
| ggaattttat | gtaataccta | tattgatagt | tacaaaggaa | ctgtagattg | tgtgcaggct |  840 |
| agagctgctc | tggataaggc | taccgtgctt | ctgagtatgt | ctaaaggtgg | aaagcgtaaa |  900 |
| gatagtgtgt | ggggctctgg | aggtgggcag | caatctgtca | atcaccttgt | taaagagatt |  960 |
| gatatgctgc | tgaaagaata | tttactctct | ggagacatat | ctgaagctga | acattgcctt | 1020 |
| aaggaactgg | aagtacctca | ttttcaccat | gagcttgtat | atgaagctat | tataatggtt | 1080 |
| ttagagtcaa | ctggagaaag | tacatttaag | atgattttgg | atttattaaa | gtcccttggg | 1140 |
| aagtcttcta | ccattactgt | agaccaaatg | aaaagaggtt | atgagagaat | ttacaatgaa | 1200 |
| attccggaca | ttaatctgga | tgtcccacat | tcatactctg | tgctgagcg | tttgtagaa | 1260 |
| gaatgttttc | aggctggaat | aatttccaaa | caactcagag | atctttgtcc | ttcaaggggc | 1320 |
| agaaagcgtt | ttgtaagcga | aggagatgga | ggtcgtctta | aaccagagag | ctactga    | 1377 |

<210> SEQ ID NO 5
<211> LENGTH: 1434
<212> TYPE: DNA
<213> ORGANISM: Homo sapiens
<220> FEATURE:
<221> NAME/KEY: MMP3 Gene
<222> LOCATION: (1)..(1434)

<400> SEQUENCE: 5

```
atgaagagtc ttccaatcct actgttgctg tgcgtggcag tttgctcagc ctatccattg      60
gatggagctg caaggggtga ggacaccagc atgaaccttg ttcagaaata tctagaaaac     120
tactacgacc tcaaaaaaga tgtgaaacag tttgttagga gaaggacag tggtcctgtt     180
gttaaaaaaa tccgagaaat gcagaagttc cttggattgg aggtgacggg gaagctggac     240
tccgacactc tggaggtgat gcgcaagccc aggtgtggag ttcctgatgt tggtcacttc     300
agaaccttc ctggcatccc gaagtggagg aaaacccacc ttacatacag gattgtgaat     360
tatacaccag atttgccaaa agatgctgtt gattctgctg ttgagaaagc tctgaaagtc     420
tgggaagagg tgactccact cacattctcc aggctgtatg aaggagaggc tgatataatg     480
atctcttttg cagttagaga acatggagac ttttacccct ttgatggacc tggaaatgtt     540
ttggcccatg cctatgcccc tgggccaggg attaatggag atgcccactt tgatgatgat     600
gaacaatgga caaggatac aacagggacc aatttattc tcgttgctgc tcatgaaatt     660
ggccactccc tgggtctctt tcactcagcc aacactgaag ctttgatgta cccactctat     720
cactcactca cagacctgac tcggttccgc ctgtctcaag atgatataaa tggcattcag     780
tccctctatg gacctccccc tgactcccct gagaccccc tggtacccac ggaacctgtc     840
cctccagaac ctgggacgcc agccaactgt gatcctgctt tgtcctttga tgctgtcagc     900
actctgaggg gagaaatcct gatctttaaa gacaggcact tttggcgcaa atccctcagg     960
aagcttgaac ctgaattgca tttgatctct tcattttggc catctcttcc ttcaggcgtg    1020
gatgccgcat atgaagttac tagcaaggac ctcgttttca ttttttaaagg aaatcaattc    1080
tgggctatca gaggaaatga ggtacgagct ggatacccaa gaggcatcca caccctaggt    1140
ttccctccaa ccgtgaggaa aatcgatgca gccatttctg ataaggaaaa gaacaaaaca    1200
tatttctttg tagaggacaa atactggaga tttgatgaga agagaaattc catggagcca    1260
ggctttccca agcaaatagc tgaagacttt ccagggattg actcaaagat tgatgctgtt    1320
tttgaagaat tggggttctt ttatttcttt actggatctt cacagttgga gtttgaccca    1380
aatgcaaaga agtgacaca cactttgaag agtaacagct ggcttaattg ttga           1434
```

<210> SEQ ID NO 6
<211> LENGTH: 1245
<212> TYPE: DNA
<213> ORGANISM: Homo sapiens
<220> FEATURE:
<221> NAME/KEY: PLAU
<222> LOCATION: (1)..(1245)

<400> SEQUENCE: 6

```
atggtcttcc atttgagaac tagatacgaa caggcgaact gtgactgtct aaatggagga      60
acatgtgtgt ccaacaagta cttctccaac attcactggt gcaactgccc aaagaaattc     120
ggagggcagc actgtgaaat agataagtca aaaacctgct atgagggaa tggtcacttt     180
taccgaggaa aggccagcac tgacaccatg ggccggccct gcctgccctg gaactctgcc     240
actgtccttc agcaaacgta ccatgcccac agatctgatg ctcttcagct gggcctgggg     300
aaacataatt actgcaggaa cccagacaac cggaggcgac cctggtgcta tgtgcaggtg     360
ggcctaaagc tgcttgtcca agagtgcatg gtgcatgact gcgcagatgg aaaaaagccc     420
tcctctcctc cagaagaatt aaaatttcag tgtggccaaa agactctgag gccccgcttt     480
aagattattg ggggagaatt caccaccatc gagaaccagc cctggtttgc ggccatctac     540
```

```
aggaggcacc ggggggggctc tgtcacctac gtgtgtggag gcagcctcat cagcccttgc    600
tgggtgatca gcgccacaca ctgcttcatt gattacccaa agaaggagga ctacatcgtc    660
tacctgggtc gctcaaggct taactccaac acgcaagggg agatgaagtt tgaggtggaa    720
aacctcatcc tacacaagga ctacagcgct gacacgcttg ctcaccacaa cgacattgcc    780
ttgctgaaga tccgttccaa ggagggcagg tgtgcgcagc catcccggac tatacagacc    840
atctgcctgc cctcgatgta taacgatccc cagtttggca caagctgtga gatcactggc    900
tttggaaaag agaattctac cgactatctc tatccggagc agctgaaaat gactgttgtg    960
aagctgattt cccaccggga gtgtcagcag ccccactact acggctctga agtcaccacc   1020
aaaatgctgt gtgctgctga cccacagtgg aaaacagatt cctgccaggg agactcaggg   1080
ggacccctcg tctgttccct ccaaggccgc atgactttga ctggaattgt gagctggggc   1140
cgtggatgtg ccctgaagga caagccaggc gtctacacga gagtctcaca cttcttaccc   1200
tggatccgca gtcacaccaa ggaagagaat ggcctggccc tctga                  1245

<210> SEQ ID NO 7
<211> LENGTH: 1815
<212> TYPE: DNA
<213> ORGANISM: Homo sapiens
<220> FEATURE:
<221> NAME/KEY: COX 2
<222> LOCATION: (1)..(1815)

<400> SEQUENCE: 7
atgctcgccc gcgccctgct gctgtgcgcg gtcctggcgc tcagccatac agcaaatcct     60
tgctgttccc acccatgtca aaaccgaggt gtatgtatga gtgtgggatt tgaccagtat    120
aagtgcgatt gtacccggac aggattctat ggagaaaact gctcaacacc ggaattttg     180 acaagaataa aattatttct gaaacccact ccaaacacag tgcactacat acttacccac    240
ttcaagggat tttggaacgt tgtgaataac attcccttcc ttcgaaatgc aattatgagt    300
tatgtgttga catccagatc acatttgatt gacagtccac caacttacaa tgctgactat    360
ggctacaaaa gctgggaagc cttctctaac ctctcctatt atactagagc ccttcctcct    420
gtgcctgatg attgcccgac tcccttgggt gtcaaaggta aaagcagct tcctgattca    480 aatgagattg tggaaaaatt gcttctaaga gaaagttca tccctgatcc ccagggctca    540
aacatgatgt ttgcattctt tgcccagcac ttcacgcatc agtttttcaa gacagatcat    600
aagcgagggc cagctttcac caacgggctg ggccatgggg tggacttaaa tcatatttac    660
ggtgaaactc tggctagaca gcgtaaactg cgccttttca aggatggaaa aatgaaatat    720
cagataattg atggagagat gtatcctccc acagtcaaag atactcaggc agagatgatc    780
taccctcctc aagtccctga gcatctacgg tttgctgtgg ggcaggaggt ctttggtctg    840
gtgcctggtc tgatgatgta tgccacaatc tggctgcggg aacacaacag agtatgcgat    900
gtgcttaaac aggagcatcc tgaatggggt gatgagcagt tgttccagac aagcaggcta    960
atactgatag agagactat taagattgtg attgaagatt atgtgcaaca cttgagtggc   1020
tatcacttca aactgaaatt tgacccagaa ctacttttca caaacaatt ccagtaccaa   1080 aatcgtattg ctgctgaatt taacaccctc tatcactggc atcccttct gcctgacacc   1140 tttcaaattc atgaccagaa atacaactat caacagttta tctacaacaa ctctatattg   1200
ctggaacatg gaattcccca gtttgttgaa tcattcacca gcaaattgc tggcagggtt   1260 gctggtggta ggaatgttcc accccgcagta cagaaagtat cacaggcttc cattgaccag   1320
```

| | |
|---|---|
| agcaggcaga tgaaatacca gtctttaat gagtaccgca aacgcttat gctgaagccc | 1380 |
| tatgaatcat ttgaagaact tacaggagaa aaggaaatgt ctgcagagtt ggaagcactc | 1440 |
| tatggtgaca tcgatgctgt ggagctgtat cctgcccttc tggtagaaaa gcctcggcca | 1500 |
| gatgccatct ttggtgaaac catggtgaaa gttggagcac cattctcctt gaaaggactt | 1560 |
| atgggtaatg ttatatgttc tcctgcctac tggaagccaa gcacttttgg tggagaagtg | 1620 |
| ggttttcaaa tcatcaacac tgcctcaatt cagtctctca tctgcaataa cgtgaagggc | 1680 |
| tgtccctta cttcattcag tgttccagat ccagagctca ttaaaacagt caccatcaat | 1740 |
| gcaagttctt cccgctccgg actagatgat atcaatccca cagtactact aaaagaacgt | 1800 |
| tcgactgaac tgtag | 1815 |

```
<210> SEQ ID NO 8
<211> LENGTH: 639
<212> TYPE: DNA
<213> ORGANISM: Homo sapiens
<220> FEATURE:
<221> NAME/KEY: IL6
<222> LOCATION: (1)..(639)

<400> SEQUENCE: 8
```

| | |
|---|---|
| atgaactcct tctccacaag cgccttcggt ccagttgcct tctccctggg gctgctcctg | 60 |
| gtgttgcctg ctgccttccc tgccccagta cccccaggag aagattccaa agatgtagcc | 120 |
| gccccacaca gacagccact cacctcttca gaacgaattg acaaacaaat tcggtacatc | 180 |
| ctcgacggca tctcagccct gagaaaggag acatgtaaca gagtaacat gtgtgaaagc | 240 |
| agcaaagagg cactggcaga aaacaacctg aaccttccaa agatggctga aaagatgga | 300 |
| tgcttccaat ctggattcaa tgaggagact tgcctggtga aaatcatcac tggtcttttg | 360 |
| gagtttgagg tataccctaga gtacctccag aacagatttg agagtagtga ggaacaagcc | 420 |
| agagctgtgc agatgagtac aaaagtcctg atccagttcc tgcagaaaaa ggcaaagaat | 480 |
| ctagatgcaa taaccacccc tgacccaacc acaaatgcca gcctgctgac gaagctgcag | 540 |
| gcacagaacc agtggctgca ggacatgaca actcatctca ttctgcgcag ctttaaggag | 600 |
| ttcctgcagt ccagcctgag ggctcttcgg caaatgtag | 639 |

```
<210> SEQ ID NO 9
<211> LENGTH: 810
<212> TYPE: DNA
<213> ORGANISM: Homo sapiens
<220> FEATURE:
<221> NAME/KEY: IL1 beta
<222> LOCATION: (1)..(810)

<400> SEQUENCE: 9
```

| | |
|---|---|
| atggcagaag tacctgagct cgccagtgaa atgatggctt attacagtgg caatgaggat | 60 |
| gacttgttct ttgaagctga tggccctaaa cagatgaagt gctccttcca ggacctggac | 120 |
| ctctgcccctc tggatggcgg catccagcta cgaatctccg accaccacta cagcaagggc | 180 |
| ttcaggcagg ccgcgtcagt tgttgtggcc atggacaagc tgaggaagat gctggttccc | 240 |
| tgcccacaga cctccaggga gaatgacctg agcaccttct tcccttcat ctttgaagaa | 300 |
| gaacctatct tcttcgacac atgggataac gaggcttatg tgcacgatgc acctgtacga | 360 |
| tcactgaact gcacgctccg ggactcacag caaaaaagct tggtgatgtc tggtccatat | 420 |
| gaactgaaag ctctccacct ccagggacag gatatggagc aacaagtggt gttctccatg | 480 |

```
tcctttgtac aaggagaaga aagtaatgac aaaatacctg tggccttggg cctcaaggaa      540
aagaatctgt acctgtcctg cgtgttgaaa gatgataagc ccactctaca gctggagagt      600
gtagatccca aaaattaccc aaagaagaag atggaaaagc gatttgtctt caacaagata      660
gaaatcaata acaagctgga atttgagtct gcccagttcc ccaactggta catcagcacc      720
tctcaagcag aaaacatgcc cgtcttcctg ggagggacca aaggcggcca ggatataact      780
gacttcacca tgcaatttgt gtcttcctaa                                       810
```

<210> SEQ ID NO 10
<211> LENGTH: 1263
<212> TYPE: DNA
<213> ORGANISM: Homo sapiens
<220> FEATURE:
<221> NAME/KEY: VEGF C
<222> LOCATION: (1)..(1263)

<400> SEQUENCE: 10

```
atgcacttgc tgggcttctt ctctgtggcg tgttctctgc tcgccgctgc gctgctcccg       60
ggtcctcgcg aggcgcccgc cgccgccgcc gccttcgagt ccggactcga cctctcggac      120
gcggagcccg acgcgggcga ggccacggct tatgcaagca agatctgga ggagcagtta       180 cggtctgtgt ccagtgtaga tgaactcatg actgtactct acccagaata ttggaaaatg      240
tacaagtgtc agctaaggaa aggaggctgg caacataaca gagaacaggc caacctcaac      300
tcaaggacag aagagactat aaaatttgct gcagcacatt ataatacaga gatcttgaaa      360
agtattgata tgagtggag aaagactcaa tgcatgccac gggaggtgtg tatagatgtg       420
gggaaggagt ttggagtcgc gacaaacacc ttctttaaac ctccatgtgt gtccgtctac      480
agatgtgggg gttgctgcaa tagtgagggg ctgcagtgca tgaacaccag cacgagctac      540
ctcagcaaga cgttatttga attacagtg cctctctctc aaggccccaa accagtaaca       600
atcagttttg ccaatcacac ttcctgccga tgcatgtcta aactggatgt ttacagacaa      660
gttcattcca ttattagacg ttccctgcca gcaacactac cacagtgtca ggcagcgaac      720
aagacctgcc ccaccaatta catgtggaat aatcacatct gcagatgcct ggctcaggaa      780 gatttttatgt tttcctcgga tgctggagat gactcaacag atggattcca tgacatctgt      840
ggaccaaaca aggagctgga tgaagagacc tgtcagtgtg tctgcagagc ggggcttcgg      900
cctgccagct gtggacccca caagaactga cacagaaact catgccagtg tgtctgtaaa      960
aacaaactct cccccagcca atgtggggcc aaccgagaat tgatgaaaa cacatgccag      1020 tgtgtatgta aagaacctg ccccagaaat caacccctaa atcctggaaa atgtgcctgt      1080
gaatgtacag aaagtccaca gaaatgcttg ttaaaaggaa agaagttcca ccaccaaaca      1140
tgcagctgtt acagacggcc atgtacgaac cgccagaagg cttgtgagcc aggattttca      1200
tatagtgaag aagtgtgtcg ttgtgtccct tcatattgga aaagaccaca aatgatgagc      1260
taa                                                                   1263
```

<210> SEQ ID NO 11
<211> LENGTH: 20
<212> TYPE: DNA
<213> ORGANISM: Homo sapiens
<220> FEATURE:
<221> NAME/KEY: 18s Forward Primer
<222> LOCATION: (1)..(20)

<400> SEQUENCE: 11

```
gtaacccgtt gaaccccatt                                                   20
```

<210> SEQ ID NO 12
<211> LENGTH: 20
<212> TYPE: DNA
<213> ORGANISM: Homo sapiens
<220> FEATURE:
<221> NAME/KEY: 18s Reverse Primer
<222> LOCATION: (1)..(20)

<400> SEQUENCE: 12
ccatccaatc ggtagtagcg                                         20

<210> SEQ ID NO 13
<211> LENGTH: 25
<212> TYPE: DNA
<213> ORGANISM: Homo sapiens
<220> FEATURE:
<221> NAME/KEY: FAT1 Forward Primer
<222> LOCATION: (1)..(25)

<400> SEQUENCE: 13
ttcaaaatag gtgaagagac aggtg                                   25

<210> SEQ ID NO 14
<211> LENGTH: 25
<212> TYPE: DNA
<213> ORGANISM: Homo sapiens
<220> FEATURE:
<221> NAME/KEY: FAT1 Reverse Primer
<222> LOCATION: (1)..(25)

<400> SEQUENCE: 14
ttgtgatgag acctgtttta ggatg                                   25

<210> SEQ ID NO 15
<211> LENGTH: 21
<212> TYPE: DNA
<213> ORGANISM: Homo sapiens
<220> FEATURE:
<221> NAME/KEY: PDCD4 Forward Primer
<222> LOCATION: (1)..(21)

<400> SEQUENCE: 15
cctgcagggt attttcccta a                                       21

<210> SEQ ID NO 16
<211> LENGTH: 20
<212> TYPE: DNA
<213> ORGANISM: Homo sapiens
<220> FEATURE:
<221> NAME/KEY: PDCD4 Reverse Primer
<222> LOCATION: (1)..(20)

<400> SEQUENCE: 16
tggttggcac agttaatcca                                         20

<210> SEQ ID NO 17
<211> LENGTH: 20
<212> TYPE: DNA
<213> ORGANISM: Homo sapiens
<220> FEATURE:
<221> NAME/KEY: COX-2 Forward Primer
<222> LOCATION: (1)..(20)

<400> SEQUENCE: 17
ctgctcaaca ccggaatttt                                         20

-continued

```
<210> SEQ ID NO 18
<211> LENGTH: 21
<212> TYPE: DNA
<213> ORGANISM: Homo sapiens
<220> FEATURE:
<221> NAME/KEY: COX-2 Reverse Primer
<222> LOCATION: (1)..(21)

<400> SEQUENCE: 18
ttgaatcagg aagctgcttt t                                              21

<210> SEQ ID NO 19
<211> LENGTH: 20
<212> TYPE: DNA
<213> ORGANISM: Homo sapiens
<220> FEATURE:
<221> NAME/KEY: c-JUN Forward Primer
<222> LOCATION: (1)..(20)

<400> SEQUENCE: 19
gtgtcccccg cttgccacag                                                20

<210> SEQ ID NO 20
<211> LENGTH: 20
<212> TYPE: DNA
<213> ORGANISM: Homo sapiens
<220> FEATURE:
<221> NAME/KEY: c-JUN Reverse Primer
<222> LOCATION: (1)..(20)

<400> SEQUENCE: 20
tcggcgtggt ggtgatgtgc                                                20

<210> SEQ ID NO 21
<211> LENGTH: 20
<212> TYPE: DNA
<213> ORGANISM: Homo sapiens
<220> FEATURE:
<221> NAME/KEY: MMP3 Forward Primer
<222> LOCATION: (1)..(20)

<400> SEQUENCE: 21
cagggattaa tggagatgcc                                                20

<210> SEQ ID NO 22
<211> LENGTH: 20
<212> TYPE: DNA
<213> ORGANISM: Homo sapiens
<220> FEATURE:
<221> NAME/KEY: MMP3 Reverse Primer
<222> LOCATION: (1)..(20)

<400> SEQUENCE: 22
agtcaggggg aggtccatag                                                20

<210> SEQ ID NO 23
<211> LENGTH: 20
<212> TYPE: DNA
<213> ORGANISM: Homo sapiens
<220> FEATURE:
<221> NAME/KEY: VEGF-C Forward Primer
<222> LOCATION: (1)..(20)

<400> SEQUENCE: 23
tgaacaccag cacgagctac                                                20
```

```
<210> SEQ ID NO 24
<211> LENGTH: 21
<212> TYPE: DNA
<213> ORGANISM: Homo sapiens
<220> FEATURE:
<221> NAME/KEY: VEGF-C Reverse Primer
<222> LOCATION: (1)..(21)

<400> SEQUENCE: 24
gttgagtcat ctccagcatc c                                              21

<210> SEQ ID NO 25
<211> LENGTH: 20
<212> TYPE: DNA
<213> ORGANISM: Homo sapiens
<220> FEATURE:
<221> NAME/KEY: IL1 beta Forward Primer
<222> LOCATION: (1)..(20)

<400> SEQUENCE: 25
gagcaccttc tttcccttca                                                20

<210> SEQ ID NO 26
<211> LENGTH: 20
<212> TYPE: DNA
<213> ORGANISM: Homo sapiens
<220> FEATURE:
<221> NAME/KEY: IL1beta Reverse Primer
<222> LOCATION: (1)..(20)

<400> SEQUENCE: 26
tcatctttca acacgcagga                                                20

<210> SEQ ID NO 27
<211> LENGTH: 20
<212> TYPE: DNA
<213> ORGANISM: Homo sapiens
<220> FEATURE:
<221> NAME/KEY: IL6 Forward Primer
<222> LOCATION: (1)..(20)

<400> SEQUENCE: 27
atgaggagac ttgcctggtg                                                20

<210> SEQ ID NO 28
<211> LENGTH: 19
<212> TYPE: DNA
<213> ORGANISM: Homo sapiens
<220> FEATURE:
<221> NAME/KEY: IL6 Reverse Primer
<222> LOCATION: (1)..(19)

<400> SEQUENCE: 28
gcatttgtgg ttgggtcag                                                 19

<210> SEQ ID NO 29
<211> LENGTH: 23
<212> TYPE: DNA
<213> ORGANISM: Homo sapiens
<220> FEATURE:
<221> NAME/KEY: PLAU Forward Primer
<222> LOCATION: (1)..(23)

<400> SEQUENCE: 29
agcgactcca aaggcagcaa tga                                            23

<210> SEQ ID NO 30
```

```
<211> LENGTH: 20
<212> TYPE: DNA
<213> ORGANISM: Homo sapiens
<220> FEATURE:
<221> NAME/KEY: PLAU Reverse Primer
<222> LOCATION: (1)..(20)

<400> SEQUENCE: 30
cagggtcgcc tccggttgtc                                          20
```